(12) United States Patent
Klar et al.

(10) Patent No.: US 7,125,893 B1
(45) Date of Patent: Oct. 24, 2006

(54) 6-ALKENYL-, 6-ALKINYL- AND 6-EPOXY-EPOTHILONE DERIVATIVES, PROCESS FOR THEIR PRODUCTION, AND THEIR USE IN PHARMACEUTICAL PREPARATIONS

(75) Inventors: Ulrich Klar, Berlin (DE); Wolfgang Schwede, Berlin (DE); Werner Skuballa, Berlin (DE); Bernd Buchmann, Hohen Neuendorf (DE); Jens Hoffmann, Muhlenbeck (DE); Rosemarie Lichtner, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/979,939

(22) PCT Filed: May 1, 2000

(86) PCT No.: PCT/IB00/00657

§ 371 (c)(1),
(2), (4) Date: Jun. 6, 2002

(87) PCT Pub. No.: WO00/66589

PCT Pub. Date: Nov. 9, 2000

(30) Foreign Application Priority Data

Apr. 30, 1999 (DE) .............................. 199 21 086
Nov. 4, 1999 (DE) .............................. 199 54 228
Mar. 9, 2000 (DE) .............................. 100 13 363
Mar. 27, 2000 (DE) .............................. 100 15 836

(51) Int. Cl.
*A61K 31/47* (2006.01)
*A61K 31/41* (2006.01)
*A61K 31/42* (2006.01)
*C07D 225/00* (2006.01)
*C07D 491/00* (2006.01)

(52) U.S. Cl. ................. 514/314; 514/312; 514/313; 514/359; 514/367; 514/373; 514/375; 514/376; 514/377; 514/380; 540/451; 540/462; 546/153; 546/156; 546/157; 546/158; 546/160; 548/159; 548/161; 548/164; 548/221; 548/222

(58) Field of Classification Search ................. 514/439, 514/314, 312, 313, 359; 548/159, 161, 164, 548/221, 222; 540/451, 462; 546/153, 156, 546/157, 158, 160

See application file for complete search history.

(56) References Cited

U.S. PATENT DOCUMENTS

| 5,969,145 | A | 10/1999 | Schinzer et al. |
| 6,043,372 | A | 3/2000 | Schinzer et al. |
| 6,156,905 | A | 12/2000 | Schinzer et al. |
| 6,730,699 | B1 * | 5/2004 | Li et al. |
| 2002/0058817 | A1 | 5/2002 | Danishefsky |
| 2004/0012735 | A1 | 1/2004 | Sato et al. |
| 2004/0019088 | A1 | 1/2004 | Lichtner et al. |

FOREIGN PATENT DOCUMENTS

| DE | 4138042 | 5/1993 |
| DE | 19636343 | 10/1997 |
| DE | 19701758 | 7/1998 |
| WO | WO 9719086 | 5/1997 |
| WO | WO 9808849 | 3/1998 |
| WO | WO 98/25929 | 6/1998 |
| WO | WO 99/01124 | 1/1999 |
| WO | WO 99/02514 | 1/1999 |
| WO | WO 99/07692 | 2/1999 |
| WO | WO 99/67253 | 12/1999 |
| WO | WO 01/66154 | 9/2001 |
| WO | WO 2004015088 | * 2/2004 |

OTHER PUBLICATIONS

K.C. Nicolaou, "Synthesis of Epothilones A and B in Solid and Solution Phase", Nature, vol. 387, (1997), pp. 268-272.
K.C. Nicolaou et al.: "Designed Epothilones: Combinatorial Synthesis, Tubulin Assembly Properties, And Cytotoxic Action Against Taxol.Resistant Tumor Cells" Angewandte Chemie. International Edition, DE. Verlag Chemie. Weinheim, vol. 36, No. 19, 1997, pp. 2097-2103, XP002064441.

(Continued)

*Primary Examiner*—Cecilia J. Tsang
*Assistant Examiner*—Binta Robinson
(74) *Attorney, Agent, or Firm*—Millen, White, Zelano, Branigan, P.C.

(57) ABSTRACT

This invention describes the new 6-alkenyl- and 6-alkinyl-epothilone derivatives of general formula I

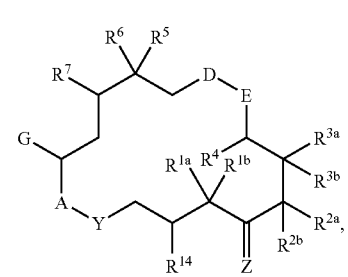

in which $R^{1a}$, $R^{1b}$, $R^{2a}$, $R^{3a}$, $R^{3b}$, $R^4$, $R^5$, $R^6$, $R^7$, A, Y, D, E, G, Y and Z are as defined in the specification. The compounds are useful in treating malignant tumours, for example, ovarian, stomach, colon, breast, adeno-, head and neck carcinomas, acute lymphocytic and myelocytic leukemia. In addition, these compounds are suitable for anti-angiogenesis therapy as well as for treatment of chronic inflammatory diseases such as psoriasis and arthritis. Methods of use and preparation of the compounds are also described.

24 Claims, No Drawings

OTHER PUBLICATIONS

K.C. Nicolaou et al.: "Chemical Biology of Epothilones" Angewandte Chemie. International Edition, De. Verlag Chemie. Weinheim, vol. 37, No. 13, Aug. 1998 pp. 2014-2045, XP002131418.

Zhen Yang, et al. Die Totalysynthese von Epothilon A: der Zugang durch Olefinmetathese ** Angew. Chem (1997), 109, Nr. 112, pp. 170-172.

Dieter Schinzer et al., Totalsynthese von (-)-Epothilon A**, Angew. Chem. 1997, 109. Nr. 5), pp. 543-544.

K.C. Nicolaou et al., The Olefin Metathesis Approach to Epothilone A and Its Analogs and Chemical Abstracts 26-Biomolecules and Their Synthetic Analogs, vol. 132, No. 22 (2000), p. 674.

W. Clark Still et al.: Tetrahedron Letters, Bd. 21, 1980, Seiten 1031-4, XP002095727.

K. A. Parker et al.: Journal of Organic Chemistry, Bd. 52, Nr. 19, 1987, Seiten 4369-77, XP002095726.

K. Tamao et al.: Journal of the Chemical Society, Chemical Communications, 1988, Seiten 795-7, XP002095725.

D. Schinzer et al.: Chemistry—A European Journal, Bd. 2, Nr. 11, 1996, Seiten 1477-82, XP002095724 in der Anmeldung erwaehnt.

K. C. Nicolaou et al.: Angewandte Chemie, Bd. 109, Nr. 19, 1997, Seiten 2181-7, XP002095723 in der Anmeldung erwaehnt.

K. C. Nicolaou et al.: Journal of the American Chemical Society, Bd. 119, Nr. 34, 1997, Seiten 7974-91, XP002095719 in der Anmeldung erwaehnt.

K. C. Nicolaou et al.: Chem. Eur. J. vol. 3, No. 12, 1997, No. 1.

K .C. Nicolaou et al. CA Ref # 132:293587 (2000).

U.S. Appl. No. 09/485,292.

U.S. Appl. No. 09/913,163.

* cited by examiner

6-ALKENYL-, 6-ALKINYL- AND 6-EPOXY-EPOTHILONE DERIVATIVES, PROCESS FOR THEIR PRODUCTION, AND THEIR USE IN PHARMACEUTICAL PREPARATIONS

This application is a 371 National Phase application of PCT/IB00/000657, filed May 1, 2000.

BACKGROUND OF THE INVENTION

Höfle et al. describe the cytotoxic action of the natural substances epothilone A (R=hydrogen) and epothilone B (R=methyl) of the following formula:

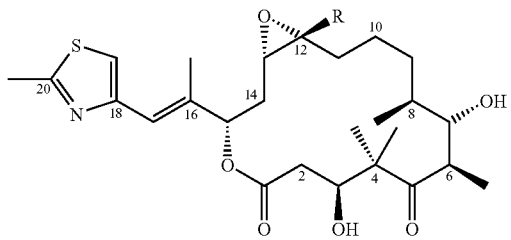

in, e.g., Angew. Chem. [Applied Chem.], 1996, 108, 1671–1673. Because of their in-vitro selectivity for breast cell lines and intestinal cell lines and their significantly higher activity against P-glycoprotein-forming multiresistant tumor lines in comparison to taxol as well as their physical properties that are superior to those of taxol, e.g., a water solubility that is higher by a factor of 30, this novel structural class is especially advantageous for the development of a pharmaceutical agent for treating malignant tumors.

The natural substances are not sufficiently stable either chemically or metabolically for the development of pharmaceutical agents. To eliminate these drawbacks, modifications to the natural substance are necessary. Such modifications are possible only with a total-synthesis approach and require synthesis strategies that make possible a broad modification of the natural substance. The purpose of the structural changes is also to increase the therapeutic range. This can be done by improving the selectivity of the action and/or increasing the active strength and/or reducing undesirable toxic side-effects, as they are described in Proc. Natl. Acad. Sci. USA 1998, 95, 9642–9647.

The total synthesis of epothilone A is described by Schinzer et al. in Chem. Eur. J. 1996, 2, No. 11, 1477–1482 and in Angew. Chem. 1997, 109, No. 5, pp. 543–544). Epothilone derivatives were already described by Höfle et al. in WO 97/19086. These derivatives were produced starting from natural epothilone A or B. Also, epothilones C and D (double bond between carbon atoms 12 and 13: epothilone C=deoxyepothilone A; epothilone D=deoxyepothilone B) are described as possible starting products for this purpose.

Another synthesis of epothilone and epothilone derivatives was described by Nicolaou et al. in Angew. Chem. 1997, 109, No. 1/2, pp. 170–172. The synthesis of epothilone A and B and several epothilone analogues was described in Nature, Vol. 387, 1997, pp. 268–272; and the synthesis of epothilone A and its derivatives was described in J. Am. Chem. Soc., Vol. 119, No. 34, 1997, pp. 7960–7973 as well as the synthesis of epothilone A and B and several epothilone analogues in J. Am. Chem. Soc., Vol. 119, No. 34, 1997, pp. 7974–7991 also by Nicolaou et al.

Nicolaou et al. also describe in Angew. Chem. 1997, 109, No. 19, pp. 2181–2187 the production of epothilone A analogues using combinative solid-phase synthesis. Several epothilone B analogues are also described there.

Epothilone derivatives, in some cases also epothilone C and D, are also described in patent applications WO 99/07692, WO 99/02514, WO 99/01124, WO 99/67252, WO 98/25929, WO 97/19086, WO 98/38192, WO 99/22461 and WO 99/58534.

In the epothilone derivatives previously known, no alkenyl, alkinyl or epoxy radical was provided on carbon atom 6 (see the above formula) of the epothilone skeleton.

SUMMARY OF THE INVENTION

An object of this invention was to make available new epothilone derivatives, which are both chemically and metabolically stable enough for the development of pharmaceutical agents and which are superior to natural derivatives in terms of their therapeutic range, their selectivity of action and/or undesirable toxic side-effects and/or their active strength.

Upon further study of the specification and appended claims, further objects and advantages of this invention will become apparent to those skilled in the art.

Included in the invention are new epothilone derivatives and compounds of general formula I,

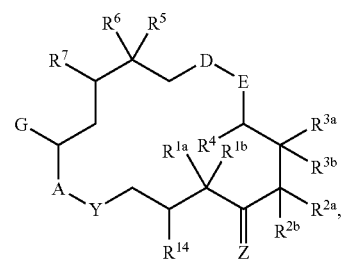

in which $R^{1a}$, $R^{1b}$ are the same or different and mean hydrogen, $C_1$–$C_{10}$ alkyl, $C_6$–$C_{12}$ aryl or $C_7$–$C_{20}$ aralkyl, all optionally substituted, or together a —$(CH_2)_m$— group with m=1, 2, 3, 4 or 5 or a —$(CH_2)$—O—$(CH_2)$— group, $R^{2a}$ means hydrogen, $C_1$–$C_{10}$ alkyl, $C_1$–$C_{12}$ aryl or $C_7$–$C_{20}$ aralkyl, all optionally substituted, —$(CH_2)_{ra}$—C≡C—$(CH_2)_{pa}$—$R^{26a}$, —$(CH_2)_{ra}$—C═C—$(CH_2)_{pa}$—$R^{26a}$,

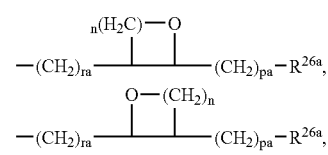

$R^{2b}$ means —$(CH_2)_{rb}$—C≡C—$(CH_2)_{pb}$—$R^{26b}$, —$(CH_2)_{rb}$—C═C—$(CH_2)_{pb}$—$R^{26b}$,

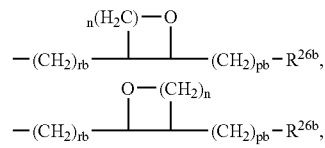

n means 0 to 5, ra, rb are the same or different and mean 0 to 4, pa, pb are the same or different and mean 0 to 3, $R^{3a}$ means hydrogen, $C_1$–$C_{10}$ alkyl, $C_6$–$C_{12}$ aryl, or $C_7$–$C_{20}$ aralkyl, all optionally substituted $R^{14}$ means hydrogen, $OR^{14a}$, Hal, $R^{3b}$ means OH or $OPG^{14}$, $R^4$ means hydrogen, $C_1$–$C_{10}$ alkyl, $C_6$–$C_{12}$ aryl, or $C_7$–$C_{20}$ aralkyl, all optionally substitued Hal, $OR^{25}$, CN, $R^{25}$ means hydrogen, a protective group $PG^5$, $R^{26a}$, $R^{26b}$ are the same or different and mean hydrogen, $C_1$–$C_{10}$ alkyl, $C_6$–$C_{12}$ aryl, or $C_1$–$C_{20}$ aralkyl, all optionally substituted, $C_1$–$C_{10}$ acyl, or, if pa or pb>0, additionally a group $OR^{27}$, $R^{27}$ means hydrogen, a protective group $PG^6$, $R^5$ means hydrogen, $C_1$–$C_{10}$ alkyl, $C_6$–$C_{12}$ aryl, $C_7$–$C_{20}$ aralkyl, all optionally substituted $(CH_2)_s$-T, whereby s stands for 1, 2, 3 or 4, T stands for $OR^{22}$ or Hal, $R^{22}$ stands for hydrogen or a protective group $PG^4$ $R^6$, $R^7$ each mean a hydrogen atom, or taken together an additional bond or an oxygen atom, G means a group $X=CR^8$—, a bi- or tricyclic aryl radical, $R^8$ means hydrogen, halogen, CN, $C_1$–$C_{20}$ alkyl, $C_6$–$C_{12}$ aryl, $C_7$–$C_{20}$ aralkyl, which can all be substituted, X means an oxygen atom, two alkoxy groups $OR^{23}$, a $C_2$–$C_{10}$-alkylene-α,ω-dioxy group, which can be straight-chain or branched, $H/OR^9$ or a grouping $CR^{10}R^{11}$, whereby $R^{23}$ stands for a $C_1$–$C_{20}$ alkyl radical, optionally substituted $R^9$ stands for hydrogen or a protective group $PG^x$, $R^{10}$, $R^{11}$ are the same or different and stand for hydrogen, a $C_1$–$C_{20}$ alkyl, $C_6$–$C_{12}$ aryl, or $C_7$–$C_{20}$ aralkyl radical, all optionally substituted, or $R^{10}$ and $R^{11}$ together with the methylene carbon atom jointly stand for a 5- to 7-membered carbocyclic ring, D-E means a group —$CH_2$—$CH_2$—, —O—$CH_2$—, A-Y means a group O—C(=O), O—$CH_2$, $CH_2$C(=O), $NR^{29}$—C(=O), $NR^{29}$—$SO_2$, $R^{29}$ means hydrogen, $C_1$–$C_{10}$ alkyl, Z means an oxygen atom or $H/OR^{12}$, whereby $R^{12}$ is hydrogen or a protective group $PG^z$, Hal means halogen, preferably fluorine, chlorine, bromine or iodine.

The production of the new epothilone derivatives and compounds can be performed by linkage of three partial fragments $A_f$, $B_f$ and $C_f$ which process is a further aspect of the invention. The interfaces between the fragments are as indicated by the three lines crossing bands in general formula I'.

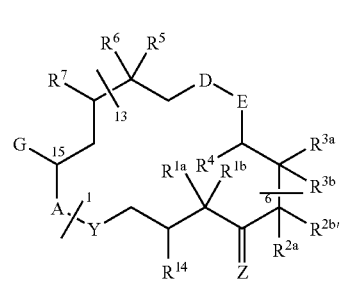

A means a $C_1$–$C_6$ fragment (epothilone numbering system) of general formula A-1 or A-2

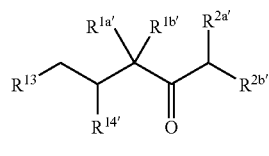

A-1 or

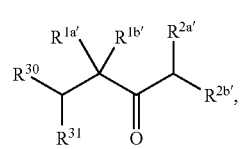

A-2 in which $R^{1a'}$, $R^{1b'}$, $R^{2a'}$ and $R^{2b'}$ have the meanings already mentioned for $R^{1a}$, $R^{1b}$, $R^{2a}$ and $R^{2b}$ and $R^{13}$ means $CH_2OR^{13a}$, $CH_2$-Hal, CHO, $CO_2R^{13b}$, COHal, $R^{14'}$ means hydrogen, $OR^{14a}$, Hal, $OSO_2R^{14b}$, $R^{13a}$, $R^{14a}$ mean hydrogen, $SO_2$-alkyl, $SO_2$-aryl, $SO_2$-aralkyl or together a —$(CH_2)_o$— group or together a $CR^{15a}R^{15b}$ group, $R^{13b}$, $R^{14b}$ mean hydrogen, $C_1$–$C_{20}$ alkyl, $C_6$–$C_{12}$ aryl, $C_7$–$C_{20}$ aralkyl, each optionally substituted $R^{15a}$, $R^{15b}$ are the same or different and mean hydrogen, $C_1$–$C_{10}$ alkyl, aryl, $C_7$–$C_{20}$ aralkyl or together a —$(CH_2)_q$ group, o means 2 to 4, q means 3 to 6, $R^{30}$ means hydrogen, $R^{31}$ means hydroxyl, or $R^{30}$, $R^{31}$ together mean an oxygen atom or a $C_2$–$C_{10}$ alkylene-α,ω-dioxy group, which can be straight-chain or branched, or $R^{30}$, $R^{31}$ independently mean a $C_1$–$C_{10}$ alkoxy group, including all stereoisomers as well as their mixtures, and free hydroxyl groups in $R^{13}$, $R^{14}$ and $R^{31}$ can be etherified or esterified, free carbonyl groups can be ketalized in A-1 or A-2 and $R^{13}$, converted into an enol ether or reduced, and free acid groups in A-1 or A-2 can be converted into their salts with bases.

$B_f$ stands for a $C_7$–$C_{12}$ fragment (epothilone numbering system) of general formula

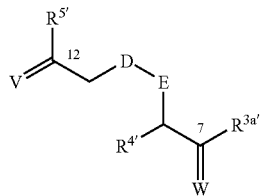

in which
D, E, $R^{3a'}$, $R^{4'}$ and $R^{5'}$ have the meanings already mentioned for D, E, $R^{3a}$, $R^4$, and $R^5$, and V means an oxygen atom, two alkoxy groups $OR^{17}$, a $C_2$–$C_{10}$ alkylene-α,ω-dioxy group, which can be straight-chain or branched or $H/OR^{16}$, W means an oxygen atom, two alkoxy groups $OR^{19}$, a $C_2$–$C_{10}$-alkylene-α,ω-dioxy group, which can be straight-chain or branched or $H/OR^{18}$, $R^{16}$, $R^{18}$, independently of one another, mean hydrogen or a protective group $PG^1$, $R^{17}$, $R^{19}$, independently of one another, mean $C_1$–$C_{20}$ alkyl optionally substituted, $C_f$ stands for a C13–C16 fragment (epothilone numbering system) of general formula

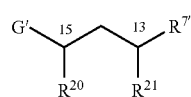

in which
G' means a group $X=CR^{8'}$—, a bicyclic or tricylic aryl radical, $R^{8'}$ has the meaning already mentioned in general formula I for $R^8$, and $R^{7'}$ means a hydrogen atom, $R^{20}$ means halogen, $N_3$, $NHR^{29}$, a hydroxy group, a protected hydroxy group $O$—$PG^2$, a protected amino group $NR^{29}PG^2$, a $C_1$–$C_{10}$ alkylsulfonyloxy group, which optionally can be perfluorinated, a benzoyloxy group that is optionally substituted by $C_1$–$C_4$ alkyl, nitro, chlorine or bromine, an $NR^{29}SO_2CH_3$ group, an $NR^{29}C(=O)CH_3$ group, a $CH_2$—$C(=O)$—$CH_3$ group, $R^{21}$ means a hydroxy group, halogen, a protected hydroxy group $OPG^3$, a phosphonium halide radical. $PPh_3{}^+Hal^-$ (Ph=phenyl; Hal=F, Cl, Br, I), a phosphonate radical $P(O)(OQ)_2$ ($Q=C_1$–$C_{10}$ alkyl or phenyl) or a phosphine oxide radical $P(O)Ph_2$ (Ph=phenyl), X means an oxygen atom, two alkoxy groups $OR^{23}$, a $C_2$–$C_{10}$ alkylene-α,ω-dioxy group, which can be straight-chain or branched, $H/OR^9$ or a grouping $CR^{10}R^{11}$, whereby $R^{23}$ stands for a $C_1$–$C_{20}$ alkyl radical, $R^9$ stands for hydrogen or a protective group $PG^3$, $R^{10}$, $R^{11}$ are the same or different and stand for hydrogen, a $C_1$–$C_{20}$ alkyl, $C_6$–$C_{12}$ aryl, or $C_7$–$C_{20}$ aralkyl radical, each optionally substituted, or $R^{10}$ and $R^{11}$ together with the methylene carbon atom commonly stand for a 5- to 7-membered carbocyclic ring.

As alkyl groups $R^{1a}$, $R^{1b}$, $R^{2a}$, $R^{2b}$, $R^{3a}$, $R^4$, $R^5$, $R^8$, $R^{10}$, $R^{11}$, $R^{13a}$, $R^{13b}$, $R^{14a}$, $R^{14b}$, $R^{15a}$, $R^{15b}$, $R^{17}$, $R^{19}$, $R^{23}$, $R^{26a}$, $R^{26b}$, $R^{28a}$, $R^{28b}$ and $R^{29}$, straight-chain or branched-chain alkyl groups with 1–20 carbon atoms can be considered, such as, for example, methyl, ethyl, propyl, isopropyl, butyl, isobutyl, tert-butyl, pentyl, isopentyl, neopentyl, heptyl, hexyl, and decyl.

Alkyl groups $R^{1a}$, $R^{1b}$, $R^{2a}$, $R^{2b}$, $R^{3a}$, $R^4$, $R^5$, $R^8$, $R^{10}$, $R^{11}$, $R^{13a}$, $R^{13b}$, $R^{14a}$, $R^{14b}$, $R^{15a}$, $R^{15b}$, $R^{17}$, $R^{19}$, $R^{23}$, $R^{26a}$, $R^{26b}$, $R^{28a}$ and $R^{28b}$ can be perfluorinated or substituted by 1–5 halogen atoms, hydroxy groups, $C_1$–$C_4$ alkoxy groups, $C_6$–$C_{12}$ aryl groups (which can be substituted by 1–3 halogen atoms).

As aryl radicals above and below, particularly $R^{1a}$, $R^{1b}$, $R^{2a}$, $R^{2b}$, $R^{3a}$, $R^4$, $R^5$, $R^8$, $R^{10}$, $R^{11}$, $R^{13a}$, $R^{13b}$, $R^{14a}$, $R^{14b}$, $R^{15a}$, $R^{15b}$, $R^{26a}$, $R^{26b}$, $R^{28a}$ and $R^{28b}$, substituted and unsubstituted carbocyclic or heterocyclic radicals with one or more heteroatoms, such as, e.g., phenyl, naphthyl, furyl, thienyl, pyridyl, pyrazolyl, pyrimidinyl, oxazolyl, pyridazinyl, pyrazinyl, quinolyl, thiazolyl, benzothiazolyl and benzoxazolyl, which can be substituted in one or more places by halogen, OH, O-alkyl, $CO_2H$, $CO_2$-alkyl, —$NH_2$, —$NO_2$, —$N_3$, —CN, $C_1$–$C_{20}$ alkyl, $C_1$–$C_{20}$ acyl, $C_1$–$C_{20}$ acyloxy groups, are suitable examples.

As bi- and tricyclic aryl radicals G or G', substituted and unsubstituted, carbocyclic or heterocyclic radicals with one or more heteroatoms, such as, e.g., naphthyl, anthryl, benzothiazolyl, benzoxazolyl, benzimidazolyl, quinolyl, isoquinolyl, benzoxazinyl, benzofuranyl, indolyl, indazolyl, quinoxalinyl, tetrahydroisoquinolinyl, tetrahydroquinolinyl, thienopyridinyl, pyridopyridinyl, benzopyrazolyl, benzotriazolyl, dihydroindolyl, which can be substituted in one or more places by halogen, OH, O-alkyl, $CO_2H$, $CO_2$-alkyl, —$NH_2$, —$NO_2$, —$N_3$, —CN, $C_1$–$C_{20}$ alkyl, $C_1$–$C_{20}$ acyl, $C_1$–$C_{20}$ acyloxy groups, are suitable.

The aralkyl groups in $R^{1a}$, $R^{1b}$, $R^{2a}$, $R^{2b}$, $R^{3a}$, $R^4$, $R^5$, $R^8$, $R^{10}$, $R^{11}$, $R^{13a}$, $R^{13b}$, $R^{14a}$, $R^{14b}$, $R^{15a}$, $R^{15b}$, $R^{26a}$, $R^{26b}$, $R^{28a}$ and $R^{28b}$ can contain in the ring(s) up to 14 C atoms, preferably 6 to 10, and in the alkyl chain 1 to 8, preferably 1 to 4 atoms. As aralkyl radicals, for example, benzyl, phenylethyl, naphthylmethyl, naphthylethyl, furylmethyl, thienylethyl and pyridinylpropyl are suitable. The rings can be substituted in one or more places by halogen, OH, O-alkyl, $CO_2H$, $CO_2$-alkyl, —$NO_2$, —$N_3$, —CN, $C_1$–$C_{20}$ alkyl, $C_1$–$C_{20}$ acyl, $C_1$–$C_{20}$ acyloxy groups.

The alkoxy groups that are contained in $R^{30}$, $R^{31}$ and X in general formula I are in each case to contain 1 to 20 carbon atoms, whereby methoxy, ethoxy, propoxy, isopropoxy and t-butyloxy groups are preferred.

As representatives of all the protective groups PG (i.e., each of the PG groups including those with a superscript), alkyl- and/or aryl-substituted silyl, $C_1$–$C_{20}$ alkyl, $C_4$–$C_7$ cycloalkyl, which in addition can contain an oxygen atom in the ring, aryl, $C_7$–$C_{20}$ aralkyl, $C_1$–$C_{20}$ acyl, aroyl and $C_1$–$C_{20}$ alkoxycarbonyl can be mentioned. Other protective groups are known in the art and can be used as known.

As alkyl, silyl and acyl radicals for protective groups PG, the radicals that are known to one skilled in the art are suitable. Preferred are alkyl or silyl radicals that can be easily cleaved from the corresponding alkyl and silyl ethers, such as, for example, the methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl radical as well as alkylsulfonyl and arylsulfonyl radicals. As acyl radicals, e.g., formyl, acetyl, propionyl, isopropionyl, pivalyl, butyryl or benzoyl, which can be substituted with amino and/or hydroxy groups, are suitable.

As amino protective groups, the radicals that are known to one skilled in the art are suitable. For example, the Alloc-, Boc-, Z-, benzyl, f-Moc, Troc, Stabase or Benzostabase group can be mentioned.

Acyl groups PG can contain 1 to 20 carbon atoms, whereby formyl, acetyl, propionyl, isopropionyl and pivalyl groups are preferred.

Index m in the alkylene group that is formed from $R^{1a}$ and $R^{1b}$ preferably stands for 1, 2, 3 or 4.

The $C_2$–$C_{10}$ alkylene-α,ω-oxy group that is possible for $R^{30}$, $R^{31}$, U, V, W and X is preferably an ethyleneketal or neopentylketal group.

The compounds that are mentioned below are preferred according to the invention:

(4S,7R,8S,9S,13E/Z,16S(E))-4,8-Dihydroxy-16-(1-methyl-2-(2-pyridyl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-methyl-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-pyridyl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-fluoro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-pyridyl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-chloro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-oxa-5,5,9,13-tetramethyl-7-(but-3-en-1-yl)-cyclohexadec-13-ene-2,6-dione (1S/R),3S(E),7S,10R,11R,12S,16R/S)-7,11-dihydroxy-10-(but-3-en-1-yl)-3-(1-methyl-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-pyridyl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-fluoro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-pyridyl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-chloro-2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-methyl-2-(2-pyridyl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-methyl-2-(2-pyridyl)ethenyl)- 8,8,12,16-tetramethyl-4,17-dioxabicyclo[14.1.0]heptadecane-5,9-dione (4S,7R(RS),8S,9S,13E/Z,16S(E))-4,8-dihydroxy-16-(2-(2-pyridyl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-fluoro-2-(2-pyridyl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-fluoro-2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8'-dihydroxy-16-(1-chloro-2-(2-pyridyl)ethenyl)-1-oxa-5,5,9,13-tetramethyl-7-(2-oxacyclopropyl-1-ethyl)-cyclohexadec-13-ene-2,6-dione (1S/R, 3S(E),7S,10R(RS), 1R,12S,16R/S)-7,11-dihydroxy-10-(2-oxacyclopropyl-1-ethyl)-3-(1-chloro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-pyridyl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-Dihydroxy-16-(1-chloro-2-(2-pyridyl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-Dihydroxy-10-(prop-2-in-1-yl)-3-(1-chloro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-pyridyl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-pyridyl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-chloro-2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-methyl-2-(2-pyridyl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-methyl-2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(2-(2-pyridyl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-fluoro-2-(2-pyridyl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-pyridyl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-chloro-2-(2-pyridyl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-methyl-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-fluoro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-chloro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-methyl-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-fluoro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-chloro-2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-methyl-2-(2-methylthiazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-methyl-2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(2-(2-methylthiazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,(10R(RS),11R,12S,16R/S)-7,11-dihydroxy-10-(2-oxacyclopropyl-1-ethyl)-3-(2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-fluoro-2-(2-methylthiazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-fluoro-2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-chloro-2-(2-methylthiazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-chloro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z, 16S(E))-4,8-dihydroxy-16-(1-chloro-2-(2-methylthiazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-chloro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-chloro-2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-methyl-2-(2-methylthiazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-methyl-2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(2-(2-methylthiazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-fluoro-2-(2-methylthiazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-methylthiazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-chloro-2-(2-methylthiazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-methyl-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-fluoro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-oxa-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-chloro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-methyl-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-fluoro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-oxa-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-chloro-2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-methyl-2-(2-methyloxazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-methyl-2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(2-(2-methyloxazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-fluoro-2-(2-methyloxazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-fluoro-2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-chloro-2-(2-methyloxazol-4-yl)ethenyl)-1-oxa-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-chloro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-oxa-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-chloro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-oxa-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-chloro-2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-methyl-2-(2-methyloxazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-methyl-2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(2-(2-methyloxazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-fluoro-2-(2-methyloxazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-methyloxazol-4-yl)ethenyl)-8,8,12,16-tetramethyl-4,17-dioxabicyclo[14.1.0]heptadecane-5,9-dione (4S,7R(RS),8S,9S,13E/Z,16S(E))-4,8-dihydroxy-16-(1-chloro-2-(2-methyloxazol-4-yl)ethenyl)-1-oxa-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-oxa-5,5-trimethylene-9,13-dimethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-methyl-2-(2-pyridyl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-pyridyl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-pyridyl)ethenyl)-8,8-trimethylene-12,16-dimethyl-4,17-dioxabicyclo[14.1.0]heptadecane-5,9-dione (4S,7R(RS),8S,9S,13E/Z,16S(E))-4,8-dihydroxy-16-(1-fluoro-2-(2-pyridyl)ethenyl)-1-oxa-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-pyridyl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-oxa-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-methylthiazol-4-yl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-oxa-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methylthiazol-4-yl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-oxa-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-methylthiazol-4-yl)ethenyl)-8,8-trimethylene-12,16-dimethyl-4,17-dioxabicyclo[14.1.0]heptadecane-5,9-dione (4S,7R(RS),8S,9S,13E/Z,16S(E))-4,8-dihydroxy-16-(1-fluoro-2-(2-methylthiazol-4-yl)ethenyl)-1-oxa-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-methylthiazol-4-yl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-oxa-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-methyloxazol-4-yl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methyloxazol-4-yl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-oxa-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-methyloxazol-4-yl)ethenyl)-8,8-trimethylene-12,16-dimethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-methyloxazol-4-yl)ethenyl)-8,8-trimethylene-12,16-dimethyl-4,17-dioxabicyclo[14.1.0]heptadecane-5,9-dione (4S,7R(RS),8S,9S,13E/Z,16S(E))-4,8-dihydroxy-16-(2-(2-methyloxazol-4-yl)ethenyl)-1-oxa-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-methyloxazol-4-yl)ethenyl)-8,8-trimethylene-12,16-dimethyl-4,17-dioxabicyclo[14.1.0]heptadecane-5,9-dione (4S,7R(RS),8S,9S,13E/Z,16S(E))-4,8-dihydroxy-16-(1-chloro-2-(2-methyloxazol-4-yl)ethenyl)-1-oxa-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-methyloxazol-4-yl)ethenyl)-8,8-trimethylene-12,16-dimethyl-4,17-dioxabicyclo[14.1.0]heptadecane-5,9-dione (4S,7R,8S,9S,13E/Z,16S)-4,8-dihydroxy-16-(2-methyl-benzoxazol-5-yl)-1-oxa-5,5,9,13-tetramethyl-7-(prop-2-en-1-yl)-cyclohexadec-13-ene-2,6-dione (1S/R,3S,7S 10R,11R,12S,16R/S)-7,11-dihydroxy-10-(prop-2-en-1-yl)-3-(2-methyl-benzoxazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzoxazol-5-yl)-1-oxa-5,5,9,13-tetramethyl-7-(prop-2-in-1-yl)-cyclohexadec-13-ene-2,6-dione (1S/R,3S,7S 10R,11R,12S,16R/S)-7,11-dihydroxy-10-(prop-2-in-1-yl)-3-(2-methyl-benzoxazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzoxazol-5-yl)-1-oxa-5,5,9,13-tetramethyl-7-(but-3-en-1-yl)-cyclohexadec-13-ene-2,6-dione (1S/R,3S,7S,10R,11R,12S,16R/S)-7,11-dihydroxy-10-(but-3-en-1-yl)-3-(2-methyl-benzoxazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzoxazol-5-yl)-1-oxa-5,5,9,13-tetramethyl-7-(but-3-in-1-yl)-cyclohexadec-13-ene-2,6-dione (1S/R,3S,7S,10R,11R,12S,16R/S)-7,11-dihydroxy-10-(but-3-in-1-yl)-3-(2-methyl-benzoxazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzoxazol-5-yl)-1-oxa-5,5,9,13-tetramethyl-7-(3-methyl-but-2-en-1-yl)-cyclohexadec-13-ene-2,6-dione (1S/R,3S,7S 10R,11R,12S 16R/S)-7,11-dihydroxy-10-(3-methyl-but-2-en-1-yl)-3-(2-methyl-benzoxazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzothiazol-5-yl)-1-oxa-5,5,9,13-tetramethyl-7-(prop-2-en-1-yl)-cyclohexadec-13-ene-2,6-dione (1S/R,3S,7S,10R,11R,12S,16R/S)-7,11-dihydroxy-10-(prop)-2-en-1-yl)-3-(2-methyl-benzothiazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzothiazol-5-yl)-1-oxa-5,5,9,13-tetramethyl-7-(prop-2-in-1-yl)-cyclohexadec-13-ene-2,6-dione (1S/R,3S,7S,10R,11R,12S,16R/S)-7,11-dihydroxy-10-(prop-2-in-1-yl)-3-(2-methyl-benzothiazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzothiazol-5-yl)-1-oxa-5,5,9,13-tetramethyl-7-(but-3-en-1-yl)-cyclohexadec-13-ene-2,6-dione (1S/R,3S,7S,10R,11R,12S,16R/S)-7,11-dihydroxy-10-(but-3-en-1-yl)-3-(2-methyl-benzothiazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzothiazol-5-yl)-1-oxa-5,5,9,13-tetramethyl-7-(but-3-in-1-yl)-cyclohexadec-13-ene-2,6-dione (1S/R,3S,7S,10R,11R,12S,16R/S)-7,11-dihydroxy-10-(but-3-in-1-yl)-3-(2-methyl-benzothiazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzothiazol-5-yl)-1-oxa-5,5,9,13-tetramethyl-7-(3-methyl-but-2-en-1-yl)-cyclohexadec-13-ene-2,6-dione (1S/R,3S,7S,10R,11R,12S,16R/S)-7,11-dihydroxy-10-(3-methyl-but-2-en-1-yl)-3-(2-methyl-benzothiazol-5-yl)-8,8,12,16-tetramethyl-4,17-dioxabicyclo[14.1.0]heptadecane-5,9-dione (4S,7R,8S,9S,13E/Z,16S)-4,8-dihydroxy-16-(quinolin-7-yl)-1-oxa-5,5,9,13-tetramethyl-7-(prop-2-en-1-yl)-cyclohexadec-13-ene-2,6-dione (1S/R,3S,7S,10R,11R, 12S 16R/S)-7,11-dihydroxy-10-(prop-2-en-1-yl)-3-(quinolin-7-yl)-8,8,12,16-tetramethyl-4,17-dioxabicyclo[14.1.0]heptadecane-5,9-dione (4S,7R,8S,9S,13E/Z,16S)-4,8-dihydroxy-16-(quinolin-7-yl)-1-oxa-5,5,9,13-tetramethyl-7-(prop-2-in-1-yl)-cyclohexadec-13-ene-2,6-dione (1S/R,3S,7S,10R,11R,12S,16R/S)-7,11-dihydroxy-10-(prop-2-in-1-yl)-3-(quinolin-7-yl)-8,8,12,16-tetramethyl-4,17-dioxabicyclo[14.1.0]heptadecane-5,9-dione (4S,7R,8S,9S,13E/Z,16S)-4,8-dihydroxy-16-(quinolin-7-yl)-1-oxa-5,5,9,13-tetramethyl-7-(but-3-en-1-yl)-cyclohexadec-13-ene-2,6-dione (1S/R,3S,7S,10R,11R,12S,16R/S)-7,11-dihydroxy-10-(but-3-en-1-yl)-3-(quinolin-7-yl)-8,8,12,16-tetramethyl-4,17-dioxabicyclo[14.1.0]heptadecane-5,9-dione (4S,7R,8S,9S,13E/Z,16S)-4,8-dihydroxy-16-(quinolin-7-yl)-1-oxa-5,5,9,13-tetramethyl-7-(but-3-en-1-yl)-cyclohexadec-13-ene-2,6-dione (1S/R,3S,7S,10R,11R,12S,16R/S)-7,11-dihydroxy-10-(but-3-en-1-yl)-3-(quinolin-7-yl)-8,8,12,16-tetramethyl-4,17-dioxabicyclo[14.1.0]heptadecane-5,9-dione (4S,7R,8S,9S,13E/Z,16S)-4,8-dihydroxy-16-(quinolin-7-yl)-1-oxa-5,5,9,13-tetramethyl-7-(3-methyl-but-2-en-1-yl)-cyclohexadec-13-ene-2,6-dione (1S/R,3S,7S,10R,11R,12S,16R/S)-7,11-dihydroxy-10-(3-methyl-but-2-en-1-yl)-3-(quinolin-7-yl)-8,8,12,16-tetramethyl-4,17-dioxabicyclo[14.1.0]heptadecane-5,9-dione (4S,7R,8S,9S,13E/Z,16S)-4,8-dihydroxy-16-(2-methyl-benzoxazol-5-yl)-1-aza-5,5,9,13-tetramethyl-7-(prop-2-en-1-yl)-cyclohexadec-13-ene-2,6-dione (1S/R,3S,7S,10R,11R,12S,16R/S)-7,11-dihydroxy-10-(prop-2-en-1-yl)-3-(2-methyl-benzoxazol-5-yl)-8,8,12,16-tetramethyl-4-aza-17-oxabicyclo[14.1.0]heptadecane-5,9-dione (4S,7R,8S,9S,13E/Z,16S)-4,8-dihydroxy-16-(2-methyl-benzoxazol-5-yl)-1-aza-5,5,9,13-tetramethyl-7-(prop-2-in-1-yl)-cyclohexadec-13-ene-2,6-dione (1S/R,3S,7S,10R,11R,12S,16R/S)-7,11-dihydroxy-10-(prop-2-en-1-yl)-3-(2-methyl-benzoxazol-5-yl)-8,8,12,16-tetramethyl-4-aza-17-oxabicyclo[14.1.0]heptadecane-5,9-dione (4S,7R,8S,9S,13E/Z,16S)-4,8-dihydroxy-16-(2-methyl-benzoxazol-5-yl)-1-aza-5,5,9,13-tetramethyl-7-(but-3-en-1-yl)-cyclohexadec-13-ene-2,6-dione (1S/R,3S,7S,10R,11R,12S,16R/S)-7,11-dihydroxy-10-(but-3-en-1-yl)-3-(2-methyl-benzoxazol-5-yl)-8,8,12,16-tetramethyl-4-aza-17-oxabicyclo[14.1.0]heptadecane-5,9-dione (4S,7R,8S,9S,13E/Z,16S)-4,8-dihydroxy-16-(2-methyl-benzoxazol-5-yl)-1-aza-5,5,9,13-tetramethyl-7-(but-3-in-1-yl)-cyclohexadec-13-ene-2,6-dione (1S/R,3S,7S,10R,11R,12S,16R/S)-7,11-dihydroxy-10-(but-3-en-1-yl)-3-(2-methyl-benzoxazol-5-yl)-8,8,12,16-tetramethyl-4-aza-17-oxabicyclo[14.1.0]heptadecane-5,9-dione (4S,7R,8S,9S,13E/Z,16S)-4,8-dihydroxy-16-(2-methyl-benzoxazol-5-yl)-1-aza-5,5,9,13-tetramethyl-7-(3-methyl-but-2-en-1-yl)-cyclohexadec-13-ene-2,6-dione (1S/R,3S,7S,10R,11R,12S,16R/S)-7,11-dihydroxy-10-(3-methyl-but-2-en-1-yl)-3-(2-methyl-benzoxazol-5-yl)-8,8,12,16-tetramethyl-4-aza-17-oxabicyclo[14.1.0]heptadecane-5,9-dione (4S,7R,8S,9S,13E/Z,16S)-4,8-dihydroxy-16-(2-methyl-benzothiazol-5-yl)-1-aza-5,5,9,13-tetramethyl-7-(prop-2-en-1-yl)-cyclohexadec-13-ene-2,6-dione (1S/R,3S,7S,10R,11R,12S,16R/S)-7,11-dihydroxy-10-
(prop-2-en-1-yl)-3-(2-methyl-benzothiazol-5-yl)-8,8,12,
16-tetramethyl-4-aza-17-oxabicyclo[14.1.0]heptadecane-
5,9-dione (4S,7R,8S,9S,13E/Z,16S)-4,8-dihydroxy-16-(2-methyl-
benzothiazol-5-yl)-1-aza-5,5,9,13-tetramethyl-7-(prop-2-
in-1-yl)-cyclohexadec-13-ene-2,6-dione (1S/R,3S,7S,10R,11R,2S,16R/S)-7,11-dihydroxy-10-(prop-
2-in-1-yl)-3-(2-methyl-benzothiazol-5-yl)-8,8,12,16-tet-
ramethyl-4-aza-17-oxabicyclo[14.1.0]heptadecane-5,9-
dione (4S,7R,8S,9S,13E/Z,16S)-418-dihydroxy-16-(2-methyl-
benzothiazol-5-yl)-1-aza-5,5,9,13-tetramethyl-7-(but-3-
en-1-yl)-cyclohexadec-13-ene-2,6-dione (1S/R,3S,7S,10R,11R,12S,16R/S)-7,11-dihydroxy-10-(but-
3-en-1-yl)-3-(2-methyl-benzothiazol-5-yl)-8,8,12,16-tet-
ramethyl-4-aza-17-oxabicyclo[14.1.0]heptadecane-5,9-
dione (4S,7R,8S,9S,13E/Z,16S)-4,8-dihydroxy-16-(2-methyl-
benzothiazol-5-yl)-1-aza-5,5,9,13-tetramethyl-7-(but-3-
in-1-yl)-cyclohexadec-13-ene-2,6-dione (1S/R,3S,7S,10R,11R,12S,16R/S)-7,11-dihydroxy-10-(but-
3-in-1-yl)-3-(2-methyl-benzothiazol-5-yl)-8,8,12,16-tet-
ramethyl-4-aza-17-oxabicyclo[14.1.0]heptadecane-5,9-
dione (4S,7R,8S,9S,13E/Z,16S)-4,8-dihydroxy-16-(2-methyl-
benzothiazol-5-yl)-1-aza-5,5,9,13-tetramethyl-7-(3-me-
thyl-but-2-en-1-yl)-cyclohexadec-13-ene-2,6-dione (1S/R,3S,7S,10R,11R,12S,16R/S)-7,11-dihydroxy-10-(3-
methyl-but-2-en-1-yl)-3-(2-methyl-benzothiazol-5-yl)-8,
8,12,16-tetramethyl-4-aza-17-oxabicyclo[14.1.0]hepta-
decane-5,9-dione (4S,7R,8S,9S,13E/Z,16S)-4,8-dihydroxy-16-(quinolin-7-
yl)-1-aza-5,5,9,13-tetramethyl-7-(prop-2-en-1-yl)-cyclo-
hexadec-13-ene-2,6-dione (1S/R,3S,7S,10R,11R,12S,16RS)-7,11-dihydroxy-10-
(prop-2-en-1-yl)-3-(quinolin-7-yl)-8,8,12,16-tetramethyl-
4-aza-17-oxabicyclo[14.1.0]heptadecane-5,9-dione (4S,7R,8S,9S,13E/Z,16S)-4,8-dihydroxy-16-(quinolin-7-
yl)-1-aza-5,5,9,13-tetramethyl-7-(prop-2-in-1-yl)-cyclo-
hexadec-13-ene-2,6-dione (1S/R,3S,7S,10R,11R,12S,16R/S)-7,11-dihydroxy-10-
(prop-2-in-1-yl)-3-(quinolin-7-yl)-8,8,12,16-tetramethyl-
4-aza-17-oxabicyclo[14.1.0]heptadecane-5,9-dione (4S,7R,8S,9S,13E/Z,16S)-4,8-dihydroxy-16-(quinolin-7-
yl)-11-aza-5,5,9,13-tetramethyl-7-(but-3-en-1-yl)-cyclo-
hexadec-13-ene-2,6-dione (1S/R,3S,7S,10R,11R,12S,16R/S)-7,11-dihydroxy-10-(but-
3-en-1-yl)-3-(quinolin-7-yl)-8,8,12,16-tetramethyl-4-aza-
17-oxabicyclo[14.1.0]heptadecane-5,9-dione (4S,7R,8S,9S,13E/Z,16S)-4,8-dihydroxy-16-(quinolin-7-
yl)-1-aza-5,5,9,13-tetramethyl-7-(but-3-in-1-yl)-cyclo-
hexadec-13-ene-2,6-dione (1S/R,3S,7S,10R,11R,12S,16R/S)-7,11-dihydroxy-10-(but-
3-in-1-yl)-3-(quinolin-7-yl)-8,8,12,16-tetramethyl-4-aza-
17-oxabicyclo[14.1.0]heptadecane-5,9-dione (4S,7R,8S,9S,13E/Z,16S)-4,8-dihydroxy-16-(quinolin-7-
yl)-1-aza-5,5,9,13-tetramethyl-7-(3-methyl-but-2-en-1-
yl)-cyclohexadec-13-ene-2,6-dione (1S/R,3S,7S,10R,11R,12S,16R/S)-7,11-dihydroxy-10-(3-
methyl-but-2-en-1-yl)-3-(quinolin-7-yl)-8,8,12,16-tet-
ramethyl-4-aza-17-oxabicyclo[14.1.0]heptadecane-5,9-
dione (4S,7R,8S,9S,13E/Z,16S(E))-4,8-dihydroxy-16-(1-methyl-
2-(2-pyridyl)ethenyl)-1-aza-5,5,9,13-tetramethyl-7-(but-
3-in-1-yl)-cyclohexadec-13-ene-2,6-dione (1S/R,3S(E),7S,10R,11R,12S,16R/S)-7,11-dihydroxy-10-
(but-3-in-1-yl)-3-(1-methyl-2-(2-pyridyl)ethenyl)-8,8,12,
16-tetramethyl-4-aza-17-oxabicyclo[14.1.0]heptadecane-
5,9-dione (4S,7R,8S,9S,13E/Z,16S(E))-4,8-dihydroxy-16-(2-(2-py-
ridyl)ethenyl)-1-aza-5,5,9,13-tetramethyl-7-(but-3-in-1-
yl)-cyclohexadec-13-ene-2,6-dione (1S/R,3S(E),7S,10R,11R,12S,16R/S)-7,11-dihydroxy-10-
(but-3-in-1-yl)-3-(2-(2-pyridyl)ethenyl)-8,8,12,16-tet-
ramethyl-4-aza-17-oxabicyclo[14.1.10]heptadecane-5,9-
dione (4S,7R,8S,9S,13E/Z,16S(E))-4,8-dihydroxy-16-(1-fluoro-
2-(2-pyridyl)ethenyl)-1-aza-5,5,9,13-tetramethyl-7-(but-
3-in-1-yl)-cyclohexadec-13-ene-2,6-dione (1S/R,3S(E),7S,10R,11R,12S,16R/S)-7,11-dihydroxy-10-
(but-3-in-1-yl)-3-(1-fluoro-2-(2-pyridyl)ethenyl)-8,8,12,
16-tetramethyl-4-aza-17-oxabicyclo[14.1.0]heptadecane-
5,9-dione (4S,7R,8S,9S,13E/Z,16S(E))-4,8-dihydroxy-16-(1-chloro-
2-(2-pyridyl)ethenyl)-1-aza-5,5,9,13-tetramethyl-7-(but-
3-in-1-yl)-cyclohexadec-13-ene-2,6-dione (1S/R,3S(E),7S,10R,11R,12S,16R/S)-7,11-dihydroxy-10-
(but-3-in-1-yl)-3-(1-chloro-2-(2-pyridyl)ethenyl)-8,8,12,
16-tetramethyl-4-aza-17-oxabicyclo[14.1.0]heptadecane-
5,9-dione (4S,7R,8S,9S,13E/Z,16S(E))-4,8-dihydroxy-16-(1-methyl-
2-(2-pyridyl)ethenyl)-1-aza-5,5,9,13-tetramethyl-7-(but-
3-en-1-yl)-cyclohexadec-13-ene-2,6-dione (1S/R,3S(E),7S,10R,11R,12S,16R/S)-7,11-dihydroxy-10-
(but-3-en-1-yl)-3-(1-methyl-2-(2-pyridyl)ethenyl)-8,8,
12,16-tetramethyl-4-aza-17-oxabicyclo[14.1.0]heptade-
cane-5,9-dione (4S,7R,8S,9S,13E/Z,16S(E))-4,8-dihydroxy-16-(2-(2-py-
ridyl)ethenyl)-1-aza-5,5,9,13-tetramethyl-7-(but-3-en-1-
yl)-cyclohexadec-13-ene-2,6-dione (1S/R,3S(E),7S,10R,11R,12S,16R/S)-7,11-dihydroxy-10-
(but-3-en-1-yl)-3-(2-(2-pyridyl)ethenyl)-8,8,12,16-tet-
ramethyl-4-aza-17-oxabicyclo[14.1.0]heptadecane-5,9-
dione (4S,7R,8S,9S,13E/Z,16S(E))-4,8-dihydroxy-16-(1-fluoro-
2-(2-pyridyl)ethenyl)-1-aza-5,5,9,13-tetramethyl-7-(but-
3-en-1-yl)-cyclohexadec-13-ene-2,6-dione (1S/R,3S(E),7S,10R,11R,12S,16R/S)-7,11-dihydroxy-10-
(but-3-en-1-yl)-3-(1-fluoro-2-(2-pyridyl)ethenyl)-8,8,12,
16-tetramethyl-4-aza-17-oxabicyclo[14.1.0]heptadecane-
5,9-dione (4S,7R,8S,9S,13E/Z,16S(E))-4,8-dihydroxy-16-(1-chloro-
2-(2-pyridyl)ethenyl)-1-aza-5,5,9,13-tetramethyl-7-(but-
3-en-1-yl)-cyclohexadec-13-ene-2,6-dione (1S/R,3S(E),7S,10R,11R,12S,16R/S)-7,11-dihydroxy-10-
(but-3-en-1-yl)-3-(1-chloro-2-(2-pyridyl)ethenyl)-8,8,12,
16-tetramethyl-4-aza-17-oxabicyclo[14.1.0]heptadecane-
5,9-dione (4S,7R(RS),8S,9S,13E/Z,16S(E))-4,8-dihydroxy-16-(1-me-
thyl-2-(2-pyridyl)ethenyl)-1-aza-5,5,9,13-tetramethyl-7-
(2-oxacyclopropyl-1-ethyl)-cyclohexadec-13-ene-2,6-di-
one (1S/R,3S(E),7S,10R(RS),11R,12S,16R/S)-7,11-dihydroxy-
10-(2-oxacyclopropyl-1-ethyl)-3-(1-methyl-2-(2-pyridyl)
ethenyl)-8,8,12,16-tetramethyl-4-aza-17-oxabicyclo
[14.1.0]heptadecane-5,9-dione (4S,7R(RS),8S,9S,13E/Z,16S(E))-4,8-dihydroxy-16-(2-(2-
pyridyl)ethenyl)-1-aza-5,5,9,13-tetramethyl-7-(2-oxacy-
clopropyl-1-ethyl)-cyclohexadec-13-ene-2,6-dione (1S/R,3S(E),7S,10R(RS),11R,12S,16R/S)-7,11-dihydroxy-
   10-(2-oxacyclopropyl-1-ethyl)-3-(2-(2-pyridyl)ethenyl)-
   8,8,12,16-tetramethyl-4-aza-17-oxabicyclo[14.1.0]hepta-
   decane-5,9-dione
(4S,7R(RS),8S,9S,13E/Z,16S(E))-4,8-dihydroxy-16-(1-
   fluoro-2-(2-pyridyl)ethenyl)-1-aza-5,5,9,13-tetramethyl-
   7-(2-oxacyclopropyl-1-ethyl)-cyclohexadec-13-ene-2,6-
   dione
(1S/R,3S(E),7S,1R(RS),11R,12S,16R/S)-7,11-dihydroxy-
   10-(2-oxacyclopropyl-1-ethyl)-3-(1-fluoro-2-(2-pyridyl)
   ethenyl)-8,8,12,16-tetramethyl-4-aza-17-oxabicyclo
   [14.1.0]heptadecane-5,9-dione
(4S,7R(RS),8S,9S,13E/Z,16S(E))-4,8-dihydroxy-16-(1-
   chloro-2-(2-pyridyl)ethenyl)-1-aza-5,5,9,13-tetramethyl-
   7-(2-oxacyclopropyl-1-ethyl)-cyclohexadec-13-ene-2,6-
   dione
(1S/R,3S(E),7S,10R(RS),11R,12S,16R/S)-7,11-dihydroxy-
   10-(2-oxacyclopropyl-1-ethyl)-3-(1-chloro-2-(2-pyridyl)
   ethenyl)-8,8,12,16-tetramethyl-4-aza-17-oxabicyclo
   [14.1.0]heptadecane-5,9-dione
(4S,7R,8S,9S,13E/Z,16S(E))-4,8-dihydroxy-16-(1-methyl-
   2-(2-pyridyl)ethenyl)-1-aza-5,5,9,13-tetramethyl-7-
   (prop-2-in-1-yl)-cyclohexadec-13-ene-2,6-dione
(1S/R,3S(E),7S,10R,11R,12S,16R/S)-7,11-dihydroxy-10-
   (prop-2-in-1-yl)-3-(1-methyl-2-(2-pyridyl)ethenyl)-8,8,
   12,16-tetramethyl-4-aza-17-oxabicyclo[14.1.0]heptade-
   cane-5,9-dione
(4S,7R,8S,9S,13E/Z,16S(E))-4,8-dihydroxy-16-(2-(2-py-
   ridyl)ethenyl)-1-aza-5,5,9,13-tetramethyl-7-(prop-2-in-1-
   yl)-cyclohexadec-13-ene-2,6-dione
(1S/R,3S(E),7S,10R,11R,12S,16R/S)-7,11-dihydroxy-10-
   (prop-2-in-1-yl)-3-(2-(2-pyridyl)ethenyl)-8,8,12,16-tet-
   ramethyl-4-aza-17-oxabicyclo[14.1.0]heptadecane-5,9-
   dione
(4S,7R,8S,9S,13E/Z,16S(E))-4,8-dihydroxy-16-(1-fluoro-
   2-(2-pyridyl)ethenyl)-1-aza-5,5,9,13-tetramethyl-7-
   (prop-2-in-1-yl)-cyclohexadec-13-ene-2,6-dione
(1S/R,3S(E),7S,10R,11R,12S,16R/S)-7,11-dihydroxy-10-
   (prop-2-in-1-yl)-3-(1-fluoro-2-(2-pyridyl)ethenyl)-8,8,
   12,16-tetramethyl-4-aza-17-oxabicyclo[14.1.0]heptade-
   cane-5,9-dione
(4S,7R,8S,9S,13E/Z,16S(E))-4,8-dihydroxy-16-(1-chloro-
   2-(2-pyridyl)ethenyl)-1-aza-5,5,9,13-tetramethyl-7-
   (prop-2-in-1-yl)-cyclohexadec-13-ene-2,6-dione
(1S/R,3S(E),7S,10R,11R,12S,16R/S)-7,11-dihydroxy-10-
   (prop-2-in-1-yl)-3-(1-chloro-2-(2-pyridyl)ethenyl)-8,8,
   12,16-tetramethyl-4-aza-17-oxabicyclo[14.1.0]heptade-
   cane-5,9-dione
(4S,7R,8S,9S,13E/Z,16S(E))-4,8-dihydroxy-16-(1-methyl-
   2-(2-pyridyl)ethenyl)-1-aza-5,5,9,13-tetramethyl-7-
   (prop-2-en-1-yl)-cyclohexadec-13-ene-2,6-dione
(1S/R,3S(E),7S,10R,11R,12S,16R/S)-7,11-dihydroxy-10-
   (prop-2-en-1-yl)-3-(1-methyl-2-(2-pyridyl)ethenyl)-8,8,
   12,16-tetramethyl-4-aza-17-oxabicyclo[14.1.10]heptade-
   cane-5,9-dione
(4S,7R,8S,9S,13E/Z,16S(E))-4,8-dihydroxy-16-(2-(2-py-
   ridyl)ethenyl)-1-aza-5,5,9,13-tetramethyl-7-(prop-2-en-
   1-yl)-cyclohexadec-13-ene-2,6-dione
(1S/R,3S(E),7S,10R,11R,12S,16R/S)-7,11-dihydroxy-10-
   (prop-2-en-1-yl)-3-(2-(2-pyridyl)ethenyl)-8,8,12,16-tet-
   ramethyl-4-aza-17-oxabicyclo[14.1.0]heptadecane-5,9-
   dione
(4S,7R,8S,9S,13E/Z,16S(E))-4,8-dihydroxy-16-(1-fluoro-
   2-(2-pyridyl)ethenyl)-1-aza-5,5,9,13-tetramethyl-7-
   (prop-2-en-1-yl)-cyclohexadec-13-ene-2,6-dione
(1S/R,3S(E),7S,10R,11R,12S,16R/S)-7,11-dihydroxy-10-
   (prop-2-en-1-yl)-3-(1-fluoro-2-(2-pyridyl)ethenyl)-8,8,
   12,16-tetramethyl-4-aza-17-oxabicyclo[14.1.0]heptade-
   cane-5,9-dione
(4S,7R(RS),8S,9S,13E/Z,16S(E))-4,8-dihydroxy-16-(1-chloro-
   2-(2-pyridyl)ethenyl)-1-aza-5,5,9,13-tetramethyl-7-
   (prop-2-en-1-yl)-cyclohexadec-13-ene-2,6-dione
(1S/R,3S(E),7S,10R,11R,12S,16R/S)-7,11-dihydroxy-10-
   (prop-2-en-1-yl)-3-(1-chloro-2-(2-pyridyl)ethenyl)-8,8,
   12,16-tetramethyl-4-aza-17-oxabicyclo[14.1.0]heptade-
   cane-5,9-dione
(4S,7R(RS),8S,9S,13E/Z,16S(E))-4,8-dihydroxy-16-(1-me-
   thyl-2-(2-pyridyl)ethenyl)-1-aza-5,5,9,13-tetramethyl-7-
   (oxacyclopropylmethyl)-cyclohexadec-13-ene-2,6-dione
(1S/R,3S(E),7S,10R(RS),11R,12S,16R/S)-7,11-dihydroxy-
   10-(oxacyclopropylmethyl)-3-(1-methyl-2-(2-pyridyl)
   ethenyl)-    8,8,12,16-tetramethyl-4-aza-17-oxabicyclo
   [14.1.0]heptadecane-5,9-dione
(4S,7R(RS),8S,9S,13E/Z,16S(E))-4,8-dihydroxy-16-(2-(2-
   pyridyl)ethenyl)-1-aza-5,5,9,13-tetramethyl-7-(oxacyclo-
   propylmethyl)-cyclohexadec-13-ene-2,6-dione
(1S/R,3S(E),7S,10R(RS),11R,12S,16R/S)-7,11-dihydroxy-
   10-(oxacyclopropylmethyl-3-(2-(2-pyridyl)ethenyl)-8,8,
   12,16-tetramethyl-4-aza-17-oxabicyclo[14.1.0]heptade-
   cane-5,9-dione
(4S,7R(RS),8S,9S,13E/Z,16S(E))-4,8-dihydroxy-16-(1-
   fluoro-2-(2-pyridyl)ethenyl)-1-aza-5,5,9,13-tetramethyl-
   7-(oxacyclopropylmethyl)-cyclohexadec-13-ene-2,6-di-
   one
(1S/R,3S(E),7S,10R(RS),11R,12S,16R/S)-7,11-dihydroxy-
   10-(oxacyclopropylmethyl)-3-(1-fluoro-2-(2-pyridyl)
   ethenyl)-8,8,12,16-tetramethyl-4-aza-17-oxabicyclo
   [14.1.0]heptadecane-5,9-dione
(4S,7R(RS),8S,9S,13E/Z,16S(E))-4,8-dihydroxy-16-(1-
   chloro-2-(2-pyridyl)ethenyl)-1-aza-5,5,9,13-tetramethyl-
   7-(oxacyclopropylmethyl)-cyclohexadec-13-ene-2,6-di-
   one
(1S/R,3S(E),7S,10R(RS),11R,12S,16R/S)-7,11-dihydroxy-
   10-(oxacyclopropylmethyl)-3-(1-chloro-2-(2-pyridyl)
   ethenyl)-8,8,12,16-tetramethyl-4-aza-17-oxabicyclo
   [14.1.0]heptadecane-5,9-dione
(4S,7R,8S,9S,13E/Z,16S(E))-4,8-dihydroxy-16-(1-methyl-
   2-(2-methylthiazol-4-yl)ethenyl)-1-aza-5,5,9,13-tetram-
   ethyl-7-(but-3-in-1-yl)-cyclohexadec-13-ene-2,6-dione
(1S/R,3S(E),7S,10R,11R,12S,16R/S)-7,11-dihydroxy-10-
   (but-3-in-1-yl)-3-(1-methyl-2-(2-methylthiazol-4-yl)
   ethenyl)-8,8,12,16-tetramethyl-4-aza-17-oxabicyclo
   [14.1.0]heptadecane-5,9-dione
(4S,7R,8S,9S,13E/Z,16S(E))-4,8-dihydroxy-16-(2-(2-meth-
   ylthiazol-4-yl)ethenyl)-1-aza-5,5,9,13-tetramethyl-7-
   (but-3-in-1-yl)-cyclohexadec-13-ene-2,6-dione
(1S/R,3S(E),7S,10R,11R,12S,16R/S)-7,11-dihydroxy-10-
   (but-3-in-1-yl)-3-(2-(2-methylthiazol-4-yl)ethenyl)-8,8,
   12,16-tetramethyl-4-aza-17-oxabicyclo[14.1.0]heptade-
   cane-5,9-dione
(4S,7R,8S,9S,13E/Z,16S(E))-4,8-dihydroxy-16-(1-fluoro-
   2-(2-methylthiazol-4-yl)ethenyl)-1-aza-5,5,9,13-tetram-
   ethyl-7-(but-3-in-1-yl)-cyclohexadec-13-ene-2,6-dione
(1S/R,3S(E),7S,10R,11R,12S,16R/S)-7,11-dihydroxy-10-
   (but-3-in-1-yl)-3-(1-fluoro-2-(2-methylthiazol-4-yl)ethe-
   nyl)-8,8,12,16-tetramethyl-4-aza-17-oxabicyclo[14.1.0]
   heptadecane-5,9-dione
(4S,7R,8S,9S,13E/Z,16S(E))-4,8-dihydroxy-16-(1-chloro-
   2-(2-methylthiazol-4-yl)ethenyl)-1-aza-5,5,9,13-tetram-
   ethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-aza-5,5,9,13-tetramethyl-7-(but-3-en-1-yl)-cyclohexadec-13-ene-2,6-dione (1S/R,3S(E),7S,1R,11R,12S,16R/S)-7,11-dihydroxy-10-(but-3-en-1-yl)-3-(1-methyl-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methylthiazol-4-yl)-ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-fluoro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-methyl-2-(2-methylthiazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-methyl-2-(2-methylthiazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(2-(2-methylthiazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(2-(2-methylthiazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-fluoro-2-(2-methylthiazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-fluoro-2-(2-methylthiazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-chloro-2-(2-methylthiazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-methyl-2-(2-methylthiazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-methyl-2-(2-methythiazol-4-yl)ethenyl-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(2-(2-methylthiazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-methylthiazol-4-yl)

ethenyl)-8,8,12,16-tetramethyl-4-aza-17-oxabicyclo [14.1.0]heptadecane-5,9-dione (4S,7R(RS),8S,9S,13E/Z,16S(E))-4,8-dihydroxy-16-(1-fluoro-2-(2-methylthiazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-methylthiazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-chloro-2-(2-methylthiazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-aza-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-aza-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-aza-5,5,9,13-tetramethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-chloro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-aza-5,5,9,13-tetramethyl-7-(but-3-en-1-yl)-cyclohexadec-13-ene-2,6-dione (1S/R,3S(E),7S,10R,11R,12S,16R/S)-7,11-dihydroxy-10-(but-3-en-1-yl)-3-(1-chloro-2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-methyl-2-(2-methyloxazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(2-(2-methyloxazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-fluoro-2-(2-methyloxazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-chloro-2-(2-methyloxazol-4-yl)ethenyl)-1-aza-5,5,9,13-tetramethyl-7-(2-oxacyclopropyl-1-ethyl)-cyclohexadec-13-ene-2,6-dione (1S/R,3S(E),7S,10R(RS),11R,12S,16R/S)-7,11-dihydroxy-10-(2-oxacyclopropyl-1-ethyl)-3-(1-chloro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-aza-5,5,9,13-tetramethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-chloro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-aza-5,5,9,13-tetramethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-chloro-2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-methyl-2-(2-methyloxazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(2-(2-methyloxazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-fluoro-2-(2-methyloxazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R(RS),8S,9S,13E/Z,16S(E))-4,8-dihydroxy-16-(1-chloro-2-(2-methyloxazol-4-yl)ethenyl)-1-aza-5,5,9,13-tetramethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-aza-5,5-trimethylene-9,13-dimethyl-7-(but-3-in-1-yl)-cyclohexadec-13-ene-2,6-dione (1S/R,3S(E),7S,10R,11R,12S,16R/S)-7,11-dihydroxy-10-(but-3-in-1-yl)-3-(1-methyl-2-(2-pyridyl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-aza-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-pyridyl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-aza-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-pyridyl)ethenyl)-8,8-trimethylene-12,16-dimethyl-4-aza-17-oxabicyclo[14.1.0]heptadecane-5,9-dione (4S,7R(RS),8S,9S,13E/Z,16S(E))-4,8-dihydroxy-16-(1-fluoro-2-(2-pyridyl)ethenyl)-1-aza-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-pyridyl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-aza-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-methyl-2-(2-methylthiazol-4-yl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-aza-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methylthiazol-4-yl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-aza-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(2-(2-methylthiazol-4-yl)ethenyl)-8,8-trimethylene-12,16-dimethyl-4-aza-17-oxabicyclo[14.1.0]heptadecane-5,9-dione (4S,7R(RS),8S,9S,13E/Z,16S(E))-4,8-dihydroxy-16-(1-fluoro-2-(2-methylthiazol-4-yl)ethenyl)-1-aza-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-fluoro-2-(2-methylthiazol-4-yl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-aza-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(2-(2-methyloxazol-4-yl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5-trimethylene-9,13-dimethyl-7-(prop-2-in-1-yl)-cyclohexadec-13-ene-2,6-dione (1S/R,3S(E),7S,10R,11R,12S,16R/S)-7,11-dihydroxy-10-(prop-2-in-1-yl)-3-(1-fluoro-2-(2-methyloxazol-4-yl)

ethenyl)-8,8-trimethylene-12,16-dimethyl-4-aza-17-ox-abicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-aza-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-methyl-2-(2-methyloxazol-4-yl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5-trimethylene-9,13-dimethyl-7-(prop-2-en-1-yl)-cyclohexadec-13-ene-2,6-dione (1S/R,3S(E),7S,10R,11R,12S,16R/S)-7,11-dihydroxy-10-(prop-2-en-1-yl)-3-(1-fluoro-2-(2-methyloxazol-4-yl)ethenyl)-8,8-trimethylene-12-16-dimethyl-4-aza-17-oxabicyclo[14.1.0]heptadecane-5,9-dione (4S,7R(RS),8S,9S,13E/Z,16S(E))-4,8-dihydroxy-16-(2-(2-methyloxazol-4-yl)ethenyl)-1-aza-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(2-(2-methyloxazol-4-yl)ethenyl)-8,8-trimethylene-12,16-dimethyl-4-aza-17-oxabicyclo[14.1.0]heptadecane-5,9-dione (4S,7R(RS),8S,9S,13E/Z,16S(E))-4,8-dihydroxy-16-(1-chloro-2-(2-methyloxazol-4-yl)ethenyl)-1-aza-5,5-trimethylene-9,13-dimethyl-7-(oxacyclopropylmethyl)-cyclohexadec-13-ene-2,6-dione (1S/R,3S(E),7S,10R(RS),11R,12S,16R/S)-7,11-dihydroxy-10-(oxacyclopropylmethyl)-3-(1-chloro-2-(2-methyloxazol-4-yl)ethenyl)-8,8-trimethylene-12,16-dimethyl-4-aza-17-oxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-methyl-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-pyridyl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-fluoro-2-(2-pyridyl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-pyridyl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-chloro-2-(2-pyridyl)ethenyl)-8,8,12,16-tetramethyl-4,17-dioxobicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-methyl-(2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-fluoro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-chloro-2-(2-methylthiazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-methyloxazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-methyl-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-fluoro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-oxa-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-chloro-2-(2-methyloxazol-4-yl)ethenyl)-8,8,12,16-tetramethyl-4,17-dioxabicyclo[14.1.0]heptadecane-5,9-dione (4S,7R,8S,9S,13E/Z,16S(E))-4,8-dihydroxy-16-(1-methyl-2-(2-pyridyl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-methyl-2-(2-pyridyl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-pyridyl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(2-(2-pyridyl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-pyridyl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-fluoro-2-(2-pyridyl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-pyridyl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-chloro-2-(2-pyridyl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-methyl-2-(2-methylthiazol-4-yl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-methyl-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methylthiazol-4-yl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-1'-(3-methyl-but-2-en-1-yl)-3-(2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methylthiazol-4-yl)ethenyl)-1-aza-5,5,9,13-tetramethyl-7-(3-methyl-but-2-en-1-yl)-cyclohexadec-13-ene-2,6-dione (1S/R,3S(E), 7S,10R,11R,12S,16R/S)-7,11-dihydroxy-10-(3-methyl-but-2-en-1-yl)-3-(1-fluoro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methylthiazol-4-yl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-chloro-2-(2-methylthiazol-4-yl)ethenyl)-8,8,12,16-tetramethyl-4-aza-17-oxabicyclo[14.1.0]heptadecane-5,9-dione (4S,7R,8S,9S,13E/Z, 16S(E))-4,8-dihydroxy-16-(1-methyl-2-(2-methyloxazol-4-yl)ethenyl)-1-aza-5,5,9,13-tetramethyl-7-(3-methyl-but-2-en-1-yl)-cyclohexadec-13-ene-2,6-dione (1S/R,3S(E), 7S,10R,11R,12S,16R/S)-7,11-dihydroxy-10-(3-methyl-but-2-en-1-yl)-3-(1-methyl-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(2-(2-methyloxazol-4-yl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-fluoro-2-(2-methyloxazol-4-yl)ethenyl)-1-aza-5,5,9,13-tetramethyl-7-(3-methyl-but-2-en-1-yl)-cyclohexadec-13-ene-2,6-dione (1S/R,3S(E),7S,10R,11R,12S,16R/S)-7,11-dihydroxy-10-(3-methyl-but-2-en-1-yl)-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13E/Z,16S(E))-4,8-dihydroxy-16-(1-chloro-2-(2-methyloxazol-4-yl)ethenyl)-1-aza-5,5,9,13-tetramethyl-7-(3-methyl-but-2-en-1-yl)-cyclohexadec-13-ene-2,6-dione (1S/R,3S(E),7S,11R,11R,12S,16R/S)-7,11-dihydroxy-10-(3-methyl-but-2-en-1-yl)-3-(1-chloro-2-(2-methyloxazol-4-yl)ethenyl)-8,8,12,16-tetramethyl-4-aza-17-oxabicyclo[14.1.0]heptadecane-5,9-dione Production of Partial Fragments $A_f$:

The partial fragments (synthesis components) of general formula A-1 can be produced starting from the precursors described in WO 99/07692, such as, for example, A-I. This is further explained by way of example in Diagram 1.

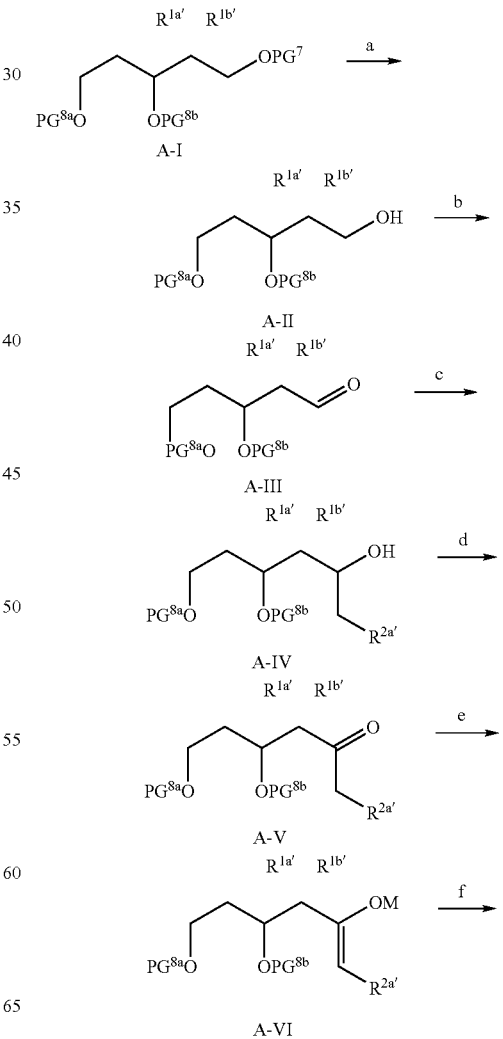

Diagram 1

-continued

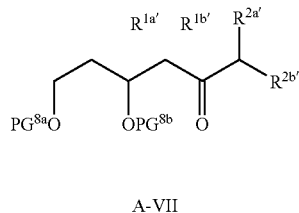

A-VII

Step a (A-I→A-II):

The hydroxyl group that is protected by $PG^7$ in A-1 is released. As protective group $PG^7$, the protective groups described above and that are known to one skilled in the art, such as, e.g., the methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triiospropylsilyl, benzyl, para-nitrobenzyl, para-methoxybenzyl, formyl, acetyl, propionyl, isopropionyl, pivalyl, butyryl or benzoyl radicals, are suitable. A survey is found in, e.g., "Protective Groups in Organic Synthesis," Theodora W. Green, John Wiley and Sons).

Preferred are those protective groups that can be cleaved under the action of fluoride, such as, e.g., the trimethylsilyl, tert-butyldimethylsilyl, tert-butyldiphenylsilyl, tribenzylsilyl, or triisopropylsilyl radical.

Especially preferred are the tert-butyldimethylsilyl radical, the triisopropylsilyl radical, and the tert-butyldiphenylsilyl radical.

As protective groups $PG^{8a}$ and $PG^{8b}$, the groups that are already mentioned for $PG^7$ and together a —$CR^{28a}R^{28b}$ group, in which $R^{28a}$ and $R^{28b}$ can be the same or different and mean hydrogen, $C_1$–$C_{10}$ alkyl, aryl, $C_7$–$C_{20}$ aralkyl, are suitable.

Preferred are those —$CR^{28a}R^{28b}$ protective groups, in which $R^{28a}$ and $R^{28b}$ mean $C_1$–$C_8$ alkyl, or $R^{28a}$ means hydrogen and $R^{28b}$ means aryl.

Especially preferred is a —$C(CH_3)_2$ group.

Protective group $PG^7$ is cleaved according to a process that is known to one skilled in the art. This is a silyl ether, thus suitable for the cleavage is the reaction with fluorides, such as, for example, tetrabutylammonium fluoride, hydrogen fluoride-pyridine complex, potassium fluoride or the use of dilute mineral acids, the use of catalytic amounts of acids, such as, e.g., para-toluenesulfonic acid, para-toluenesulfonic acid-pyridinium salt, camphorsulfonic acid in alcoholic solutions, preferably in ethanol or isopropanol.

Step b (A-II→A-III):

The oxidation of the primary alcohol in A-II to aldehyde A-III is carried out according to the methods that are known to one skilled in the art. For example, oxidation with pyridinium chlorochromate, pyridinium dichromate, chromium trioxide-pyridine complex, oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is the oxidation according to Swern, as well as with N-methyl-morpholino-N-oxide using tetrapropylammonium perruthenate.

Step c (A-III→A-IV):

The reaction of aldehydes A-III to alcohols of formula A-IV is carried out with organometallic compounds of theoretical formula M—$CHR_2R^{2a'}$, in which M stands for indium, an alkali metal, preferably lithium or a divalent metal MX, in which X represents a halogen, and radical $R^{2a'}$ has the above-mentioned meanings. As a divalent metal, magnesium and zinc are preferred; as halogen, X is preferably chlorine, bromine and iodine.

Step d (A-IV→A-V):

The oxidation of the secondary alcohol in A-IV to ketone A-V is carried out according to the conditions that are mentioned under step b). Preferred is the oxidation with N-methyl-morpholino-N-oxide with use of tetrapropylammonium perruthenate.

Step e (A-V→A-VI):

For optional introduction of a radical $R^{2b'}$, which, except for hydrogen, can have the already mentioned meanings, the ketone of general formula A-V is converted into the enolate with M in the meaning of the counter-cation with use of strong bases, such as preferably lithium diisopropylamide.

Step f (A-VI→A-VII):

The enolate of formula A-VI is reacted with a compound of general formula X—$R^{2b'}$, in which X represents a halogen or another leaving group, such as, for example, an alkylsulfonate or arylsulfonate. As halogen, X is preferably chlorine, bromide and iodine.

The partial fragments (synthesis components) of general formula A-2 can be produced by known methods, such as described in Angew. Chemie 1996, 108, 2976–2978. Another process is shown in Diagram 2:

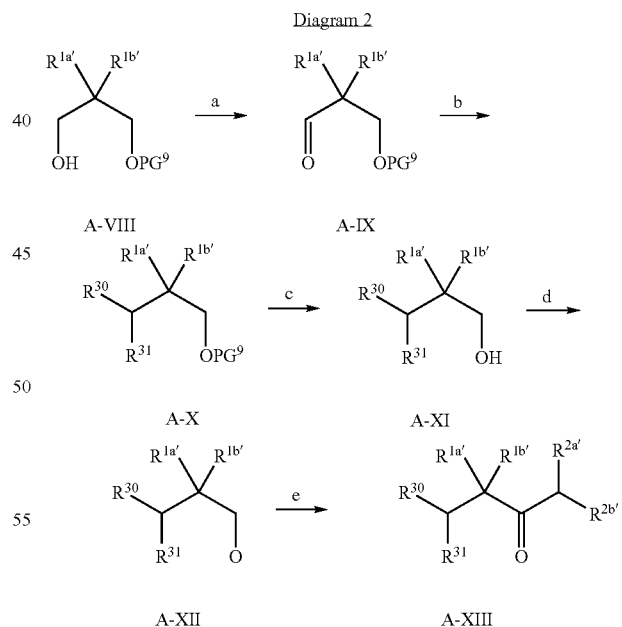

Diagram 2

Step a (A-VIII→A-IX):

The oxidation of the primary alcohol in A-VIII to aldehyde A-IX is carried out according to the methods that are described for Diagram 1, step b. The oxidation according to Swern and with N-methyl-morpholino-N-oxide with use of tetrapropylammonium perruthenate is preferred.

Step b (A-IX→A-X):

The carbonyl group in A-IX can optionally be converted into a ketal according to the methods that are known to one skilled in the art.

Step c (A-X→A-XI):

The hydroxyl group that is protected in A-X by $PG^9$ is released. As protective group $PG^9$, the protective groups that are described under Diagram 1, step a are suitable. Preferred are those protective groups that can be cleaved under the action of fluoride, such as, e.g., the trimethylsilyl, tert-butyldimethylsilyl, tert-butyldiphenylsilyl, tribenzylsilyl, or triisopropylsilyl radical.

Especially preferred is the tert-butyldimethylsilyl radical, the triisopropylsilyl radical and the tert-butyldiphenylsilyl radical.

Step d (A-XI→A-XII):

The oxidation of the primary alcohol in A-IX to aldehyde A-XII is carried out according to the methods that are described for Diagram 1, step b. The oxidation according to Swern and with N-methyl-morpholino-N-oxide with use of tetrapropylammonium perruthenate is preferred.

Step e (A-XII→A-XIII):

The introduction of radicals $R^{2a'}$ and/or $R^{2b'}$ and production of ketone A-XIII are carried out as described under Diagram 1 in steps c to f.

Production of Partial Fragments $B_f$:

The partial fragments (synthesis components) of general formula $B_f$ can be produced by known methods, such as described in WO 99/07692.

Production of Partial Fragments $C_f$:

The partial fragments (synthesis components) of general formula $C_f$ can be produced as described in DE 197 51 200.3, DE 199 07 480.1 and WO 99/07692 as well as in PCT/EP00/01333 and Example 21.

Production of partial fragments $A_f$, $B_f$ and $C_f$ and their cyclization to I is also carried out analogously to what is described in WO 99/07692 for numerous epothilone derivatives, with the difference that in the known derivatives in 6-position, there is no unsaturated radical. WO 99/07692 already confirms the general usability of the synthesis principle that is described below for the compounds according to the invention. In addition, numerous synthesis components of general formulas $A_f$, $B_f$ and $C_f$ are described in WO 99/07692, with which, optionally in modified form in the case of the substitution according to the invention at carbon 6, other compounds of general formula I claimed here can be obtained. Synthesis components of general formula $C_f$, in which as $R^8$, a halogen atom, especially a fluorine, chlorine or bromine atom, is present, are the subject of DE 199 07 480.1 as well as PCT/EP00/01333.

Partial fragments of general formula AB

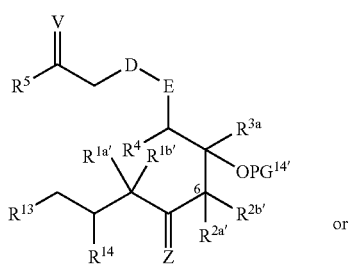

AB-1 or

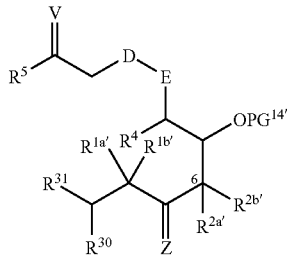

AB-2 in which $R^{1a'}$, $R^{1b'}$, $R^{2a'}$, $R^{2b'}$, $R^{3a'}$, $R^4$, $R^5$, $R^{13}$, $R^{14}$, $R^{30}$, $R^{31}$, V and Z have the already mentioned meanings, and $PG^{14'}$ represents a hydrogen atom or a protective group PG, can be obtained from the above-mentioned fragments $A_f$ and $B_f$ according to the process that is shown in Diagram 3.

Diagram 3

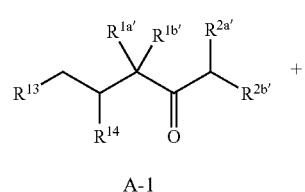

A-1

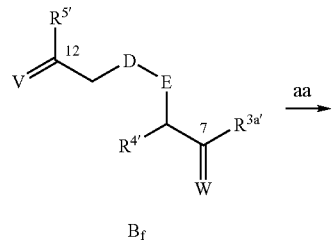

$B_f$

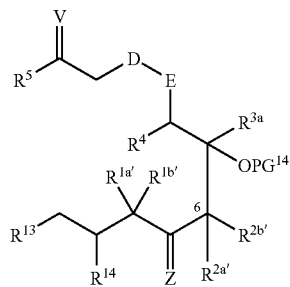

AB-1

-continued

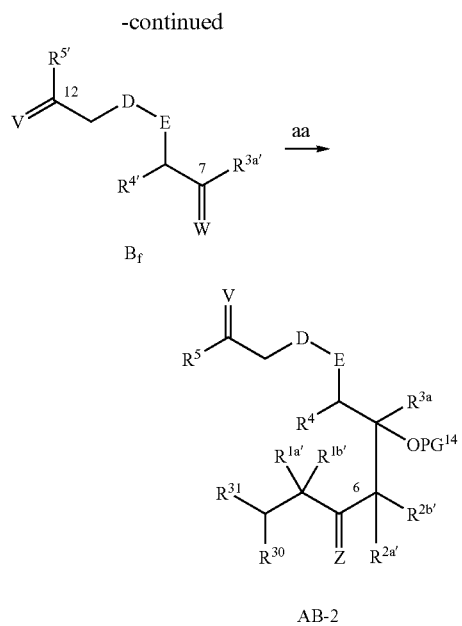

AB-2

Step aa ($A_f + B_f \rightarrow AB$):

Compound $B_f$, in which W has the meaning of an oxygen atom and optionally present additional carbonyl groups are protected, is alkylated with the enolate of a carbonyl compound of general formula $A_f$. The enolate is produced by action of strong bases, such as, e.g., lithium diisopropylamide, lithium hexamethyldisilazane at low temperatures.

Partial Fragments of General Formula BC

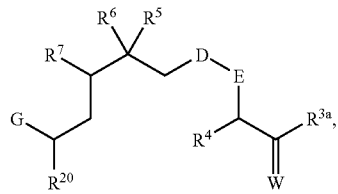

BC in which $R^{3a}$, $R^4$, $R^5$, $R^6$, $R^7$, $R^{20}$, D, E, G and W have the already mentioned meanings, are obtained from previously described fragments $B_f$ and $C_f$ according to the process that is shown in Diagram 4.

Diagram 4

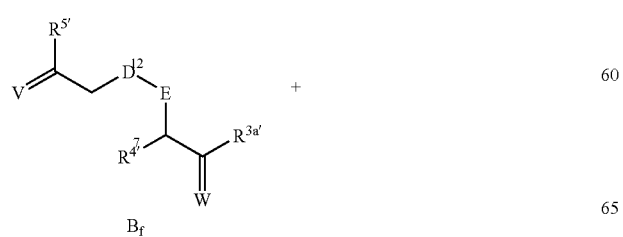

$B_f$

-continued

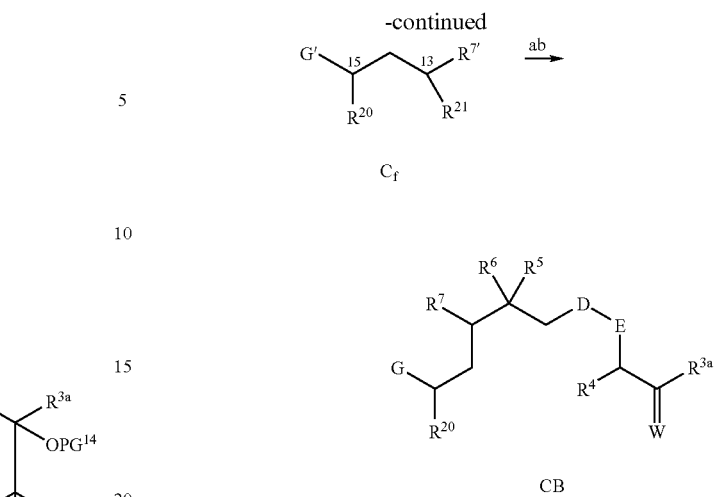

$C_f$

CB

Step ab ($B_f + C_f \rightarrow BC$):

Compound C, in which $R^{21}$ has the meaning of a Wittig salt, and optionally present additional carbonyl groups are protected, is deprotonated by a suitable base, such as, e.g., n-butyllithium, lithium diisopropylamide, potassium tert-butanolate, sodium or lithium-hexamethyldisilazide and reacted with a compound $B_f$, in which V has the meaning of oxygen, and W has the meaning of two alkoxy groups $OR^{19}$, a $C_2$–$C_{10}$-alkylene-α,ω-dioxy group, which can be straight-chain or branched or has $H/OR^{18}$.

Partial Fragments of General Formula ABC (AB+$C_f$)

ABC-1

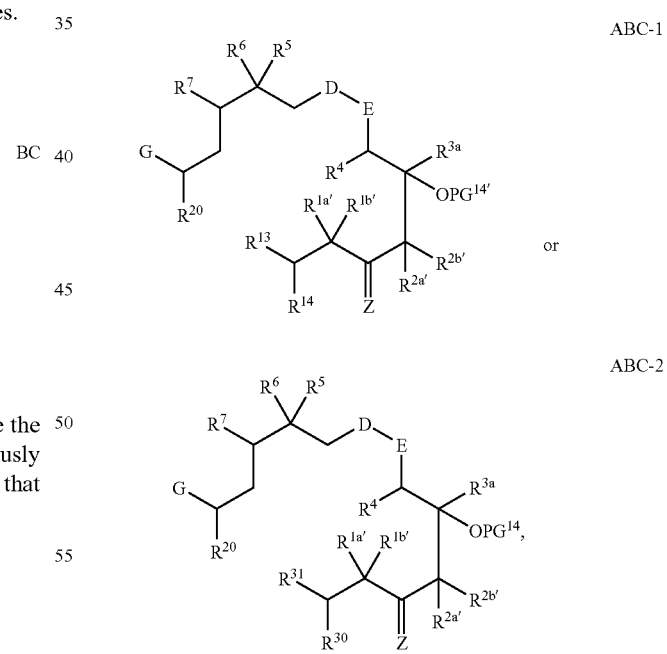

or

ABC-2 in which $R^{1a'}$, $R^{1b'}$, $R^{2a'}$, $R^{2b'}$, $R^{3a}$, $R^4$, $R^5$, $R^6$, $R^7$, $R^{13}$, $R^{14}$, $R^{30}$, $R^{31}$, D, E, G and Z have the meanings already mentioned, and $PG^{14'}$ represents a hydrogen atom or a protective group PG, are obtained from the previously described fragments AB and C according to the process that is shown in Diagram 5 and Diagram 6.

Diagram 5

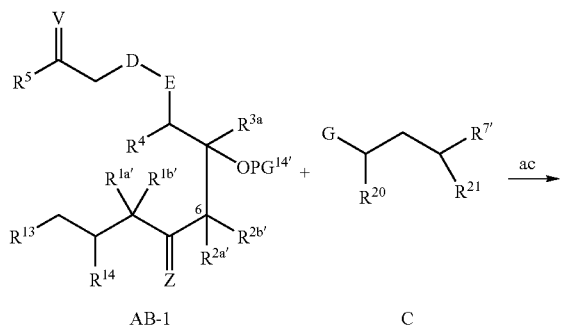

AB-1   C

ABC-1

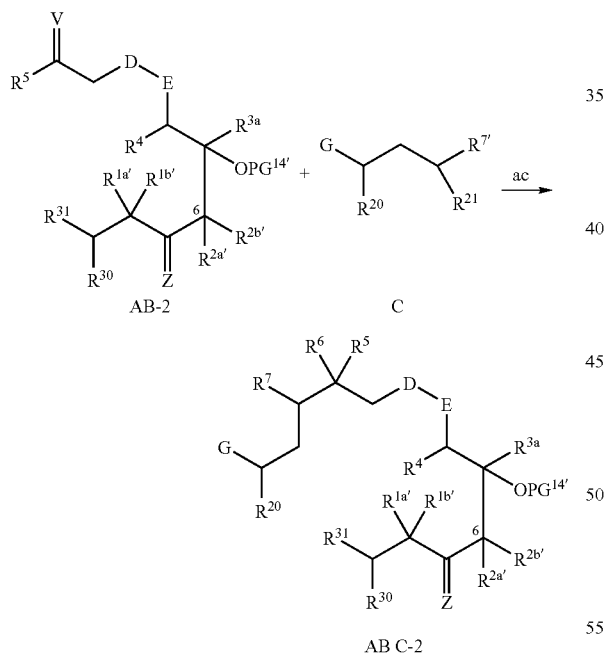

AB-2   C

AB C-2

Diagram 6

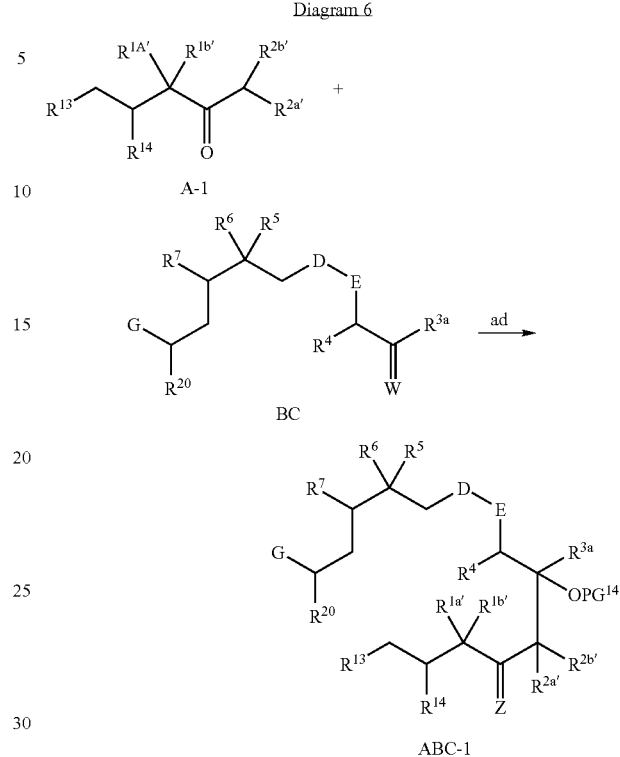

A-1

BC

ABC-1

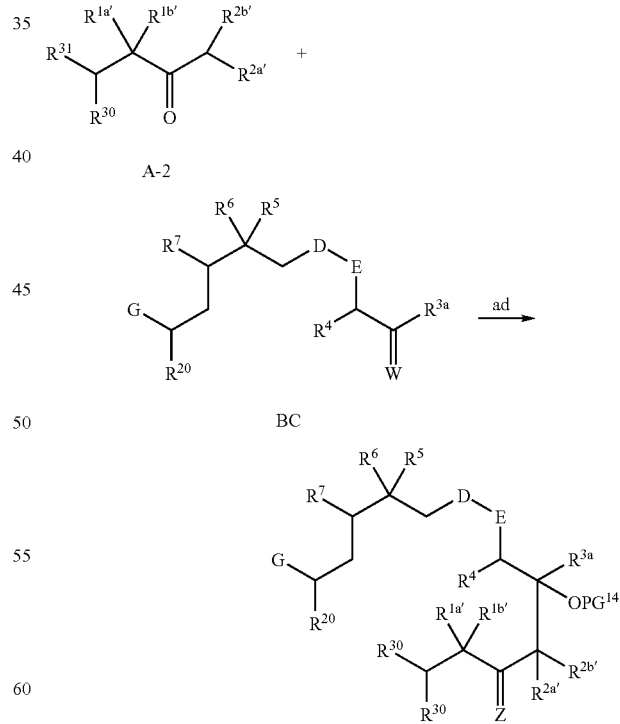

A-2

BC

ABC-2

Step ac (AB+C$_f$→ABC):

Compound C$_f$ in which R$^{21}$ has the meaning of a Wittig salt, and optionally present additional carbonyl groups are optionally protected, is deprotonated by a suitable base, such as, e.g., n-butyllithium, lithium diisopropylamide, potassium tert-butanolate, sodium or lithium-hexamethyldisilazide and reacted with a compound AB, in which V has the meaning of an oxygen atom.

Step ad ($A_f$+BC→ABC):

Compound BC, in which W has the meaning of an oxygen atom and optionally present additional carbonyl groups are protected, is alkylated with the enolate of a carbonyl compound of general formula $A_f$. The enolate is produced by action of strong bases, such as, e.g., lithium diisopropylamide, lithium hexamethyldisilazane at low temperatures.

Step ae (ABC-1→I):

Compounds ABC-1, in which $R^{13}$ represents a carboxylic acid $CO_2H$ and $R^{20}$ represents a hydroxyl group or an amino group, are reacted according to the methods that are known to one skilled in the art for the formation of large macrolides or macrolactams to compounds of formula I, in which A-Y has the meaning of an O—(C=O) group or $NR^{29}$—C(=O) group. For example, preferred for lactone formation is the method that is described in "Reagents for Organic Synthesis, Vol. 16, p. 353" with use of 2,4,6-trichlorobenzoic acid chloride and suitable bases, such as, e.g., triethylamine, 4-dimethylaminopyridine, sodium hydride. For example, preferred for the lactam formation is the reaction of the amino acid ($R^{13}$ a carboxylic acid $CO_2H$ and $R^{20}$ an $NHR^{29}$ group) with diphenylphosphorylazide in the presence of a base.

Step af (ABC-1→I):

Compounds ABC-1, in which $R^{13}$ represents a group $CH_2OH$ and $R^{20}$ represents a hydroxyl group, can be reacted preferably with use of triphenylphosphine and azodiesters, such as, for example, azodicarboxylic acid diethyl ester, to compounds of formula I, in which A-Y has the meaning of an O—$CH_2$ group.

Compounds ABC, in which $R^{13}$ represents a group $CH_2$-Hal or $CH_2OSO_2$—alkyl or $CH_2OSO_2$ aryl or $CH_2OSO_2$—aralkyl and $R^{20}$ represents a hydroxyl group, can be cyclized to compounds of formula I, in which A-Y has the meaning of an O—$CH_2$ group, after deprotonation with suitable bases, such as, for example, sodium hydride, n-butyllithium, 4-dimethylaminopyridine, Hünig base, alkylhexamethyldisilazanes.

Step ag (ABC-2→I):

Compounds ABC-2, in which $R^{30}$ and $R^{31}$ together represent an oxygen atom and $R^{20}$ represents an $NR^{29}SO_2CH_3$ group, can be cyclized at low temperatures to sulfonamide I, in which A-Y has the meaning of an $NR^{29}SO_2$ group, by action of strong bases, such as, e.g., lithium diisopropylamide, lithium hexamethyldisilazane.

Step ah (ABC-2→I):

Compounds ABC-2, in which $R^{30}$ and $R^{31'}$ together represent an oxygen atom and $R^{20}$ represents an O—C(=O)$CH_3$ group, can be cyclized at low temperatures to lactone I, in which A-Y has the meaning of an O—C(=O) group, by action of strong bases, such as, e.g., lithium diisopropylamide, or alkali hexamethyldisilazane.

Step ah (ABC-2→I):

Compounds ABC-2, in which $R^{30}$ and $R^{31}$ together represent an oxygen atom and $R^{20}$ represents a $CH_2C$(=O)$CH_3$ group, can be cyclized at low temperatures to lactone I, in which A-Y has the meaning of a $CH_2C$(=O) group by action of strong bases such as, e.g., lithium diisopropylamide, alkali hexamethyldisilazane.

Introduction of the Nitrogen Group for $R^{20}$:

Amino group $NHR^{29}$ can be introduced in the stage of the $C_f$-fragment, the BC-fragment or the ABC-fragment according to the methods that are known to one skilled in the art. Preferred is the production from the azide ($R^{20}$=$N_3$), which is first converted into the phosphaimine according to the methods that are known to one skilled in the art, preferably with use of a phosphine such as, for example, triphenylphosphine; the phosphaimine is then converted in the presence of water into the amine ($R^{20}$=$NHR^{29}$) that is optionally to be protected for the further course of reaction. The introduction of the azide can be carried out with use of the Mitsunobu reaction in the presence of metal azides, preferably sodium or tin azide or by substitution of a suitable leaving group, such as, for example, a chlorine, bromine or iodine atom, an alkylsulfonyloxy group, a perfluorinated alkylsulfonyloxy group, an arylsulfonyloxy group or an aralkylsulfonyloxy group by azides.

The flexible functionalization of described components $A_f$, $B_f$ and $C_f$ also ensures a linkage sequence that deviates from the above-described process and that leads to components ABC. These processes are listed in the following table:

| Possible Linkages | Linkage Methods a to e | Prerequisites |
| --- | --- | --- |
| $A_f + B_f \rightarrow A_f - B_f$ | a: Aldol (see Diagram 3) | Z = W = oxygen |
| $B_f + C_f \rightarrow B_f - C_f$ | b: Wittig (analogously to Diagram 4) e: McMurry | U = oxygen and $R^{21}$ = Wittig salt, phosphine oxide or phosphonate U = V = oxygen |
| $A_f + C_f \rightarrow A_f - C_f$ | C: Esterification (e.g., 2,4,6-trichlorobenzoyl chloride and 4-dimethylamino pyridine) | $R^{13}$ = $CO_2R^{13b}$ or COHal and $R^{20}$ = hydroxyl |
|  | d: Etherification (e.g., according to Mitsunobu) | $R^{13}$ = $CH_2OH$ and $R^{20}$ = hydroxyl or $OSO_2$-alkyl or $OSO_2$-aryl or $OSO_2$-aralkyl |
|  | f. Amide formation (e.g., with $(PhO)_2P(O)N_3$) in the presence of a base in an inert solvent | $R^{13}$ = $CO_2R^{13b}$ or COHal and $R^{20}$ = $NHR^{29}$ |
|  | g. Ketone formation by aldol reaction with a strong base. | $R^{20}$ = $CH_2C$(=O)$CH_3$ and $R^{30}$, $R^{31}$ = oxygen |
|  | h. Sulfonamide formation in the presence of a strong base. | $R^{20}$ = $NR^{29}SO_2CH_3$ and $R^{30}$, $R^{31}$ = oxygen |
|  | i. Amide formation in the presence of a strong base. | $R^{20}$ = $NR^{29}C$(=O)$CH_3$ and $R^{30}$, $R^{31}$ = oxygen |

According to these processes, components $A_f$, $B_f$ and $C_f$ can be linked as indicated in Diagram 7:

Diagram 7

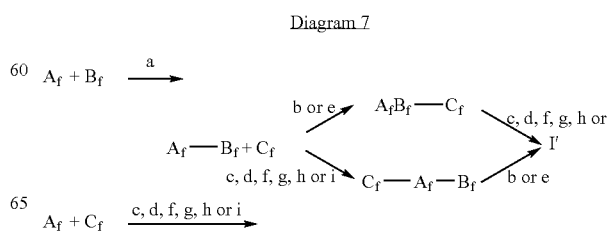

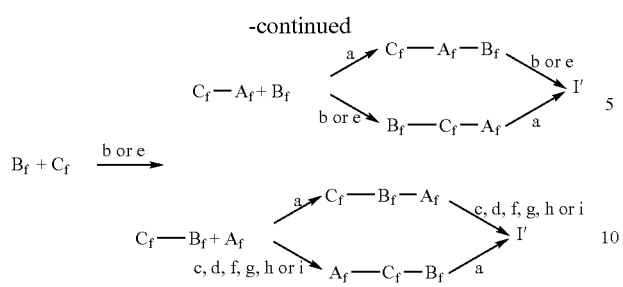

Free hydroxyl groups in I, $A_f$, $B_f$, $C_f$, AB, BC, ABC can be further functionally modified by etherification or esterification, free carbonyl groups by ketalization, enol ether formation or reduction.

The invention relates to all stereoisomers of these compounds and also mixtures thereof.

The invention also relates to all prodrug formulations of these compounds, i.e., all compounds that release in vivo a bioactive active ingredient component of general formula I.

Biological Actions and Applications of the New Derivatives:

The new compounds of formula I are valuable pharmaceutical agents. They interact with tubulin by stabilizing microtubuli that are formed and are thus able to influence the cell-splitting in a phase-specific manner. Accordingly, the compounds find use in treating diseases or conditions associated with cell growth, division and/or proliferation. They have particular application with quick-growing, neoplastic cells, whose growth is largely unaffected by intercellular regulating mechanisms. Active ingredients having properties of this type, including the compounds of this invention, are suitable for treating malignant tumors. As applications, there can be mentioned, for example, the therapy of ovarian, stomach, colon, adeno-, breast, lung, head and neck carcinomas, malignant melanoma, acute lymphocytic and myelocytic leukemia, particularly against tumors associated therewith. The compounds according to the invention are additionally suitable owing to their properties for anti-angiogenesis therapy as well as for treatment of chronic inflammatory diseases, such as, for example, psoriasis, multiple sclerosis or arthritis. The compounds of the invention have utilities analogous to those for known epothilone derivatives, discussed above, but with the advantages discussed above and below. As with the known epothilones, the new compounds can be administered for and in a manner analogous to known drugs such as Taxol, but modified to take advantage of their particular superior properties thereover.

In other embodiments, to avoid uncontrolled proliferation of cells and/or for better compatibility of medical implants, the new compounds or pharmaceutical formulations containing them can be applied or introduced into the polymer materials that are used for these purposes.

The compounds according to the invention can be used alone or in combination with other principles and classes of substances that can be used in tumor therapy to achieve additive or synergistic actions. As examples, there can be mentioned the combination with Platinum complexes, such as, e.g., cis-platinum, carboplatinum, intercalating substances, e.g., from the class of anthracyclines, such as, e.g., doxorubicin or from the class of anthrapyrazoles, such as, e.g., Cl-941, substances that interact with tubulin, e.g., from the class of vinca-alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4, discodermolide and its analogs, DNA topoisomerase inhibitors, such as, e.g., camptothecin, etoposide, topotecan, teniposide, folate- or pyrimidine-antimetabolites, such as, e.g, lometrexol, gemcitubin, DNA-alkylating compounds, such as, e.g., adozelesin, dystamycin A, inhibitors of growth factors (e.g., of PDGF, EGF, TGFb, EGF), such as, e.g., somatostatin, suramin, bombesin antagonists, inhibitors of protein tyrosine kinases or protein kinases A or C, such as, e.g., erbstatin, genistein, staurosporine, ilmofosine, 8-Cl-cAMP, antihormones from the class of antigestagens, such as, e.g., mifepristone, onapristone or from the class of antiestrogens, such as, e.g., tamoxifen or from the class of antiandrogens, such as, e.g., cyproterone acetate, metastases-inhibiting compounds, e.g., from the class of eicosanoids, such as, e.g., $PGI_2$, $PGE_1$, 6-oxo-$PGE_1$ as well as their more stable derivatives (e.g., iloprost, cicaprost, misoprostol), inhibitors of oncogenic RAS proteins, which influence the mitotic signal transduction, such as, for example, inhibitors of the farnesyl-protein-transferase, natural or synthetically produced antibodies, which are directed against factors or their receptors, which promote tumor growth, such as, for example, the erbB2 antibody.

The invention also relates to pharmaceutical agents that are based on pharmaceutically compatible compounds, i.e., compounds of general formula I that are nontoxic in the doses used, optionally together with commonly used adjuvants and vehicles.

In other embodiments, the compounds according to the invention can be encapsulated with liposomes or included in an α-, β- or γ-cyclodextrin clathrate.

According to methods of galenicals that are known in the art, the compounds according to the invention can be processed into pharmaceutical preparations for enteral, percutaneous, parenteral or local administration. They can be administered in the form of tablets; coated tablets; gel capsules; granulates; suppositories; implants; injectable, sterile, aqueous or oily solutions; suspensions or emulsions; ointments; creams and gels, for example.

In this case, the active ingredient or ingredients can be mixed with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, cleaning agents, dispersing agents, emulsifiers, preservatives and flavoring substances for taste correction (e.g., ethereal oils).

The invention thus also relates to pharmaceutical compositions that as active ingredients contain at least one compound-according to the invention. A dosage unit will preferably contain about 0.1–100 mg of active ingredient(s). In humans, the dosage of the compounds according to the invention is preferably approximately 0.1–1000 mg per day.

The examples below are used for a more detailed explanation of the invention, without intending that it be limited to these examples.

The entire disclosure of all applications, patents and publications, cited above or below, and of corresponding German application Nos. 199 21 086.1, filed 30 Apr. 1999, and 199 54 228.7, filed 4 Nov. 1999, are hereby incorporated by reference.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

Example 1

4S,7R,8S,9S,13Z,16S(E))-4,8-Dihydroxy-16-(1-methyl-2-(2-pyridyl)ethenyl)-1-oxa-5,5,9,13-tetramethyl-7-(but-3-in-1-yl)-cyclohexadec-13-ene-2,6-dione Production of (4S(4R,5S,6S,10E/Z,13S,14E))-4-(β-hydroxy-5-(tetrahydro-2H-pyran-2-yloxy)-2,6,10,14-tetramethyl-3-oxo-15-(2-pyridyl)-4-(but-3-in-1-yl)-undec-6-in-2-yl)-2,2-dimethyl-[1,3]dioxane; Variant I:

Example 1a (3RS,4S)-4-(2-Methyl-3-hydroxy-8-(trimethylsilyl)-oct-7-in-2-yl)-2,2-dimethyl-[1,3]dioxane The solution of 6.33 g (34 mmol) of (4S)-4-(2-methyl-1-oxo-prop-2-yl)-2,2-dimethyl-[1,3]dioxane, which was produced analogously to the process described in DE 197 51 200.3, in 10 ml of anhydrous tetrahydrofuran is mixed in portions under an atmosphere of dry argon with the solution of a total of 50 mmol of 5-trimethylsilyl-pent-4-in-1-yl-magnesium bromide in tetrahydrofuran, allowed to heat to 60° C. and stirred for 1.5 hours. It is poured onto water and extracted several times with ethyl acetate. The combined organic extracts are washed with water and saturated sodium chloride solution and dried on sodium sulfate. The residue that was obtained after filtration and removal of the solvent is purified by chromatography on fine silica gel with a gradient system that consists of n-hexane and ethyl acetate. 6.22 g (19 mmol, 56%) of the chromatographically separable 3R- and 3S-epimers of the title compound and 1.35 g of (4S)-4-(2-methyl-1-hydroxy-prop-2-yl)-2,2-dimethyl-[1,3]dioxane are isolated in each case as a colorless oil.

$^1$H-NMR (CDCl$_3$): δ=0.14 (9H), 0.73+0.88 (3H), 0.91 (3H), 1.28–1.93 (12H), 2.21–2.33 (2H), 3.40–3.72 (2H), 3.80–4.03 (3H) ppm.

Example 1b (4S)-4-(2-Methyl-3-oxo-8-(trimethylsilyl)-oct-7-in-2-yl)-2,2-dimethyl-[1,3]dioxane The solution of 6.22 g (19 mmol) of a mixture of the compounds, produced according to Example 1a, in 200 ml of anhydrous dichloromethane is mixed with a molecular sieve (4A, about 20 pellets), 4.01 g of N-methylmorpholino-N-oxide, 335 mg of tetrapropylammonium perruthenate and stirred for 16 hours at 23° C. under an atmosphere of dry argon. It is concentrated by evaporation, the crude product that is obtained is purified by chromatography on fine silica gel with a gradient system that consists of n-hexane and ethyl acetate. 5.17 g (15.9 mmol, 84%) of the title compound is isolated as a colorless oil.

$^1$H-NMR (CDCl$_3$): δ=0.15 (9H), 1.07 (3H), 1.13 (3H), 1.28–1.36 (1H), 1.33 (3H), 1.41 (3H), 1.53–1.81 (3H), 2.22 (2H), 2.62 (2H), 3.85 (1H), 3.97 (1H), 4.06 (1H) ppm.

Example 1c (4S(4R,5S,6S,10RS))-4-(5-Hydroxy-2,6-dimethyl-3-oxo-4-(4-(trimethylsilyl)-but-3-in-1-yl)-10-[[diphenyl(1,1-dimethylethyl)silyl]oxy]-undec-6-in-2-yl)-2,2-dimethyl-[1,3]dioxane (A) and (4S(4S,5R,6S,10RS))-4-(5-hydroxy-2,6-dimethyl-3-oxo-4-(4-(trimethylsilyl)-but-3-in-1-yl)-10-[[diphenyl(1,1-dimethylethyl)silyl]oxy]-undec-6-in-2-yl)-2,2-dimethyl-[1,3]dioxane (B)

The solution of 1.33 ml of diisopropylamine in 35 ml of anhydrous tetrahydrofuran is cooled under an atmosphere of dry argon to −3.0° C., mixed with 4.28 ml of a 2.4 molar solution of n-butyllithium in n-hexane and stirred for another 15 minutes. At −78° C., the solution of 2.87 g (8.84 mmol) of the compound, produced according to Example 1c, in 35 ml of tetrahydrofuran is added in drops, and it is allowed to react for 1 hour. Then, it is mixed slowly with the solution of 3.93 g (10.3 mmol) of (2S,6RS)-2-methyl-6-(tert-butyl-diphenylsilyloxy)-heptanal, which was produced analogously to the process that is described in DE 197 51 200.3, in 35 ml of tetrahydrofuran, and it is poured into saturated ammonium chloride solution after 1 hour. It is diluted with water, extracted several times with ethyl acetate, the combined organic extracts are washed with saturated sodium chloride solution, dried on sodium sulfate and concentrated by evaporation in a vacuum. After column chromatography on silica gel with a gradient system that consists of n-hexane and ethyl acetate, 2.40 g (3.39 mmol, 38%) of title compound A and 1.52 g (2.15 mmol, 24%) of diastereomer B are obtained in addition to starting material.

$^1$H-NMR (CDCl$_3$) of A: δ 0.16 (9H), 0.83 (3H), 1.00 (3H), 1.02 (3H), 1.04 (9H), 1.10–1.77 (10H), 1.28 (3H), 1.31 (3H), 1.37 (3H), 1.83–2.03 (2H), 2.19–2.38 (2H), 3.52 (1H), 3.62 (1H), 3.78–3.92 (2H), 3.98 (1H), 4.23 (1H), 7.30–7.46 (6H), 7.67 (4H) ppm.

$^1$H-NMR (CDCl$_3$) of B: δ=0.13 (9H), 0.86+0.92 (3H), 0.95–1.77 (16H), 1.03 (9H), 1.21+1.25 (3H), 1.32 (3H), 1.40 (3H), 1.88–2.09 (2H), 2.26 (1H), 2.39 (1H), 3.29–3.54 (2H), 3.77–3.90 (2H), 3.96 (1H), 4.18 (1H), 7.31–7.46 (6H), 7.67 (4H) ppm.

Example 1d (4S(4R,5S,6S,10RS))-4-(2,6-Dimethyl-3-oxo-4-(4-(trimethylsilyl)-5-(tetrahydro-2H-pyran-2-yloxy)-but-3-in-1-yl)-10-[[diphenyl(1,1-dimethylethyl)silyl]oxy]-undec-6-in-2-yl)-2,2-dimethyl-[1,3]dioxane The solution of 2.35 g (3.32 mmol) of compound A, produced according to Example 1c, in 55 ml of anhydrous dichloromethane is mixed under an atmosphere of dry argon with 3.04 ml of 3,4-dihydro-2H-pyran, 0.67 g of p-toluenesulfonic acid, and it is stirred for 48 hours at 23° C. It is poured into a saturated sodium bicarbonate solution, the organic phase is separated, and it is dried on sodium sulfate. After filtration and removal of the solvent, the residue is chromatographed on fine silica gel with a mixture that consists of n-hexane and ethyl acetate. 2.29 g (2.89 mmol, 87%) of the title compound is isolated as a colorless oil.

$^1$H-NMR (CDCl$_3$): δ=0.05 (9H), 0.88–2.15 (28H), 1.03 (9H) 1.41 (3H), 1.59 (3H), 2.21–2.48 (1H), 3.31–4.53 (9H), 7.30–7.45 (6H), 7.69 (4H) ppm.

Example 1e (4S(4R,5S,6S,10RS))-4-(2,6-Dimethyl-10-hydroxy-3-oxo-5-(tetrahydro-2H-pyran-2-yloxy)-4-(but-3-in-1-yl)-undec-6-in-2-yl)-2,2-dimethyl-[1,3]dioxane The solution of 2.48 g (3.13 mmol) of the compound, produced according to Example 1d, in 25 ml of anhydrous tetrahydrofuran is mixed under an atmosphere of dry argon with 12.5 ml of a 1 molar solution of tetrabutylammonium fluoride in tetrahydrofuran, and it is stirred for 4 hours at 23° C. It is mixed with saturated sodium bicarbonate solution, extracted several times with ethyl acetate, washed with saturated sodium chloride solution and dried on sodium sulfate. The residue that is obtained after filtration and removal of the solvent is purified by chromatography on fine silica gel with a gradient system that consists of n-hexane and ethyl acetate. 1.41 g (2.93 mmol, 94%) of the title compound is isolated as a colorless oil.

Example 1f (4S(4R,5S,6S,10RS))-4-(2,6-Dimethyl-3,10-dioxo-5-(tetrahydro-2H-pyran-2-yloxy)-4-(but-3-in-1-yl)-undec-6-in-2-yl)-2,2-dimethyl-[1,3]dioxane Analogously to Example 1b, 1.27 g (2.63 mmol) of the compound, produced according to Example 1e, is reacted, and after working-up and purification, 1.14 g (2.38 mmol, 91%) of the title compound is isolated as a colorless oil.

$^1$H-NMR (CDCl$_3$): δ=0.95–2.48 (29H), 0.98+1.01 (3H), 1.42 (3H), 2.13 (3H), 3.29–3.47 (2H), 3.64–4.04 (4H), 4.20+4.32 (1H), 4.39+4.50 (1H) ppm.

Example 1g (4S(4R,5S,6S,10E/Z,13S,14E))-4-(13-[[Diphenyl(1,1-dimethylethyl)silyl]oxy]-5-(tetrahydro-2H-pyran-2-yloxy)-2,6,10,14-tetramethyl-3-oxo-15-(2-pyridyl)-4-(but-3-in-1-yl)-undec-6-in-2-yl)-2,2-dimethyl-[1,3]dioxane The suspension of 2.87 g (3.57 mmol) of (5E,3S)-[3-[[(1,1-dimethylethyl)diphenylsilyl]oxy]-4-methyl-S-(2-pyridyl)-pent-4-en-1-yl]-triphenyl-phosphonium iodide, which was produced analogously to the process described in DE 197 51 200.3, in 11 ml of anhydrous tetrahydrofuran, is mixed at 0° C. under an atmosphere of dry argon with 2.72 ml of a 1.6 M solution of n-butyllithium in n-hexane and allowed to heat to 23° C. The solution of 1.14 g (2.38 mmol) of the compound, produced according to Example 1f, in 11 ml of tetrahydrofuran is slowly added in drops to the red solution, allowed to stir for 2 hours, poured onto saturated ammonium chloride solution and extracted several times with ethyl acetate. The combined organic extracts are dried on sodium sulfate and concentrated by evaporation in a vacuum. After column chromatography on silica gel with a gradient system that consists of n-hexane and ethyl acetate, 860 mg (0.98 mmol, 41%) of the title compound is obtained in addition to 20% starting material.

$^1$H-NMR (CDCl$_3$)=0.82–2.41 (41H), 1.05 (9H), 2.00 (3H), 3.23–3.45 (2H), 3.60–4.02 (3H), 4.08–4.51 (3H), 4.92–5.24 (1H), 6.16–6.76 (1H), 6.92–7.08 (2H), 7.21–7.43 (6H), 7.49–7.72 (5H), 8.55 (1H) ppm.

Example 1h

Variant I: (4S(4R,5S,6S,10E/Z,13S,14E))-4-(13-Hydroxy-5-(tetrahydro-2H-pyran-2-yloxy)-2,6,10,14-tetramethyl-3-oxo-15-(2-pyridyl)-4-(but-3-in-1-yl)-undec-6-in-2-yl)-2,2-dimethyl-[1,3]dioxane Analogously to Example 1b, 482 mg (550 µmol) of the compound that is produced according to Example 1g is reacted, and after working-up and purification, 256 mg (401 µmol, 73%) of the title compound is isolated as a colorless oil.

$^1$H-NMR (CDCl$_3$): δ=0.88–2.48 (35H), 1.42 (3H), 1.64+1.72 (3H), 2.08 (3H), 3.29–3.47 (2H), 3.64–4.04 (4H), 4.12–4.35 (2H), 4.41+4.51 (1H), 5.20 (1H), 6.59 (1H), 7.09 (1H), 7.23 (1H), 7.63 (1H), 8.60 (1H) ppm.

Production of (4S(4R,5S,6S,10E/Z,13S,14E))-4-(13-hydroxy-5-(tetrahydro-2H-pyran-2-yloxy)-2,6,10,14-tetramethyl-3-oxo-15-(2-pyridyl)-4-(but-3-in-1-yl)-undec-6-in-2-yl)-2,2-dimethyl-[1,3]dioxane; Variant II:

Example 1i (4S(4R,5S,6S,10E/Z,13S,14E))-4-(13-[[Diphenyl(1,1-dimethylethyl)silyl]oxy]-5-hydroxy-2,6,10,14-tetramethyl-3-oxo-15-(2-pyridyl)-4-(4-(trimethylsilyl)-but-3-in-1-yl)-undec-6-in-2-yl)-2,2-dimethyl-[1,3]dioxane (A) and (4S(4S,5R,6S,10E/Z,13S,14E))-4-(13-[[diphenyl(1,1-dimethylethyl)silyl]oxy]-5-hydroxy-2,6,10,14-tetramethyl-3-oxo-15-(2-pyridyl)-4-(4-(trimethylsilyl)-but-3-in-1-yl)-undec-6-in-2-yl)-2,2-dimethyl-[1,3]dioxane (B)

Analogously to Example 1c, 2.85 g (8.78 mmol) of the compound, produced according to Example 1b, is reacted with 3.62 g (6.71 mmol) of (2S,6E/Z,9S,10E)-2,6,10-trimethyl-9-[[diphenyl(1,1-dimethylethyl)silyl]oxy]-1-oxo-1-(2-pyridyl)-undeca-6,10-diene, which was produced analogously to the process that is described in DE 197 51 200.3, and after working-up and purification, in addition to starting material, 1.28 g (1.48 mmol, 22%) of title compound C as well as 1.73 g (2.00 mmol, 30%) of title compound B are isolated in each case as a colorless oil.

$^1$H-NMR (CDCl$_3$) of A: δ=0.13 (9H), 0.86–2.52 (36H), 1.08 (9H), 1.42+1.58 (3H), 2.01 (3H), 3.32–4.85 (9H), 5.00 (1H), 6.23 (1H), 6.97–7.09 (2H), 7.21–7.45 (6H), 7.57 (1H), 7.61–7.75 (4H), 8.56 (1H) ppm.

$^1$H-NMR (CDCl$_3$) of B: δ=0.12 (9H), 0.77–2.53 (36H), 1.08 (9H), 1.38+1.62 (3H), 2.00 (3H), 3.23–4.86 (9H), 5.02 (1H), 6.23 (1H), 6.96–7.09 (2H), 7.19–7.47 (6H), 7.53–7.76 (5H), 8.57 (1H) ppm.

Example 1j (4S(4R,5S,6S,10E/Z,13S,14E))-4-(13-[[Diphenyl(1,1-dimethylethyl)silyl]oxy]-5-(tetrahydro-2H-pyran-2-yloxy)-2,6,10,14-tetramethyl-3-oxo-15-(2-pyridyl)-4-(4-(trimethylsilyl)-but-3-in-1-yl)-undec-6-in-2-yl)-2,2-dimethyl-[1,3]dioxane Analogously to Example 1d, 1.16 g (1.34 mmol) of the compound that is produced according to Example 1i is reacted, and after working-up and purification, 1.12 g (1.18 mmol, 88%) of the title compound is isolated as a colorless oil.

$^1$H-NMR (CDCl$_3$): δ=0.13 (9H), 0.86–2.52 (39H), 1.08 (9H), 2.01 (3H), 3.32–4.85 (9H), 5.00 (1H), 6.22 (1H), 6.96–7.09 (2H), 7.21–7.44 (6H), 7.56 (1H), 7.61–7.75 (4H), 8.56 (1H) ppm.

Example 1h

Variant II (4S(4R,5S,6S,10E/Z,13S,14E))-4-(13-Hydroxy-5-(tetrahydro-2H)-pyran-2-yloxy)-2,6,10,14-tetramethyl-3-oxo-15-(2-pyridyl)-4-(but-3-in-1-yl)-undec-6-in-2-yl)-2,2-dimethyl-[1,3]dioxane Analogously to Example 1e, 1.12 g (1.18 mmol) of the compound that is produced according to Example 1j is reacted, and after working-up and purification, 654 mg (1.03 mmol, 87%) of the title compound is isolated as a colorless oil. The coverage of the $^1$H-NMR spectrum is identical to that described in Example 1h, Variant I.

Example 1k (3S,6R,7S,8S,12E/Z,15S,16E)-1,3,7,15-Tetrahydroxy-4,4,8,12,16-pentamethyl-17-(2-pyridyl)-6-(but-3-in-1-yl)-heptadeca-12,16-dien-5-one The solution of 654 mg (1.03 mmol) of the compound, produced according to Example 1h, in 27 ml of anhydrous ethanol is mixed under an atmosphere of dry argon with 588 mg of p-toluenesulfonic acid-monohydrate, and it is stirred for 3 hours at 23° C. After removal of the solvent, the residue is chromatographed on fine silica gel with a mixture of n-hexane and ethyl acetate. 484 mg (942 μmol, 91%) of the title compound is isolated as a colorless oil.

$^1$H-NMR (CDCl$_3$): δ=0.90+0.92 (3H), 1.07 (3H), 1.11–2.16 (14H), 1.29 (3H), 1.63+1.42 (3H), 2.00+2.02 (3H), 2.20–2.60 (4H), 2.98 (1H), 3.48–3.67 (2H), 3.78–3.93 (2H), 4.06–4.23 (3H), 5.16+5.24 (1H), 6.52+6.57 (1H), 7.11 (1H), 7.30 (1H), 7.66 (1H), 8.58 (1H) ppm.

Example 1l (3S,6R,7S,8S,12E/Z,15S,16E)-1,3,7,15-Tetrakis-[[dimethyl(1,1-dimethylethyl)silyl]oxy]-4,4,8,12,16-pentamethyl-17-(2-pyridyl)-6-(but-3-in-1-yl)-heptadeca-12,16-dien-5-one The solution of 673 mg (1.31 mmol) of the compound, produced according to Example 1k, in 37 ml of anhydrous dichloromethane is cooled under an atmosphere of dry argon to −78° C., mixed with 2.14 ml of 2,6-lutidine, 2.41 ml of trifluoromethanesulfonic acid-tert-butyldimethylsilylester, allowed to heat within 2 hours to 0° C. and stirred for another 2 hours. It is poured into saturated sodium bicarbonate solution and extracted several times with dichloromethane. The combined organic extracts are dried on sodium sulfate and concentrated by evaporation in a vacuum. After column chromatography on silica gel with a gradient system that consists of n-hexane and ethyl acetate, 1.11 g (1.29 mmol, 99%) of the title compound is isolated as a colorless oil.

$^1$H-NMR (CDCl$_3$) δ=−0.01–0.12 (24H), 0.82–2.33 (55H), 1.08 (3H), 1.22 (3H), 1.60+1.68 (3H), 2.05 (3H), 3.22 (1H), 3.51–3.73 (2H), 3.81 (1H), 3.92 (1H), 4.11 (1H), 5.18 (1H), 6.47 (1H) 7.08 (1H), 7.22 (1H), 7.61 (1H), 8.59 (1H) ppm.

Example 1m (3S,6R,7S,8S,12E/Z,15S,16E)-1-Hydroxy-3,7,15-tris-[[dimethyl(1,1-dimethylethyl)silyl]oxy]-4,4,8,12,16-pentamethyl-17-(2-pyridyl)-6-(but-3-in-1-yl)-heptadeca-12,16-dien-5-one The solution of 1.10 mg (1.13 mmol) of the compound, produced according to Example 1l, in a mixture of 14 ml of dichloromethane and 14 ml of methanol is mixed at 23° C. under an atmosphere of dry argon with 312 mg of campher-10-sulfonic acid, and it is stirred for 2 hours. It is poured into a saturated sodium bicarbonate solution and extracted several times with dichloromethane. The combined organic extracts are dried on sodium sulfate and concentrated by evaporation in a vacuum. After column chromatography on fine silica gel with a gradient system that consists of n-hexane and ethyl acetate, 814 mg (950 pmol, 84%) of the title compound is isolated as a colorless oil.

$^1$H-NMR (CDCl$_3$): δ=0.01–0.13 (18H), 0.83–2.33 (47H), 1.12 (3H), 1.23 (3H), 1.61+1.68 (3H), 2.05 (3H), 3.28 (1H), 3.68 (2H), 3.84 (1H), 4.02–4.18 (2H), 5.18 (1H), 6.48 (1H), 7.08 (1H), 7.22 (1H), 7.61 (1H), 8.60 (1H) ppm.

Example 1n (3S,6R,7S,8S,12E/Z,15S,16E)-3,7,15-Tris-[[dimethyl(1,1-dimethylethyl)silyl]oxy]-4,4,8,12,16-pentamethyl-5-oxo-17-(2-pyridyl)-6-(but-3-in-1-yl)-heptadeca-12,16-dienal The solution of 0.129 ml of oxalyl chloride in 6.3 ml of anhydrous dichloromethane is cooled under an atmosphere of dry argon to −70° C., mixed with 209 μl of dimethyl sulfoxide, the solution of 814 mg (950 μmol) of the compound, produced according to Example 1m, in 6.3 ml of anhydrous dichloromethane, and it is stirred for 0.5 hour. Then, it is mixed with 646 μl of triethylamine, allowed to react for 1 hour at −30° C. and mixed with n-hexane and saturated sodium bicarbonate solution. The organic phase is separated, the aqueous phase is extracted several more times with n-hexane, the combined organic extracts are washed with water and dried on magnesium sulfate. The residue that is obtained after filtration and removal of the solvent is further reacted without purification.

Example 1o (3S,6R,7S,8S,12Z,15S,16E)-3,7,15-Tris-[[dimethyl (1,1-dimethylethyl)silyl]oxy]-4,4,8,12,16-pentamethyl-5-oxo-17-(2-pyridyl)-6-(but-3-in-1-yl)-heptadeca-12,16-dienoic acid (A) and (3S,6R,7S,8S,12E,15S,16E)-3,7,15-tris-[[dimethyl(1,1-dimethylethyl)silyl]oxy]-4,4,8,12,16-pentamethyl-5-oxo-17-(2-pyridyl)-6-(but-3-in-1-yl)-heptadeca-12,16-dienoic acid (B)

The solution of 852 mg (max. 950 μmol) of the compound, produced according to Example 1n, in 23 ml of acetone is cooled to −30° C., mixed with 1.19 ml of a standardized, 8N chromosulfuric acid solution and stirred for 1 hour. It is poured into a mixture that consists of water and diethyl ether, the organic phase is washed with saturated sodium chloride solution and dried on sodium sulfate. After filtration and removal of the solvent, the residue is purified by chromatography on a fine silica gel with a gradient system that consists of n-hexane and ethyl acetate. 298 mg (342 mol, 36% relative to the educt in Example 1l) of title compound A as well as 234 mg (269 μmol, 28% relative to the educt in Example 1l) of title compound B are isolated in each case as a colorless oil.

$^1$H-NMR (CDCl$_3$) of A: δ=−0.02–0.15 (18H), 0.81–0.99 (30H), 1.05–2.3 (15H), 1.12 (3H), 1.24 (3H), 1.71 (3H), 1.92 (3H), 2.38 (1H), 2.51 (1H), 3.27 (1H), 3.80 (1H), 4.17 (1H), 4.43 (1H), 5.23 (1H), 6.67 (1H), 7.18 (1H), 7.36 (1H), 7.72 (1H), 8.62 (1H) ppm.

$^1$H-NMR (CDCl$_3$) of B: δ=−0.01–0.19 (18H), 0.80–0.96 (30H), 1.00–2.45 (16H), 1.13 (3H), 1.27 (3H), 1.57 (3H), 1.94 (3H), 2.54 (1H), 3.28 (1H), 3.88 (1H), 4.13 (1H), 4.40 (1H), 5.12 (1H), 6.49 (1H), 7.18 (1H), 7.38 (1H), 7.71 (1H), 8.62 (1H) ppm.

Example 1p (3S,6R,7S,8S,12Z,15S,16E)-15-Hydroxy-3,7-bis-[[dimethyl(1,1-dimethylethyl)silyl]oxy]-4,4,8,12,16-pentamethyl-5-oxo-17-(2-pyridyl)-6-(but-3-in-1-yl)-heptadeca-12,16-dienoic acid Analogously to Example 1e, 298 mg (342 μmol) of compound A, produced according to Example 1o, is reacted, and after working-up, 294 mg (max. 342 μmol) of the title compound is isolated as a crude product, which is further reacted without purification.

Example 1q (4S,7R,8S,9S,13Z,16S(E))-4,8-Bis-[[dimethyl(1,1-dimethylethyl)silyl]oxy]-16-(1-methyl-2-(2-pyridyl)ethenyl)-1-oxa-5,5,9,13-tetramethyl-7-(but-3-in-1-yl)-cyclohexadec-13-ene-2,6-dione The solution of 294 mg (max. 342 μmol) of the compound, produced according to Example 1p, in a mixture that consists of 2.6 ml of anhydrous tetrahydrofuran and 30 ml of toluene is mixed under an atmosphere of dry argon with 284 μl of triethylamine, 268 μl of 2,4,6-trichlorobenzoyl chloride, and it is stirred for 20 minutes. This solution is added in drops within 4.5 hours to the solution of 434 mg of 4-dimethylaminopyridine in 132 ml of toluene, and it is stirred for 0.5 more hour at 23° C. It is concentrated by evaporation, taken up in a little dichloromethane and purified by chromatography on fine silica gel with a gradient system that consists of n-hexane and ethyl acetate. 136 mg (184 μmol, 54%) of the title compound is isolated as a colorless oil.

$^1$H-NMR (CDCl$_3$): =−0.08 (3H), 0.13 (9H), 0.80–2.32 (12H), 0.85 (9H), 0.94 (9H), 0.99 (3H), 1.15 (3H), 1.24 (3H), 1.68 (3H), 2.13 (3H), 2.47 (1H), 2.59–2.89 (3H), 3.11 (1H), 4.00 (1H), 4.06 (1H), 5.00 (1H), 5.18 (1H), 6.57 (1H), 7.10 (1H), 7.26 (1H), 7.63 (1H), 8.60 (1H) ppm.

Example 1r (4S,7R,8S,9S,13Z,16S(E))-4,8-Dihydroxy-16-(1-methyl-2-(2-pyridyl)ethenyl)-1-oxa-5,5,9,13-tetramethyl-7-(but-3-in-1-yl)-cyclohexadec-13-ene-2,6-dione The solution of 20 mg (27 μmol) of the compound, produced according to Example 1p, in 2 ml of anhydrous tetrahydrofuran is mixed under an atmosphere of dry argon in portions with a total of 0.57 ml of HF-pyridine complex, and it is stirred at 23° C. for 24 hours. It is poured into saturated sodium bicarbonate solution, extracted several times with dichloromethane, and the combined organic extracts are dried on sodium sulfate. After filtration and removal of the solvent, the residue that is obtained is purified by chromatography on fine silica gel with a mixture that consists of n-hexane and ethyl acetate. 9.1 mg (17.9 μmol, 66%) of the title compound is isolated as a colorless oil as well as mg of monosilylether.

$^1$H-NMR (CDCl$_3$)=1.09 (6H), 1.19–2.12 (11H), 1.38 (3H), 6.9 (3H), 2.06 (3H), 2.21–2.41 (3H), 2.50 (1H), 2.63 (1H), 2.68 (1H), 3.53 (1H), 3.70 (1H), 4.42 (1H), 4.59 (1H), 5.12 (1H), 5.22 (1H), 6.61 (1H), 7.13 (1H), 7.29 (1H), 7.68 (1H), 8.53 (1H) ppm.

Example 2

(4S,7R,8S,9S,13Z,16S(E))-4,8-Dihydroxy-16-(1-methyl-2-(2-pyridyl)ethenyl)-1-oxa-5,5,9,13-tetramethyl-7-(but-3-en-1-yl)-cyclohexadec-13-ene-2,6-dione

Example 2a (4S,7R,8S,9S,13Z,16S(E))-4,8-Bis-[[dimethyl(1,1-dimethylethyl)silyl]oxy]-16-(1-methyl-2-(2-pyridyl)ethenyl)-1-oxa-5,5,9,13-tetramethyl-7-(but-3-en-1-yl)-cyclohexadec-13-ene-2,6-dione The solution of 25 mg (34 μmol) of the compound, produced according to Example 1q, in 3 ml of ethanol, is mixed with 25 μl of pyridine, a catalytic amount of palladium on barium sulfate (10%), and it is hydrogenated under 1 atmosphere of hydrogen. After filtration and removal of the solvent, the residue is purified by chromatography on an analytical thin-layer plate. As a mobile solvent, a mixture of n-hexane and ethyl acetate is used. 13 mg (18 μmol, 52%) of the title compound is isolated as a colorless oil.

$^1$H-NMR (CDCl$_3$): δ=−0.10 (3H), 0.06 (3H), 0.11 (6H), 0.80–2.20 (1H), 0.83 (9H), 0.92 (9H), 0.98 (3H), 1.12 (3H), 1.19 (3H), 1.67 (3H), 2.12 (3H), 2.43 (1H), 2.55–2.82 (3H), 3.07 (1H), 4.00 (1H), 4.03 (1H), 4.90–5.03 (3H), 5.18 (1H), 5.72 (1H), 6.57 (1H), 7.09 (1H), 7.25 (1H), 7.62 (1H), 8.59 (1H) ppm.

Example 2b (4S,7R,8S,9S,13Z,16S(E))-4,8-Dihydroxy-16-(1-methyl-2-(2-pyridyl)ethenyl)-1-oxa-5,5,9,13-tetramethyl-7-(but-3-en-1-yl)-cyclohexadec-13-ene-2,6-dione Analogously to Example 1, 10.3 mg (14 µmol) of the compound that is produced according to Example 2a is reacted, and after working-up and purification, 5.7 mg (11 µmol, 80%) of the title compound is isolated as a colorless oil.

$^1$H-NMR (CDCl$_3$): δ=1.04 (3H), 1.09 (3H), 0.25–2.38 (13H), 1.36 (3H), 1.70 (3H), 2.07 (3H), 2.48 (1H), 2.63 (1H), 2.74 (1H), 3.31 (1H), 3.69 (1H), 4.38 (1H), 4.61 (1H), 4.97 (1H), 5.02 (1H), 5.11 (1H), 5.19 (1H), 5.77 (1H), 6.60 (1H), 7.13 (1H), 7.29 (1H), 7.68 (1H), 8.54 (1H) ppm.

Example 3

(4S,7R,8S,9S,13E,16S(E))-4,8-Dihydroxy-16-(1-methyl-2-(2-pyridyl)ethenyl)-1-oxa-5,5,9,13-tetramethyl-7-(but-3-in-1-yl)-cyclohexadec-13-ene-2,6-dione

Example 3a (3S,6R,7S,8S,12E,15S,16E)-15-Hydroxy-3,7-bis-[[dimethyl(1,1-dimethylethyl)silyl]oxy]-4,4,8,12,16-pentamethyl-5-oxo-17-(2-pyridyl)-6-(but-3-in-1-yl)-heptadeca-12,16-dienoic acid Analogously to Example 1e, 234 mg (269 µmol) of compound B that is produced according to Example 1o is reacted, and after working-up, 229 mg (max. 269 µmol) of the title compound is isolated as a crude product, which is further reacted without purification.

Example 3b (4S,7R,8S,9S,13E,16S(E))-4,8-Bis-[[dimethyl(1,1-dimethylethyl)silyl]oxy]-16-(1-methyl-2-(2-pyridyl)ethenyl)-1-oxa-5,5,9,13-tetramethyl-7-(but-3-in-1-yl)-cyclohexadec-13-ene-2,6-dione Analogously to Example 1q, 229 mg (max. 269 µmol) of the compound that is produced according to Example 3a is reacted, and after working-up and purification, 112 mg (152 µmol, 56%) of the title compound is isolated as a colorless oil.

$^1$H-NMR (CDCl$_3$): δ=0.05 (3H), 0.11 (6H), 0.15 (3H), 0.80–2.30 (33H), 1.13 (3H), 1.21 (3H), 1.62 (3H), 2.61 (3H), 2.40–2.72 (4H), 3.10 (1H), 3.91 (1H), 4.46 (1H), 5.22 (1H), 5.30 (1H), 6.56 (1H), 7.09 (1H), 7.20 (1H), 7.62 (1H), 8.60 (1H) ppm.

Example 3c (4S,7R,8S,9S,13E,16S(E))-4,8-Dihydroxy-16-(1-methyl-2-(2-pyridyl)ethenyl)-1-oxa-5,5,9,13-tetramethyl-7-(but-3-in-1-yl)-cyclohexadec-13-ene-2,6-dione Analogously to Example 1, 72 mg (98 µmol) of the compound that is produced according to Example 3b is reacted, and after working-up and purification, 32 mg (63 µmol, 64%) of the title compound is isolated as a colorless foam.

$^1$H-NMR (CDCl$_3$): δ=1.00 (3H), 1.04 (3H), 1.30–2.71 (16H), 1.32 (3H), 1.61 (3H), 2.10 (3H), 3.63 (1H), 3.70 (1H), 3.86 (1H), 3.99 (1H), 4.48 (1H), 5.10 (1H), 5.41 (1H), 6.58 (1H), 7.13 (1H), 7.33 (1H), 7.68 (1H), 8.54 (1H) ppm.

Example 4

(1S,3S(E),7S,10R,11S,12S,16R)-7,11-dihydroxy-10-(but-3-in-1-yl)-3-(1-methyl-2-(2-pyridyl)ethenyl)-8,8,12,16-tetramethyl-4,17-dioxabicyclo[14.1.0]heptadecane-5,9-dione (A) and (1R,3S(E),7S,10R,11S,12S,16S)-7,11-dihydroxy-10-(but-3-in-1-yl)-3-(1-methyl-2-(2-pyridyl)ethenyl)-8,8,12,16-tetramethyl-4,17-dioxabicyclo[14.1.0]heptadecane-5,9-dione (B)

The solution of 5 mg (10 µmol) of the compound, produced according to Example 1, in 1 ml of dichloromethane is mixed under an atmosphere of dry argon at −20° C. with 11.3 µl of a 20% solution of trifluoroacetic acid in dichloromethane and 5.6 mg of m-chloroperbenzoic acid (60%). It is stirred for 18 hours at −18° C., poured onto saturated sodium thiosulfate solution, extracted several times with dichloromethane, the combined organic extracts are washed with sodium bicarbonate solution, saturated sodium chloride solution and dried on magnesium sulfate. The residue that is obtained after filtration and removal of the solvent is purified by chromatography on an analytical thin-layer plate. As a mobile solvent and eluant, a mixture that consists of dichloromethane and ethanol is used. 1.3 mg (2.5 µmol, 25%) of title compound A (or B) and 2.0 mg (3.8 µmol, 39%) of title compound B (or A) are isolated in each case as a colorless oil.

$^1$H-NMR (CDCl$_3$) of A (or B): δ=1.01 (3H), 1.07 (3H), 1.23–2.20 (13H), 1.30 (3H), 1.46 (3H), 2.10 (3H), 2.26 (1H), 2.40 (1H), 2.58 (1H), 2.82 (1H), 2.97 (1H), 3.63 (2H), 4.39 (1H), 5.22 (1H), 5.47 (1H), 6.61 (1H), 7.15 (1H), 7.28 (1H), 7.69 (1H), 8.55 (1H) ppm.

$^1$H-NMR (CDCl$_3$) of B (or A): δ=0.98 (3H), 1.08 (3H), 1.27–2.19 (13H), 1.32 (3H), 1.43 (3H), 2.12 (3H), 2.30 (1H), 2.48 (1H), 2.70 (1H), 2.96 (1H), 3.15 (1H), 3.4.7 (1H), 3.57 (1H), 4.01 (1H), 4.49 (1H), 5.50 (1H), 6.67 (1H), 7.12 (1H), 7.27 (1H), 7.66 (1H), 8.58 (1H) ppm.

Example 5

(1S,3S(E),7S,10R,11S,12S,16R)-7,11-Dihydroxy-10-(but-3-en-1-yl)-3-(1-methyl-2-(2-pyridyl)ethenyl)-8,8,12,16-tetramethyl-4,17-dioxabicyclo[14.1.0]heptadecane-5,9-dione (A) and (1R,3S(E),7S,10R,11S,12S,16S)-7,11-dihydroxy-10-(but-3-en-1-yl)-3-(1-methyl-2-(2-pyridyl)ethenyl)-8,8,12,16-tetramethyl-4,17-dioxabicyclo[14.1.0]heptadecane-5,9-dione (B)

Analogously to Example 4, 6.6 mg (13 µmol) of the compound that is produced according to Example 2 is reacted, and after working-up and purification, 1.4 mg (2.7 µmol, 20%) of title compound A (or B) and 0.9 mg (1.7 µmol, 13%) of title compound B (or A) are isolated in each case as a colorless foam.

$^1$H-NMR (CDCl$_3$) of A (or B): δ=1.00 (3H), 1.07 (3H), 1.21–2.05 (12H), 1.30 (3H), 1.40 (3H), 2.10 (3H), 2.16 (1H), 2.38 (1H), 2.57 (1H), 2.81 (1H), 2.97 (1H), 3.44 (1H), 3.63 (1H), 4.38 (1H), 4.98 (1H), 5.02 (1H), 5.28 (1H), 5.45 (1H), 5.77 (1H), 6.62 (1H), 7.18 (1H), 7.31 (1H), 7.71 (1H), 8.56 (1H) ppm.

¹H-NMR (CDCl₃) of B (or A): δ=0.94 (3H), 1.05 (3H), 1.18–2.17 (13H), 1.30 (3H), 1.38 (3H), 2.12 (3H), 2.48 (1H), 2.62 (1H), 2.95 (1H), 3.28 (1H), 3.30 (1H), 3.50 (1H), 3.96 (1H), 4.41 (1H), 4.95 (1H), 5.00 (1H), 5.52 (1H), 5.25 (1H), 6.73 (1H), 7.18 (1H), 7.33 (1H), 7.71 (1H), 8.58 (1H) ppm.

Example 6

(1S,3S(E),7S,10R,11S,12S,16S)-7,11-Dihydroxy-10-(but-3-in-1-yl)-3-(1-methyl-2-(2-pyridyl)ethenyl)-8,8,12,16-tetramethyl-4,17-dioxabicyclo[14.1.0]heptadecane-5,9-dione (A) and (1R,3S(E),7S,10R,11S,12S,16R)-7,11-dihydroxy-10-(but-3-in-1-yl)-3-(1-methyl-2-(2-pyridyl)ethenyl)-8,8,12,16-tetramethyl-4,17-dioxabicyclo[14.1.0]heptadecane-5,9-dione (B)

Analogously to Example 4, 14 mg (27 μmol) of the compound that is produced according to Example 3 is reacted, and after working-up and purification, 7.8 mg (15 mol, 55%) of title compound A (or B) and 4.7 mg (9 μmol, 33%) of title compound B (or A) are isolated in each case as a colorless foam.

¹H-NMR (CDCl₃) of A (or B): δ=0.93 (3H), 1.04 (3H), 1.23–2.19 (13H), 1.29 (3H), 1.42 (3H), 2.13 (3H), 2.28 (1H), 2.48–2.65 (2H), 2.71 (1H), 2.89 (1H), 3.57 (1H), 3.83 (1H), 4.36 (1H), 4.47 (1H), 5.51 (1H), 6.63 (1H), 7.12 (1H), 7.28 (1H), 7.67 (1H), 8.57 (1H) ppm.

¹H-NMR (CDCl₃) of B (or A): δ=0.96 (3H), 1.10 (3H), 1.21–2.18 (13H), 1.26 (3H), 1.40 (3H), 2.10 (3H), 2.29 (1H), 2.61 (2H), 2.86 (1H), 2.99 (1H), 3.58 (1H), 3.79 (2H), 4.37 (1H), 5.46 (1H), 6.61 (1H), 7.12 (1H), 7.26 (1H), 7.66 (1H), 8.57 (1H) ppm.

Example 7

(4S,7R,8S,9S,13E,16S(E))-4,8-Dihydroxy-16-(1-methyl-2-(2-pyridyl)ethenyl)-1-oxa-5,5,9,13-tetramethyl-7-(but-3-en-1-yl)-cyclohexadec-13-ene-2,6-dione Analogously to Example 2a, 14 mg (27 μmol) of the compound that is produced according to Example 3 is reacted, and after working-up and purification, 4.1 mg (8 μmol, 29%) of the title compound is isolated as a colorless foam.

¹H-NMR (CDCl₃): δ=0.98 (3H), 1.02 (3H), 1.30 (3H), 1.36–2.68 (16H), 1.61 (3H), 2.09 (3H), 3.43 (1H), 3.70 (1H), 4.17 (1H), 4.45 (1H), 4.94 (1H), 5.00 (1H), 5.09 (1H), 5.39 (1H), 5.72 (1H), 6.58 (1H), 7.12 (1H), 7.35 (1H), 7.67 (1H), 8.52 (1H) ppm.

Example 8

(1S,3S(E),7S,10R,11S,12S,16S)-7,11-Dihydroxy-10-(but-3-en-1-yl)-3-(1-methyl-2-(2-pyridyl)ethenyl)-8,8,12,16-tetramethyl-4,17-dioxabicyclo[14.1.0]heptadecane-5,9-dione (A) and (1R,3S(E),7S,10R,11S,12S,16R)-7,11-dihydroxy-10-(but-3-en-1-yl)-3-(1-methyl-2-(2-pyridyl)ethenyl)-8,8,12,16-tetramethyl-4,17-dioxabicyclo[14.1.0]heptadecane-5,9-dione (B)

Analogously to Example 4, 4.1 mg (8 μmol) of the compound that is produced according to Example 7 is reacted, and after working-up and purification, 1.7 mg (3.2 μmol, 40%) of title compound A (or B) and 0.4 mg (0.8 μmol, 9%) of title compound B (or A) are isolated in each case as a colorless foam.

¹H-NMR (CDCl₃) of A (or B): δ=0.91 (3H), 1.02 (3H), 1.13–2.17 (15H), 1.28 (3H), 1.38 (3H), 2.11 (3H), 2.53 (2H), 2.87 (1H), 2.96 (1H), 3.38 (1H), 3.78 (1H), 4.35 (1H), 4.37 (1H), 4.95 (1H), 5.00 (1H), 5.50 (1H), 5.76 (1H), 6.64 (1H), 7.12 (1H), 7.30 (1H), 7.67 (1H), 8.57 (1H) ppm.

¹H-NMR (CDCl₃) of B (or A): δ=0.92 (3H), 1.09 (3H), 1.18–2.13 (15H), 1.26 (3H), 1.38 (3H), 2.08 (3H), 2.49–2.60 (2H), 2.85–2.99 (2H), 3.39 (1H), 3.72 (1H), 3.89 (1H), 4.28 (1H), 4.92–5.06 (2H), 5.45 (1H), 5.76 (1H), 6.60 (1H), 7.12 (1H), 7.26 (1H), 7.68 (1H), 8.57 (1H) ppm.

Example 9

(4S,7R,8S,9S,13Z,16S(E))-4,8-Dihydroxy-16-(1-methyl-2-(2-methylthiazol-4-yl)ethenyl)-1-oxa-5,5,9,13-tetramethyl-7-(prop-2-en-1-yl)-cyclohexadec-13-ene-2,6-dione

Example 9a (3RS,4S)-4-(2-Methyl-3-hydroxy-hept-6-en-2-yl)-2,2-dimethyl-[1,3]dioxane Analogously to Example 1a, 5.5 g (30 mmol) of (4S)-4-(2-methyl-1-oxo-prop-2-yl)-2,2-dimethyl-[1,3]dioxane, which was produced analogously to the process described in DE 197 51 200.3, is reacted with but-3-en-1-yl-magnesium bromide, and after working-up and purification, 3.84 g (15.8 mmol, 53%) of the title compound is isolated as a colorless oil.

Example 9b (4S)-4-(2-Methyl-3-oxo-hept-6-en-2-yl)-2,2-dimethyl-[1,3]dioxane

Analogously to Example 1b, 3.84 g (15.8 mmol) of the compound that is produced according to Example 9a is reacted, and after working-up and purification, 3.0 g (12.5 mmol, 79%) of the title compound is isolated as a colorless oil.

¹H-NMR (CDCl₃): δ=1.07 (3H), 1.14 (3H), 1.33 (4H), 1.41 (3H), 1.62 (1H), 2.29 (2H), 2.60 (2H), 3.86 (1H), 3.97 (1H), 4.05 (1H), 4.96 (1H), 5.02 (1H), 5.81 (1H) ppm.

Example 9c (4S(4R,5S,6S,10E/Z,13S,14E))-4-(13-[[Dimethyl(1,1-dimethylethyl)silyl]oxy]-5-hydroxy-2,6,10,14-tetramethyl-3-oxo-15-(2-methylthiazol-4-yl)-4-(prop-2-en-1-yl)-pentadec-2-yl)-2,2-dimethyl-[1,3]dioxane (A) and (4S(4S,5R,6S,10E/Z,13S,14E))-4-(13-[[dimethyl(1,1-dimethylethyl)silyl]oxy]-5-hydroxy-2,6,10,14-tetramethyl-3-oxo-15-(2-methylthiazol-4-yl)-4-(prop-2-en-1-yl)-pentadec-2-yl)-2,2-dimethyl-[1,3]dioxane (B)

Analogously to Example 1c, 2.07 g (8.61 mmol) of the compound, produced according to Example 9b, with 2.01 g (4.61 mmol) of (2S,6E/Z,9S,10E)-2,6,10-trimethyl-9-[dimethyl(1,1-dimethylethyl)silyl]oxy]-1-oxo-11-(2-methylthiazol-4-yl)-undeca-6,10-diene that was produced analogously to the process that is described in DE 197 51 200.3 is reacted, and after working-up and purification, in addition to starting material, 995 mg (1.47 mmol, 32%) of title compound A as well as 784 mg (1.16 mmol, 25%) of title compound B are isolated in each case as a colorless oil.

$^1$H-NMR (CDCl$_3$) of A: δ=0.01 (3H), 0.07 (3H), 0.85 (3H), 0.90 (9H), 0.98 (3H), 1.00–2.33 (12H), 1.23 (3H), 1.33 (3H), 1.39 (3H), 1.60+1.67 (3H), 2.00 (3H), 2.46 (1H), 2.72 (3H), 2.99 (1H), 3.34 (1H), 3.49 (1H), 3.87 (1H), 3.98 (1H), 4.09 (1H), 4.13 (1H), 4.98 (1H), 5.03 (1H), 5.13 (1H), 5.71 (1H), 6.44 (1H), 6.93 (1H) ppm.

$^1$H-NMR (CDCl$_3$) of B: δ=0.00 (3H), 0.03 (3H), 0.88 (9H), 0.94 (3H), 1.03–1.72 (7H), 1.08 (3H), 1.17 (3H), 1.31 (3H), 1.39 (3H), 1.60+1.68 (3H), 1.89–2.08 (2H), 1.99 (3H), 2.17–2.51 (4H), 2.71 (3H), 2.74+2.87 (1H), 3.31 (1H), 3.57 (1H), 3.84 (1H), 3.95 (1H), 4.03–4.17 (2H), 4.98 (1H), 5.03 (1H), 5.13 (1H), 5.73 (1H), 6.64 (1H), 6.92 (1H) ppm.

Example 9d (3S,6R,7S,8S,12E/Z,15S,16E)-15-[[Dimethyl(1,1-dimethylethyl)silyl]oxy]-1,3,7-trihydroxy-4,4,8,12,16-pentamethyl-17-(2-methylthiazol-4-yl)-6-(prop-2-en-1-yl)-heptadeca-12,16-dien-5-one Analogously to Example 1k, 1.33 g (1.97 mmol) of compound A that is produced according to Example 9c is reacted, and after working-up and purification, 1.02 g (1.60 mmol, 81%) of the title compound is isolated as a colorless oil.

$^1$H-NMR (CDCl$_3$): δ=0.01 (3H), 0.07 (3H), 0.89 (12H), 1.00–2.38 (12H), 1.40+1.07 (3H), 1.23+1.25 (3H), 1.60+1.68 (3H), 1.97+1.99 (3H), 2.52 (1H), 2.67–2.89 (1H), 2.73+2.77 (3H), 3.01 (1H), 3.33 (1H), 3.40–3.53 (1H), 3.74–3.9.3 (3H), 4.03–4.19 (2H), 5.00 (1H), 5.06 (1H), 5.10+5.20 (1H), 5.71 (1H), 6.42 (1H), 6.93 (1H) ppm.

Example 9e (3S,6R,7S,8S,12E/Z,15S,16E)-1,3,7,15-Tetrakis-[[dimethyl(1,1-dimethylethyl)silyl]oxy[4,4,8,12,16-pentamethyl-17-(2-methylthiazol-4-yl)-6-(prop-2-en-1-yl)-heptadeca-1,2,16-dien-5-one Analogously to Example 11, 1.02 g (1.60 mmol) of the compound that is produced according to Example 9d is reacted, and after working-up and purification, 1.46 g (1.49 mmol, 93%) of the title compound is isolated as a colorless oil.

$^1$H-NMR (CDCl$_3$): δ=0.00–0.11 (24H), 0.83–0.98 (39H), 1.01–1.62 (8H), 1.07 (3H), 1.20 (3H), 1.59+1.67 (3H), 1.97 (1H), 2.00 (3H), 2.19–2.34 (3H), 2.48 (1H), 2.72 (3H); 3.13 (1H), 3.57 (1H), 3.67 (1H), 3.78 (1H), 3.87 (1H), 4.09 (1H), 4.93 (1H), 4.99 (1H), 5.15 (1H), 5.77 (1H), 6.64 (1H), 6.91 (1H) ppm.

Example 9f (3S,6R,7S,8S,12E/Z,15S,16E)-1-Hydroxy-3,7,15-tris-[[dimethyl(1,1-dimethylethyl)silyl]oxy]-4,4,8,12,16-pentamethyl-17-(2-methylthiazol-4-yl)-6-(prop-2-en-1-yl)-heptadeca-12,16-dien-5-one Analogously to Example 1m, 1.45 g (1.48 mmol) of the compound that is produced according to Example 9e is reacted, and after working-up and purification, 1.19 g (1.37 mmol, 93%) of the title compound is isolated as a colorless oil.

$^1$H-NMR (CDCl$_3$): δ=0.01–0.14 (18H), 0.82–0.97 (30H), 1.04–1.70 (7H), 1.09 (3H), 1.19 (3H), 1.59+1.68 (3H), 1.84–2.08 (3H), 2.00 (3H), 2.18–2.36 (3H), 2.47 (1H), 2.71 (3H), 3.13 (1H), 3.66 (2H), 3.80 (1H), 4.40 (1H), 4.10 (1H), 4.96 (1H), 5.01 (1H), 5.14 (1H), 5.77 (1H), 6.46 (1H), 6.92 (1H) ppm.

Example 9g (3S,6R,7S,8S,12E/Z,15S,16E)-3,7,15-Tris-[(dimethyl(1,1-dimethylethyl)silyl]oxy]-4,4,8,12,16-pentamethyl-17-(2-methylthiazol-4-yl)-5-oxo-6-(prop-2-en-1-yl)-heptadeca-12,16-dienal Analogously to Example in, 1.18 g (1.37 mmol) of the compound that is produced according to Example 9f is reacted, and after working-up, 1.25 g (max. 1.37 mmol) of the title compound is isolated as a yellow oil, which is further reacted without purification.

Example 9h (3S,6R,7S,8S,12Z,15S,16E)-3,7,15-Tris-[[dimethyl(1,1-dimethylethyl)silyl]oxy]-4,4,8,12,16-pentamethyl-17-(2-methylthiazol-4-yl)-5-oxo-6-(prop-2-en-1-yl)-heptadeca-12,16-dienoic acid (A) and (3S,6R,7S,8S,12E,15S,16E)-3,7,15-tris-[[dimethyl(1,1-dimethylethyl)silyl]oxy]-4,4,8,12,16-pentamethyl-17-(2-methylthiazol-4-yl)-5-oxo-6-(prop-2-en-1-yl)-heptadeca-12,16-dienoic acid (B)

Analogously to Example 1o, 1.25 g (max. 1.37 mmol) of the compound that is produced according to Example 9g is reacted, and after working-up and purification, 302 mg (0.34 mmol, 25%) of title compound A and 230 mg (0.26 mmol, 19%) of title compound B are isolated in each case as a colorless oil.

$^1$H-NMR (CDCl$_3$) of A: δ=–0.02–0.15 (18H), 0.82–0.97 (30H), 1.05–2.53 (14H), 1.12 (3H), 1.17 (3H), 1.70 (3H), 1.96 (3H), 2.71 (3H), 3.17 (1H), 3.72 (1H), 4.16 (1H), 4.37 (1H), 4.94 (1H), 4.99 (1H), 5.20 (1H), 5.73 (1H), 6.66 (1H), 6.93 (1H) ppm.

$^1$H-NMR (CDCl$_3$) of B: δ=–0.03–0.15 (18H), 0.81–0.95 (30H), 1.01–2.50 (13H), 1.12 (3H), 1.18 (3H), 1.57 (3H), 1.95 (3H), 2.60 (1H), 2.70 (3H), 3.22 (1H), 3.79 (1H), 4.08 (1H), 4.32 (1H), 4.94 (1H), 5.00 (1H), 5.11 (1H) 5.74 (1H), 6.46 (1H), 6.93 (1H) ppm.

Example 9i (3S,6R,7S,8S,12Z,15S,16E)-3,7-Bis-[[dimethyl(1,1-dimethylethyl)silyl]oxy]-15-hydroxy-4,4,8,12,16-pentamethyl-17-(2-methylthiazol-4-yl)-5-oxo-6-(prop-2-en-1-yl)-heptadecane-12,16-dienoic acid Analogously to Example 1e, 302 mg (0.34 mmol) of compound A that is produced according to Example 9h is reacted, and after working-up, 296 mg (max. 0.34 mmol) of the title compound is isolated as a pale yellow oil, which is further reacted without purification.

Example 9j (4S,7R,8S,9S,13Z,16S(E))-4,8-Bis-[[dimethyl(1,1-dimethylethyl)silyl]oxy]-16-(1-methyl-2-(2-methylthiazol-4-yl)-ethenyl)-1-oxa-5,5,9,13-tetramethyl-7-(prop-2-en-1-yl-cyclohexadec-13-ene-2,6-dione Analogously to Example 1q, 296 mg (max. 0.34 mmol) of the compound that is produced according to Example 9i is reacted, and after working-up and purification, 166 mg (0.22 mmol, 65%) of the title compound is isolated as a colorless oil.

$^1$H-NMR (CDCl$_3$): δ=−0.10 (3H), 0.09 (3H), 0.11 (3H), 0.13 (3H), 0.86 (9H), 0.80–2.85 (13H), 0.94 (9H), 1.00 (3H), 1.10 (3H), 12.0 (3H), 1.68 (3H), 2.10 (3H), 2.71 (3H), 3.11 (1H), 4.01 (2H), 4.85–5.03 (3H), 5.16 (1H), 5.78 (1H), 6.57 (1H), 6.98 (1H) ppm.

Example 9k (4S,7R,8S,9S,13Z,16S(E))-4,8-Dihydroxy-16-(1-methyl-2-(2-methylthiazol-4-yl)ethenyl)-1-oxa-5,5,9,13-tetramethyl-7-(prop-2-en-1-yl)-cyclohexadec-13-ene-2,6-dione Analogously to Example 1, 25 mg (34 µmol) of the compound that is produced according to Example 9j is reacted, and after working-up and purification, 10 mg (19 µmol, 57%) of the title compound is isolated as a colorless oil.

$^1$H-NMR (CDCl$_3$): δ=1.03 (3H), 1.05 (3H), 1.20–2.74 (14H), 1.30 (3H), 1.69 (3H), 2.07 (3H), 2.69 (3H), 3.33 (1H), 3.69 (1H), 3.72 (1H), 4.23 (1H), 5.02 (1H), 5.07 (1H), 5.12 (1H), 5.21 (1H), 5.76 (1H), 6.57 (1H), 6.96 (1H) ppm.

Example 10

(1S,3S(E),7S,10R,11S,12S,16R)-7,11-Dihydroxy-10-(prop-2-en-1-yl)-3-(1-methyl-2-(2-methylthiazol-4-yl)ethenyl)-8,8,12,16-tetramethyl-4,17-dioxabicyclo[14.1.0]heptadecane-5,9-dione (A) and (1R,3S(E),7S,10R,11S,12S,16S)-7,11-dihydroxy-10-(prop-2-en-1-yl)-3-(1-methyl-2-(2-methylthiazol-4-yl)ethenyl)-8,8,12,16-tetramethyl-4,17-dioxabicyclo[14.1.0]heptadecane-5,9-dione (B)

The solution of 8.0 mg (15.5 µmol) of the compound, produced according to Example 9, in 1 ml of acetonitrile is mixed with 89 µl of a 1M solution of sodium ethylenediamine tetraacetate, cooled to 0° C. and mixed with 148 µl of 1,1,1-trifluoroacetone as well as a mixture that consists of 22 mg of oxone and 41 mg of sodium bicarbonate. It is allowed to react for 5 hours, poured onto sodium thiosulfate solution and extracted several times with ethyl acetate. The combined organic extracts are washed with saturated sodium chloride solution, and the residue that is obtained after filtration and removal of the solvent is purified by chromatography on an analytic thin-layer plate. As a mobile solvent, a mixture of n-hexane and ethyl acetate is used. 3.2 mg (6 µmol, 39%) of title compound A and 1.0 mg (2 µmol, 12%) of title compound B are isolated in each case as a colorless oil.

$^1$H-NMR (CDCl$_3$) of A: δ=1.00 (3H), 1.02 (3H), 1.21–1.82 (7H), 1.29 (3H), 1.36 (3H), 1.95–2.06 (2H), 2.11 (3H), 2.30 (1H), 2.40 (1H), 2.48–2.62 (2H), 2.72 (3H), 2.81 (2H), 3.50 (1H), 3.69 (1H), 4.27 (1H), 4.52 (1H), 5.01 (1H), 5.06 (1H), 5.46 (1H), 5.72 (1H), 6.59 (1H), 6.99 (1H) ppm.

$^1$H-NMR (CDCl$_3$) of B: δ=0.96 (3H), 1.00 (3H), 1.20–1.91 (8H), 1.29 (3H), 1.34 (3H), 2.04 (1H), 2.09 (3H), 2.33 (1H), 2.42–2.61 (3H), 2.76 (3H), 2.93 (1H), 2.96 (1H), 3.38 (1H), 3.68 (1H), 3.99 (1H), 4.29 (1H), 4.98 (1H), 5.01 (1H), 5.57 (1H), 5.74 (1H), 6.69 (1H), 7.01 (1H) ppm.

Example 11

(4S,7R,8S,9S,13E,16S(E))-4,8-Dihydroxy-16-(1-methyl-2-(2-methylthiazol-4-yl)ethenyl)-1-oxa-5,5,9,13-tetramethyl-7-(prop-2-en-1-yl)-cyclohexadec-13-ene-2,6-dione

Example 11a (3S,6R,7S,8S,12E,15S,16E)-3,7-Bis-[(dimethyl(1,1-dimethylethyl)silyl]oxy]-15-hydroxy-4,4,8,12,16-pentamethyl-17-(2-methylthiazol-4-yl)-5-oxo-6-(prop-2-en-1-yl)-heptadeca-12,16-dienoic acid Analogously to Example 1e, 230 mg (0.26 mmol) of compound B that is produced according to Example 9h is reacted, and after working-up, 214 mg (max. 0.26 mmol) of the title compound is isolated as a pale yellow oil, which is further reacted without purification.

Example 11b (4S,7R,8S,9S,13E,16S(E))-4,8-Bis-[[dimethyl(1,1-dimethylethyl)-silyl]oxy]-16-(1-methyl-2-(2-methylthiazol-4-yl)ethenyl)-1-oxa-5,5,9,13-tetramethyl-7-(prop-2-en-1-yl)-cyclohexadec-13-ene-2,6-dione Analogously to Example 1q, 214 mg (max. 0.26 mmol) of the compound that is produced according to Example 11a is reacted, and after working-up and purification, 114 mg (0.15 mmol, 59%) of the title compound is isolated as a colorless oil.

$^1$H-NMR (CDCl$_3$): δ=0.05 (3H), 0.08 (3H), 0.10 (3H), 0.13 (3H), 0.82–0.94 (21H), 1.12 (3H), 1.15–2.62 (13H), 1.21 (3H), 1.59 (3H), 2.11 (3H), 2.71 (3H), 3.03 (1H), 3.87 (1H), 4.30 (1H), 4.99 (1H), 5.03 (1H), 5.21 (1H), 5.28 (1H), 5.79 (1H), 6.51 (1H), 6.91 (1H) ppm.

Example 11c (4S,7R,8S,9S,13E,16S(E))-4,8-Dihydroxy-16-(1-methyl-2-(2-methylthiazol-4-yl)ethenyl)-1-oxa-5,5,9,13-tetramethyl-7-(prop-2-en-1-yl)-cyclohexadec-13-ene-2,6-dione Analogously to Example 1, 15 mg (20 µmol) of the compound that is produced according to Example 11b is reacted, and after working-up and purification, 7.3 mg (14 µmol, 71%) of the title compound is isolated as a colorless oil.

$^1$H-NMR (CDCl$_3$): δ=0.80–2.62 (13H), 0.99 (3H), 1.01 (3H), 1.26 (3H), 1.60 (3H), 2.04 (3H), 2.69 (3H), 3.49 (1H),

Example 12

(1R,3S(E),7S,10R,11S,12S,16R)-7,11-Dihydroxy-
10-(prop-2-en-1-yl)-3-(1-methyl-2-(2-methylthiazol-
4-yl)ethenyl)-8,8,12,16-tetramethyl-4,17-dioxabicy-
clo[14.1.0]heptadecane-5,9-dione (A) and (1S,3S
(E),7S,10R,11S,12S,16S)-7,11-dihydroxy-10-(prop-
2-en-1-yl)-3-(1-methyl-2-(2-methylthiazol-4-yl)
ethenyl)-8,8,12,16-tetramethyl-4,17-dioxabicyclo
[14.1.0]heptadecane-5,9-dione (B)

Analogously to Example 10, 7.3 mg (14 μmol) of the compound that is produced according to Example 11 is reacted, and after working-up and purification, 2.3 mg (4.3 μmol, 31%) of title compound A (or B) and 2.0 mg (3.7 μmol, 27%) of title compound B (or A) are isolated in each case as a colorless oil.

$^1$H-NMR (CDCl$_3$) of A (or B): δ=0.90–2.34 (10H), 0.95 (3H), 1.01 (3H), 1.29 (3H), 1.38 (3H), 2.10 (3H), 2.47–2.62 (3H), 2.72 (3H), 2.88 (2H), 3.48 (1H), 3.80 (1H), 4.19 (1H), 4.32 (1H), 5.02 (1H), 5.07 (1H), 5.48 (1H), 5.77 (1H), 6.63 (1H), 7.00 (1H) ppm.

$^1$H-NMR (CDCl$_3$) of B (or A): δ=0.97 (3H), 1.06 (3H), 1.20–2.12 (9H), 1.25 (3H), 1.34 (3H), 2.08 (3H), 2.28 (1H), 2.46–2.62 (3H), 2.72 (3H), 2.92 (2H), 3.40 (1H), 3.68 (1H), 3.75 (1H), 4.28 (1H), 5.01 (1H), 5.06 (1H), 5.44 (1H), 5.72 (1H), 6.62 (1H), 6.99 (1H) ppm.

Example 13

(4S,7R,8S,9S,13Z,16S(E))-4,8-Dihydroxy-16-(1-
methyl-2-(2-pyridyl)ethenyl)-1-oxa-5,5,9,13-tetram-
ethyl-7-(prop-2-in-1-yl)-cyclohexadec-13-ene-2,6-
dione

Example 13a (3RS,4S)-4-(2-Methyl-3-hydroxy-8-(trimethylsilyl)-
hept-6-in-2-yl)-2,2-dimethyl-[1,3]dioxane Analogously to Example 1a, 7.0 g (37 mmol) of (4S)-4-(2-methyl-1-oxo-prop-2-yl)-2,2-dimethyl-[1,3]dioxane, which was produced analogously to the process described in DE 197 51 200.3, is reacted with 4-trimethylsilyl-but-3-in-1-yl-magnesium bromide, and after working-up and purification, 4.9 g (15.7 mmol, 42%) of the title compound is isolated as a colorless oil.

Example 13b (4S)-4-(2-Methyl-3-oxo-8-(trimethylsilyl)-hept-6-in-
2-yl)-2,2-dimethyl-[1,3]dioxane Analogously to Example 1b, 4.87 g (15.6 mmol) of the compound that is produced according to Example 13a is reacted, and after working-up and purification, 4.10 g (13.2 mmol, 85%) of the title compound is isolated as a colorless oil.

$^1$H-NMR (CDCl$_3$): δ=0.13 (9H), 1.08 (3H), 1.13 (3H), 1.32 (1H), 1.34 (3H), 1.41 (3H), 1.61 (1H), 2.45 (2H), 2.73 (2H), 3.84 (1H), 3.96 (1H), 4.02 (1H) ppm.

Example 13c (4S(4R,5S,6S,10E/Z,13S,14E))-4-(13-[[Dimethyl(1,
1-dimethylethyl)silyl]oxy]-5-hydroxy-2,6,10,14-
tetramethyl-3-oxo-15-(2-pyridyl)-4-(4-(trimethylsi-
lyl)-prop-2-in-1-yl)-pentadec-2-yl)-2,2-dimethyl-[1,
3]dioxane (A) and (4S(4S,5R,6S,10E/Z, 13S,14E))-
4-(13-[[dimethyl(1,1-dimethylethyl)silyl]oxy]-5-
hydroxy-2,6,10,14-tetramethyl-3-oxo-15-(2-
pyridyl)-4-(4-(trimethylsilyl)-prop-2-in-1-yl)-
pentadec-2-yl)-2,2-dimethyl-[1,3]dioxane (B)

Analogously to Example 1c, 2.74 g (8.82 mmol) of the compound that is produced according to Example 13b is reacted with 3.02 g (7.27 mmol) of (2S,6E/Z,9S,10E)-2,6,10-trimethyl-9-[[dimethyl(1,1-dimethylethyl)silyl]oxy]-1-oxo-11-(2-pyridyl)-undeca-6,10-diene, which was produced analogously to the process that is described in DE 197 51 200.3, and after working-up and purification, in addition to 50% starting material, 1.63 g (2.2 mmol, 31%) of title compound A and 0.50 g (0.69 mmol, 9%) of title compound B are isolated in each case as a colorless oil.

$^1$H-NMR (CDCl$_3$) of A: δ=0.00–0.20 (15H), 0.83–0.95 (12H), 1.00–1.80 (20H), 1.60+1.68 (3H), 1.90–2.10 (1H), 2.05 (3H), 2.28 (2H), 2.41 (1H), 2.55 (1H), 3.03+3.09 (1H), 3.46 (1H), 3.52 (1H), 3.78–4.20 (4H), 5.18 (1H), 6.49 (1H), 7.09 (1H), 7.23 (1H), 7.63 (1H), 8.60 (1H) ppm.

$^1$H-NMR (CDCl$_3$) of B: δ=0.00–0.20 (15H), 0.86–1.00 (12H), 1.00–1.76 (19H), 1.61+1.70 (3H), 1.90–2.10 (2H), 2.06 (3H), 2.29 (2H), 2.53 (2H), 3.04 (1H), 3.43 (1H), 3.61 (1H), 3.80–4.18 (4H), 5.18 (1H), 6.48 (1H), 7.09 (1H), 7.23 (1H), 7.62 (1H), 8.59 (1H) ppm.

Example 13d (3S,6R,7S,8S,12E/Z,15S,16E)-15-[[Dimethyl(1,1-
dimethylethyl)silyl]oxy]-1,3,7-trihydroxy-4,4,8,12,
16-pentamethyl-17-(2-pyridyl)-6-(3-(trimethylsilyl)-
prop-2-in-1-yl)-heptadeca-12,16-dien-5-one Analogously to Example 1k, 2.25 g (3.10 mmol) of the compound that is produced according to Example 13c is reacted, and after working-up and purification, in addition to starting material, 1.31 g (1.91 mmol, 62%) of the title compound is isolated as a colorless oil.

$^1$H-NMR (CDCl$_3$): δ=0.00–0.19 (9H), 0.85–0.98 (12H), 1.03–2.43 (25H), 1.60+1.69 (3H), 2.00+2.02 (3H), 2.69 (1H), 3.01+3.10 (1H), 3.31–3.60 (3H), 3.84 (2H), 4.02–4.26 (2H), 5.10+5.26 (1H), 6.41 (1H), 7.13 (1H), 7.32 (1H), 7.68 (1H), 8.61 (1H) ppm.

Example 13e (3S,6R,7S,8S,12E/Z,15S,16E)-1,3,7,15-Tetrakis-
[[dimethyl(1,1-dimethylethyl)silyl]oxy]-4,4,8,12,16-
pentamethyl-17-(2-pyridyl)-6-(3-(trimethylsilyl)-
prop-2-in-1-yl)-heptadeca-12,16-dien-5-one Analogously to Example 11, 1.49 g (2.17 mmol) of the compound that is produced according to Example 13d is reacted, and after working-up and purification, 1.95 g (1.90 mmol, 87%) of the title compound is isolated as a colorless oil.

$^1$H-NMR (CDCl$_3$): δ=0.00–0.18 (33H), 0.86–0.98 (39H), 1.01–1.73 (7H), 1.08 (3H), 1.26 (3H), 1.61+1.69 (3H), 1.90–2.09 (2H), 2.05 (3H), 2.29 (2H), 2.51 (2H), 3.29 (1H), 3.53–3.71 (2H), 3.79 (1H), 3.89 (1H), 4.11 (1H), 5.17 (1H), 6.48 (1H), 7.09 (1H), 7.23 (1H), 7.61 (1H), 8.60 (1H) ppm.

Example 13f (3S,6R,7S,8S,12E/Z,15S,16E)-1-Hydroxy-3,7,15-tris-[[dimethyl(1,1-dimethylethyl)silyl]oxy]-4,4,8,12,16-pentamethyl-17-(2-pyridyl)-6-(3-(trimethylsilyl)-prop-2-in-1-yl)-heptadeca-12,16-dien-5-one Analogously to Example 1m, 1.95 g (1.89 mmol) of the compound that is produced according to Example 13e is reacted, and after working-up and purification, 1.56 g (1.71 mmol, 90%) of the title compound is isolated as a colorless oil.
$^1$H-NMR (CDCl$_3$): δ=0.00–0.17 (27H), 0.86–0.99 (30H), 1.07–1.78 (8H), 1.11 (3H), 1.26 (3H), 1.60+1.69 (3H), 1.90–2.09 (2H), 2.04 (3H), 2.29 (2H), 2.48 (1H), 2.68 (1H), 3.27 (1H), 3.66 (2H), 3.80 (1H), 4.11 (2H), 5.18 (1H), 6.49 (1H), 7.09 (1H), 7.22 (1H), 7.62 (1H), 8.60 (1H) ppm.

Example 13g (3S,6R,7S,8S,12E/Z,15S,16E)-3,7,15-Tris-[[dimethyl(1,1-dimethylethyl)silyl]oxy]-4,4,8,12,16-pentamethyl-5-oxo-17-(2-pyridyl)-6-(3-(trimethylsilyl)-prop-2-in-1-yl)-heptadeca-12,16-dienal Analogously to Example 1n, 1.56 g (1.71 mmol) of the compound that is produced according to Example 13f is reacted, and after working-up, 1.61 g (max. 1.71 mmol) of the title compound is isolated as a yellow oil, which is further reacted without purification.

Example 13h (3S,6R,7S,8S,12Z,15S,16E)-3,7,15-Tris-[[dimethyl(1,1-dimethylethyl)silyl]oxy]-4,4,8,12,16-pentamethyl-5-oxo-17-(2-pyridyl)-6-(3-(trimethylsilyl)-prop-2-in-1-yl)-heptadeca-12,16-dienoic acid (A) and (3S,6R,7S,8S,12E,15S,16E)-3,7,15-tris-[[dimethyl(1,1-dimethylethyl)silyl]oxy]-4,4,8,12,16-pentamethyl-5-oxo-17-(2-pyridyl)-6-(3-(trimethylsilyl)-prop-2-in-1-yl)-heptadeca-12,16-dienoic acid (B)

The solution of 1.51 g (max. 1.60 mmol) of the compound, produced according to Example 13g, in 57 ml of tert-butanol is mixed with 47 ml of 2-methyl-2-butene, cooled to 2° C., mixed with 12.9 ml of water, 685 mg of sodium dihydrogen phosphate, 1.16 g of sodium chlorite, allowed to heat to 23° C. and stirred for 3 hours. It is poured into saturated sodium thiosulfate solution, diluted with water and extracted several times with ethyl acetate. The combined organic extracts are dried on sodium sulfate, and the residue that is obtained after filtration and removal of the solvent is purified by chromatography on fine silica gel with a gradient system that consists of n-hexane and ethyl acetate. 749 mg (807 μmol, 50%) of title compound A and 579 mg (623 μmol, 39%) of title compound B are isolated in each case as a colorless oil.
$^1$H-NMR (CDCl$_3$) of A: δ=−0.02–0.17 (27H), 0.76–1.72 (6H), 0.88 (27H), 0.94 (3H), 1.10 (3H), 1.29 (3H), 1.68 (3H), 1.91–2.60 (7H), 2.02 (3H), 2.91 (1H), 3.39 (1H), 3.81 (1H), 4.11 (1H), 4.31 (1H), 5.18 (1H), 6.51 (1H), 7.09 (1H), 7.23 (1H), 7.62 (1H), 8.60 (1H) ppm.
$^1$H-NMR (CDCl$_3$) of B: δ 0.00–0.17 (27H), 0.80–0.98 (30H), 0.98–1.68 (6H), 1.08 (3H), 1.30 (3H), 1.60 (3H), 1.83–2.85 (8H), 2.05 (3H), 3.39 (1H), 3.79 (1H), 4.11 (1H), 4.30 (1H), 5.18 (1H), 6.48 (1H), 7.08 (1H), 8.22 (1H), 7.62 (1H), 8.60 (1H) ppm.

Example 13i (3S,6R,7S,8S,12Z,15S,16E)-15-Hydroxy-3,7-bis-[[dimethyl(1,1-dimethylethyl)silyl]oxy]-4,4,8,12,16-pentamethyl-5-oxo-17-(2-pyridyl)-6-(prop-2-in-1-yl)-heptadeca-12,16-dienoic acid Analogously to Example 1e, 726 mg (782 μmol) of compound A that is produced according to Example 13h is reacted, and after working-up, 657 mg (max. 782 μmol) of the title compound is isolated, which is further reacted without purification.

Example 13j (4S,7R,8S,9S,13Z,16S(E))-4,8-Bis-[[dimethyl(1,1-dimethylethyl)-silyl]oxy]-16-(1-methyl-2-(2-pyridyl)ethenyl)-1-oxa-5,5,9,13-tetramethyl-7-(prop-2-in-1-yl)-cyclohexadec-13-ene-2,6-dione Analogously to Example 1q, 657 mg (max. 782 μmol) of the compound that is produced according to Example 13i is reacted, and after working-up and purification, 300 mg (414 μmol, 53%) of the title compound is isolated as a colorless oil.
$^1$H-NMR (CDCl$_3$): δ=−0.08 (3H), 0.10 (3H), 0.15 (3H), 0.19 (3H), 0.81–2.20 (8H), 0.86 (9H), 0.95 (9H), 1.02 (3H), 1.14 (3H), 1.23 (3H), 1.68 (3H), 2.14 (3H), 2.33–2.82 (6H), 3.12 (1H), 4.06 (1H), 4.11 (1H), 5.02 (1H), 5.19 (1H), 6.58 (1H), 7.11 (1H), 7.26 (1H), 7.63 (1H), 8.59 (1H) ppm.

Example 13k (4S,7R,18S,9S,13Z,16S(E))-4,8-Dihydroxy-16-(1-methyl-2-(2-pyridyl)ethenyl)-1-oxa-5,5,9,13-tetramethyl-7-(prop-2-in-1-yl)-cyclohexadec-13-ene-2,6-dione Analogously to Example 1, 140 mg (193 μmol) of the compound that is produced according to Example 13j is reacted, and after working-up and purification, 52 mg (105 μmol, 54%) of the title compound is isolated as a colorless oil.
$^1$H-NMR (CDCl$_3$): δ=1.08 (3H), 1.10 (3H), 1.20–1.92 (6H), 1.42 (3H), 1.68 (3H), 2.02 (1H), 2.08 (3H), 2.22–2.72 (7H), 2.86 (1H), 3.43 (1H), 3.78 (1H), 4.37 (1H), 4.54 (1H), 5.12 (1H), 5.20 (1H), 6.61 (1H), 7.13 (1H), 7.30 (1H), 7.69 (1H), 8.55 (1H) ppm.

Example 14

(4S,7R,8S,9S,13E,16S(E))-4,8-Dihydroxy-16-(1-methyl-2-(2-pyridyl)ethenyl)-1-oxa-5,5,9,13-tetramethyl-7-(prop-2-in-1-yl)-cyclohexadec-13-ene-2,6-dione

Example 14a (3S,6R,7S,8S,12E,15S,16E)-15-Hydroxy-3,7-bis-[[dimethyl(1,1-dimethylethyl)silyl]oxy]-4,4,8,12,16-pentamethyl-5-oxo-17-(2-pyridyl)-6-(prop-2-in-1-yl)-heptadeca-12,16-dienoic acid Analogously to Example 1e, 534 mg (575 μmol) of compound B that is produced according to Example 13h is reacted, and after working-up, 434 mg (max. 585 μmol) of the title compound is isolated, which is further reacted without purification.

Example 14b (4S,7R,8S,9S,13E,16S(E))-4,8-Bis-[[dimethyl(1,1-dimethylethyl)-silyl]oxy]-16-(1-methyl-2-(2-pyridyl)ethenyl)-1-oxa-5,5,9,13-tetramethyl-7-(prop-2-in-1-yl)-cyclohexadec-13-ene-2,6-dione Analogously to Example 1q, 434 mg (max. 585 µmol) of the compound that is produced according to Example 14a is reacted, and after working-up and purification, 382 mg (527 µmol, 90%) of the title compound is isolated as a colorless oil.

$^1$H-NMR (CDCl$_3$): δ=0.04 (3H), 0.07–0.12 (9H), 0.85 (9H), 0.88 (9H), 0.93 (3H), 1.00–2.20 (8H), 1.14 (3H), 1.22 (3H), 1.58 (3H), 2.00 (1H), 2.12 (3H), 2.44–2.62 (5H), 3.19 (1H), 3.91 (1H), 4.41 (1H), 5.19 (1H), 5.29 (1H), 6.53 (1H), 7.09 (1H), 7.18 (1H), 7.62 (1H), 8.59 (1H) ppm.

Example 14c (4S,7R,8S,9S,13Z,16S(E))-4,8-Dihydroxy-16-(1-methyl-2-(2-pyridyl)ethenyl)-1-oxa-5,5,9,13-tetramethyl-7-(prop-2-in-1-yl)-cyclohexadec-13-ene-2,6-dione Analogously to Example 1, 110 mg (152 µmol) of the compound that is produced according to Example 14b is reacted, and after working-up and purification, 48 mg (97 µmol, 64%) of the title compound is isolated as a colorless oil.

$^1$H-NMR (CDCl$_3$): δ=0.89–1.80 (5H), 1.01 (3H), 1.06 (3H), 1.35 (3H), 1.61 (3H), 1.93 (1H), 2.00 (1H), 2.10 (3H), 2.17 (1H), 2.38–2.66 (6H), 3.58 (1H), 3.79 (2H), 3.88 (1H), 4.44 (1H), 5.10 (1H), 5.40 (1H), 6.59 (1H), 7.13 (1H), 7.33 (1H), 7.68 (1H), 8.56 (1H) ppm.

Example 15

(4S,7R,8S,9S,13Z,16S(E))-4,8-Dihydroxy-16-(1-methyl-2-(2-pyridyl)ethenyl)-1-oxa-5,5,9,13-tetramethyl-7-(prop-2-en-1-yl)-cyclohexadec-13-ene-2,6-dione

Example 15a (4S,7R,8S,9S,13Z,16S(E))-4,8-Bis-[[dimethyl(1,1-dimethylethyl)silyl]oxy]-16-(1-methyl-2-(2-pyridyl)ethenyl)-1-oxa-5,5,9,13-tetramethyl-7-(prop-2-en-1-yl)-cyclohexadec-13-ene-2,6-dione (A) and (4S,7R,8S,9S,13Z,16S(RS))-4,8-bis-[[dimethyl(1,1-dimethylethyl)silyl]oxy]-16-(1-methyl-2-(2-pyridyl)ethenyl)-1-oxa-5,5,9,13-tetramethyl-7-(prop-2-en-1-yl)-cyclohexadec-13-ene-2,6-dione (B)

The solution of 150 mg (207 µmol) of the compound, produced according to Example 13j, in 16 ml of ethyl acetate is mixed with a catalytic amount of palladium on barium sulfate, 153 µl of pyridine, and it is hydrogenated at 23° C. under an atmosphere of hydrogen. After filtration and removal of the solvent, the residue is purified by chromatography on fine silica gel with a gradient system that consists of n-hexane and ethyl acetate. In addition to starting material, 66 mg (91 µmol, 44%) of title compound A and 64 mg (88 µmol, 42%) of title compound B are isolated in each case as an isolated oil.

$^1$H-NMR (CDCl$_3$) of A: δ=−0.09 (3H), 0.07 (3H), 0.11 (6H), 0.78–1.82 (7H), 0.84 (9H), 0.92 (9H), 0.98 (3H), 1.09 (3H), 1.18 (3H), 1.67 (3H), 2.06–2.82 (7H), 2.13 (3H), 3.11 (1H), 4.02 (1H), 4.85–5.03 (3H), 5.18 (1H), 5.78 (1H), 6.57 (1H), 7.09 (1H), 7.25 (1H), 7.62 (1H), 8.59 (1H) ppm.

Example 15b (4S,7R,8S,9S,13Z,16S(E))-4,8-Dihydroxy-16-(1-methyl-2-(2-pyridyl)ethenyl)-1-oxa-5,5,9,13-tetramethyl-7-(prop-2-en-1-yl)-cyclohexadec-13-ene-2,6-dione Analogously to Example 1, 65.6 mg (90 mmol) of compound A that is produced according to Example 15a is reacted, and after working-up and purification, 24.6 mg (49 µmol, 55%) of the title compound is isolated as a colorless oil.

$^1$H-NMR (CDCl$_3$): =1.05 (6H), 1.19–1.89 (5H), 1.32 (3H), 1.69 (3H), 2.05 (3H), 2.13–2.57 (6H), 2.64 (1H), 2.82 (1H), 3.33 (1H), 3.71 (2H), 4.34 (1H), 4.62 (1H), 5.01 (1H), 5.05 (1H), 5.12 (1H), 5.19 (1H), 5.75 (1H), 6.60 (1H), 7.12 (1H), 7.29 (1H), 7.68 (1H), 8.52 (1H) ppm.

Example 16

(4S,7R,8S,9S,13E,16S(E))-4,8-Dihydroxy-16-(1-methyl-2-(2-pyridyl)ethenyl)-1-oxa-5,5,9,13-tetramethyl-7-(prop-2-en-1-yl)-cyclohexadec-13-ene-2,6-dione

Example 16a (4S,7R,8S,9S,13E,16S(E))-4,8-Bis-[[dimethyl(1,1-dimethylethyl)silyl]oxy]-16-(1-methyl-2-(2-pyridyl)ethenyl)-1-oxa-5,5,9,13-tetramethyl-7-(prop-2-en-1-yl)-cyclohexadec-13-ene-2,6-dione Analogously to Example 15a, 114 g (157 µmol) of the compound that is produced according to Example 14b is reacted, and after working-up and purification, 68 mg (94 µmol, 60%) of the title compound is isolated as a colorless oil.

$^1$H-NMR (CDCl$_3$): δ=0.04 (3H), 0.08 (3H), 0.10 (3H), 0.13 (3H), 0.83–0.98 (24H), 1.11 (3H), 1.15–1.96 (6H), 1.20 (3H), 2.08–2.65 (7H), 2.14 (3H), 3.03 (1H), 3.88 (1H), 4.31 (1H), 4.98 (1H), 5.02 (1H), 5.22 (1H), 5.29 (1H), 5.79 (1H), 6.54 (1H), 7.09 (1H), 7.20 (1H), 7.62 (1H), 8.60 (1H) ppm.

Example 16b (4S,7R,8S,9S,13E,16S(E))-4,8-Dihydroxy-16-(1-methyl-2-(2-pyridyl)ethenyl)-1-oxa-5,5,9,13-tetramethyl-7-(prop-2-en-1-yl)-cyclohexadec-13-ene-2,6-dione Analogously to Example 1, 67.7 mg (93 µmol) of the compound that is produced according to Example 16a is reacted, and after working-up and purification, 36.8 mg (74 µmol, 80%) of the title compound is isolated as a colorless oil.

$^1$H-NMR (CDCl$_3$) δ 0.96–2.66 (13H), 0.99 (6H), 1.28 (3H), 1.62 (3H), 2.10 (3H), 3.49 (1H), 3.72 (1H), 4.01 (2H), 4.43 (1H), 4.91–5.13 (3H), 5.39 (1H), 5.71 (1H), 6.58 (1H), 7.12 (1H), 7.34 (1H), 7.66 (1H), 8.53 (1H) ppm.

Example 17

(1S/1R,3S(E),7S,11R(RS),11S,12S,16R/S)-7,11-Dihydroxy-10-(2,3-epoxyprop-1-yl)-3-(1-methyl-2-(2-N-oxido-pyridyl)ethenyl)- 8,8,12,16-tetramethyl-4,17-dioxabicyclo[14.1.0]heptadecane-5,9-dione Analogously to Example 10, 36 mg (74 μmol) of the compound that is produced according to Example 16 is reacted, and after working-up and purification, 12 mg (22 μmol, 30%) of a mixture of two diastereomers A and B and 20 mg (37 μmol, 50%) of a mixture of two diastereomers C and D of the title compounds are isolated in each case as a colorless oil.

MS (FAB) m/e=546 (M$^+$+1)

Example 18

(1S,3S(E),7S,10R(R or S),11S,12S,16R)-7,11-Dihydroxy-10-(2,3-epoxyprop-1-yl)-3-(1-methyl-2-(2-N-oxido-pyridyl)ethenyl)-8,8,12,16-tetramethyl-4,17-dioxabicyclo[14.1.0]heptadecane-5,9-dione (A) and (1R,3S(E),7S,10R(R or S),11S,12S,16S)-7,11-dihydroxy-10-(2,3-epoxyprop-1-yl)-3-(1-methyl-2-(2-N-oxido-pyridyl)ethenyl)-8,8,12,16-tetramethyl-4,17-dioxabicyclo[14.1.0]heptadecane-5,9-dione (B)

The solution of 20 mg (37 μmol) of a mixture of compounds C and D, produced according to Example 17, in 3.1 ml of anhydrous trichloromethane is mixed with a molecular sieve (4A), 789 ml of isopropanol, 14.2 mg of tetrapropylammonium perruthenate, and it is stirred for 5 hours at 55° C. under an atmosphere of dry argon. It is concentrated by evaporation, and the crude product that is obtained is purified by chromatography on analytical thin-layer plates. As a mobile solvent, a mixture of ethanol and ethyl acetate is used; as an eluant, a mixture of dichloromethane and ethanol is used. 4.6 mg (8.7 μmol, 23%) of title compound A or B and 3.3 mg (6.2 μmol, 17%) of title compound B or A are isolated in each case as a colorless oil.

$^1$H-NMR (CDCl$_3$) of A or B: δ=0.96 (3H), 1.06 (3H), 1.12–2.03 (11H), 1.22 (3H), 1.30 (3H), 2.11 (3H), 2.22 (1H), 2.58 (2H), 2.76 (1H), 3.44 (1H), 3.52 (1H), 3.73–3.91 (2H), 4.08–4.21 (2H), 4.47 (1H), 5.59 (1H), 6.59 (1H), 7.11 (1H), 7.23 (1H), 7.63 (1H), 8.59 (1H) ppm.

$^1$H-NMR (CDCl$_3$) of B or A: δ=0.96 (3H), 1.05 (3H), 1.11–1.96 (9H), 1.23 (3H), 1.31 (3H), 2.12 (3H), 2.19–2.35 (3H), 2.50–2.66 (2H), 2.78 (1H), 3.50–3.69 (3H), 3.93 (1H), 4.16 (1H), 4.25 (1H), 4.41 (1H), 5.59 (1H), 6.60 (1H), 7.12 (1H), 7.22 (1H), 7.64 (1H), 8.59 (1H) ppm.

Example 19

(1S/R,3S(E),7S,10R(S or R),11S,12S,16R/S)-7,11-Dihydroxy-10-(2,3-epoxyprop-1-yl)-3-(1-methyl-2-(2-N-oxido-pyridyl)ethenyl)-8,8,12,16-tetramethyl-4,17-dioxabicyclo[14.1.0]heptadecane-5,9-dione Analogously to Example 18, 6.3 mg (12 μmol) of compounds A and B that are produced according to Example 17 is reacted, and after working-up and purification, 2.4 mg (4.5 μmol, 38%) of a mixture of the title compounds is isolated as a colorless oil.

$^1$H-NMR (CDCl$_3$): δ=0.95–2.22 (11H), 1.01 (3H), 1.10 (3H), 1.27 (3H), 1.31 (3H), 2.11 (3H), 2.34 (1H), 2.45–2.57 (2H), 2.90 (1H), 3.39–3.87 (4H), 4.01–4.37 (3H), 5.49 (1H), 6.62 (1H), 7.13 (1H), 7.24 (1H), 7.66 (1H), 8.58 (1H) ppm.

Example 20

(4S,7R,8S,9S,13Z,16S(R or S))-4,8-Dihydroxy-16-(1-methyl-2-(2-pyridyl)ethyl)-1-oxa-5,5,9,13-tetramethyl-7-(prop-2-en-1-yl)-cyclohexadec-13-ene-2,6-dione (A) and (4S,7R,8S,9S,13Z,16S(S or R))-4,8-dihydroxy-16-(1-methyl-2-(2-pyridyl)ethyl)-1-oxa-5,5,9,13-tetramethyl-7-(prop-2-en-1-yl)-cyclohexadec-13-ene-2,6-dione (B)

Analogously to Example 1, 7.0 mg (9.6 μmol) of compounds B that are produced according to Example 15a is reacted, and after working-up and purification, 1.4 mg (2.8 μmol, 29%) of title compound A and 1.7 mg (3.4 μmol, 35%) of title compound B are isolated in each case as a colorless oil.

$^1$H-NMR (CDCl$_3$) of A: δ=0.88 (1H), 0.92 (3H), 1.04 (3H), 1.07 (3H), 1.18–2.57 (14H), 1.30 (3H), 1.68 (3H), 2.91 (1H), 3.17 (1H), 3.28 (1H), 3.68 (1H), 4.47 (1H), 4.91–5.10 (4H), 5.70 (1H), 7.13–7.22 (2H), 7.68 (2H), 8.46 (1H) ppm.

$^1$H-NMR (CDCl$_3$) of B: δ=1.00 (6H), 1.05 (3H), 1.10–2.59 (15H), 1.33 (3H), 1.63 (3H), 2.93 (1H), 3.11 (1H), 3.28 (1H) 3.63 (1H), 4.44 (1H), 4.91–5.12 (4H), 5.79 (1H), 6.39 (1H), 7.18 (2H), 7.67 (1H), 8.46 (1H) ppm.

Example 21

(4S,7R,8S,9S,13Z,16S)-4,8-Dihydroxy-16-(2-methyl-benzoxazol-5-yl)-1-oxa-5,5,9,13-tetramethyl-7-(prop-2-en-1-yl)-cyclohexadec-13-ene-2,6-dione

Example 21a (2E/Z)-3-(2-Methyl-benzoxazol-5-yl)-2-propenoic acid ethyl ester The suspension of 58 g (346 mmol) of 5-chloro-2-methylbenzoxazole, 200 ml of dimethylformamide, 57 g of sodium iodide and 16.2 g of nickel(II) bromide is heated for 4 hours to 150° C. After cooling, it is mixed with 42 ml of acrylic acid ethyl ester, 53 ml of triethylamine, 998 mg of tris-(dibenzylidene acetone)-dipalladium (O), 36.4 g of triphenylphosphine, and it is heated for three days to 150° C. The cooled mixture is poured into water, acidified and extracted several times with ethyl acetate. The combined organic extracts are washed with saturated sodium chloride solution, dried on sodium sulfate, and the residue that is obtained after filtration and removal of the solvent is purified by chromatography on fine silica gel with a gradient system that consists of n-hexane and ethyl acetate. 6.4 g (28 mmol, 8%) of the title compound is isolated as a crystalline solid.

$^1$H-NMR (CDCl$_3$): δ=1.33 (3H), 2.64 (3H), 4.28 (2H), 6.42 (1H), 7.47 (2H), 7.78 (1H), 7.81 (1H) ppm.

Example 21b (2-Methylbenzoxazol-5-yl)-carbaldehyde

The solution of 9.5 g (41 mmol) of the compound, produced according to Example 21a, in ml of tetrahydrofuran, is mixed with ml of water, ml of a 2.5% solution of osmium tetroxide in tert-butanol, g of sodium periodate, and it is stirred for 6 hours at 23° C. It is poured onto saturated sodium thiosulfate solution and extracted several times with ethyl acetate. The combined organic extracts are washed with saturated sodium chloride solution, dried on sodium sulfate, and the residue that is obtained after filtration and removal of the solvent is purified by chromatography on fine silica gel with a gradient system that consists of n-hexane and ethyl acetate. 4.86 g (30 mmol, 74%) of the title compound is isolated as a crystalline solid.

$^1$H-NMR (CDCl$_3$): δ=2.69 (3H), 7.60 (1H), 7.90 (1H), 8.16 (1H), 10.08 (1H) ppm.

Example 21c (3RS)-3-(2-Methyl-benzoxazol-5-yl)-1-[(4S,5R)-4-methyl-5-phenyl-oxazolidin-2-on-3-yl]-3-hydroxypropyl-1-one 50 ml of a 2.4 molar solution of n-butyllithium in n-hexane is added in drops at −30° C. under an atmosphere of dry argon to the solution of 14.1 ml of diisopropylamine in 670 ml of anhydrous tetrahydrofuran, it is stirred for 20 minutes, cooled to −70° C. and mixed within 4.5 hours with the solution of 19.8 g (4S,5R)-3-acetyl-4-methyl-5-phenyloxazolidin-2-one in 670 ml of tetrahydrofuran. After 1 hour, the solution of 4.86 g (30.1 mmol) of the compound, produced according to Example 21b, in 175 ml of tetrahydrofuran is added in drops within 1.5 hours, and it is stirred for 1 hour at −70° C. It is poured onto a saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 11.3 g (29.7 mmol, 98%) of the title compound is isolated as a colorless oil.

Example 21d (3S)-3-(2-Methyl-benzoxazol-5-yl)-1-[([(4S,5R)-4-methyl-5-phenyl-oxazolidin-2-on-3-yl]-3-[[dimethyl(1,1-dimethylethyl)silyl]oxy]-propyl-1-one (A) and (3R)-3-(2-methyl-benzoxazol-5-yl)-1-[(4S,5R)-4-methyl-5-phenyl-oxazolidin-2-on-3-yl]-3-[(dimethyl(1,1-dimethylethyl)silyl]oxy]-propyl-1-one (B)

The solution of 12.5 g (32.8 mmol) of the compound, produced according to Example 21c, in 110 ml of anhydrous dichloromethane is cooled under an atmosphere of dry argon to −70° C., mixed with 7.8 ml of 2,6-lutidine and 13.9 ml of trifluoromethanesulfonic acid-tert-butyldimethylsilylester, and it is stirred for 1 hour. It is poured onto a saturated sodium bicarbonate solution, extracted several times with dichloromethane, the combined organic extracts are washed with saturated sodium chloride solution and dried on sodium sulfate. The residue that is obtained after filtration and removal of the solvent is separated by chromatography on fine silica gel with a gradient system that consists of n-hexane, ethyl acetate and ethanol. 8.9 g (18.0 mmol, 55%) of title compound A is isolated as a crystalline solid, and 2.9 g (5.9 mmol, 18%) of title compound B is isolated as a colorless oil.

$^1$H-NMR (CDCl$_3$) of A: δ=−0.19 (3H), 0.02 (3H), 0.82 (9H), 0.88 (3H), 2.61 (3H), 3.19 (1H), 3.51 (1H), 4.69 (1H), 5.36 (1H), 5.55 (1H), 7.21–7.44 (7H), 7.64 (1H) ppm.

$^1$H-NMR (CDCl$_3$) of B: δ=−0.19 (3H), 0.04 (3H), 0.85 (9H), 0.88 (3H), 2.63 (3H), 3.04 (1H), 4.67 (1H), 4.77 (1H), 5.39 (1H), 5.63 (1H), 7.21–7.46 (7H), 7.67 (1H) ppm.

Example 21e (3S)-3-(2-Methyl-benzoxazol-5-yl)-3-[[dimethyl(1,1-dimethylethyl)silyl]oxy]-propionic acid ethyl ester The solution of 13.9 g (28.2 mmol) of the compound, produced according to Example 21d, in 140 ml of anhydrous ethanol is mixed at 23° C. under an atmosphere of dry argon with 7.1 ml of titanium tetraethylate, and it is heated for 3 hours to 85° C. It is concentrated by evaporation, and the residue is purified by chromatography on fine silica gel with a gradient system that consists of n-hexane and ethyl acetate. 10.1 g (27.8 mmol, 99%) of the title compound is isolated as a colorless oil.

$^1$H-NMR (CDCl$_3$): δ=−0.20 (3H), 0.02 (3H), 0.82 (9H), 1.26 (3H), 2.55 (1H), 2.62 (3H), 2.76 (1H), 4.12 (2H), 5.26 (1H), 7.29 (1H), 7.40 (1H), 7.62 (1H) ppm.

Example 21f (3S)-3-(2-Methyl-benzoxazol-5-yl)-3-[[dimethyl(1,1-dimethylethyl)silyl]oxy]-propan-1-ol The solution of 10.1 g (27.8 mmol) of the compound, produced according to Example 21e, in ml of anhydrous dichloromethane, is cooled under an atmosphere of dry argon to −78° C., mixed with 58 ml of a 1.2 molar solution of diisobutylaluminum hydride in toluene, and it is stirred for 1 more hour. It is mixed with 16 ml of isopropanol, 32 ml of water, allowed to heat to 23° C. and stirred until a fine-grained precipitate has formed. After filtration and removal of the solvent, 7.2 g (22.4 mmol, 81%) of the title compound is isolated as a colorless oil.

$^1$H-NMR (CDCl$_3$): δ=−0.18 (3H), 0.07 (3H), 0.89 (9H), 1.97 (2H), 2.35 (1H), 2.66 (3H), 3.73 (2H), 5.06 (1H), 7.28 (1H), 7.42 (1H), 7.60 (1H) ppm.

Example 21g (3S)-3-(2-Methyl-benzoxazol-5-yl)-[[dimethyl(1,1-dimethylethyl)silyl]oxy]-1-iodo-propane The solution of 2.83 g of triphenylphosphine in 40 ml of anhydrous dichloromethane is mixed at 23° C. under an atmosphere of dry argon with 737 mg of imidazole, 2.71 g of iodine, and the solution of 2.65 g (8.2 mmol) of the compound, produced according to Example 21f, in 30 ml of dichloromethane, is added in drops while being cooled. It is stirred for 1 hour and purified directly by chromatography on fine silica gel with a gradient system that consists of n-hexane and ethyl acetate. 2.3 g (5.3 mmol, 65%) of the title compound is isolated as a colorless oil.

$^1$H-NMR (CDCl$_3$) δ=−0.20 (3H), 0.06 (3H), 0.85 (9H), 2.10 (1H), 2.21 (1H), 2.61 (3H), 3.11 (1H), 3.23 (1H), 4.82 (1H), 7.22 (1H), 7.39 (1H), 7.59 (1H) ppm.

Example 21h (3S)-3-(2-Methyl-benzoxazol-5-yl)-3-[[dimethyl(1,1-dimethylethyl)silyl]oxy]-propane-1-triphenylphosphonium iodide 2.3 g (5.3 mmol) of the compound that is produced according to Example 21g is mixed with 2.9 ml of ethyldiisopropylamine, 17.5 g of triphenylphosphine, and it is heated for 4 hours to 85° C. The oily residue is purified by chromatography on fine silica gel with a gradient system that consists of n-hexane and ethyl acetate. 3.3 g (4.8 mmol, 89%) of the title compound is isolated as a crystalline solid.

$^1$H-NMR (CDCl$_3$): =−0.19 (3H), 0.12 (3H), 0.84 (9H), 1.89 (1H), 2.09 (1H), 2.60 (3H), 3.41. (1H), 4.06 (1H), 5.37 (1H), 7.38 (1H), 7.49 (1H), 7.59 (1H), 7.62–7.84 (15H) ppm.

Example 21i (2S,6E/Z,9S)-9-[[Dimethyl(1,1-dimethylethyl)silyl]oxy]-9-(2-methyl-benzoxazol-5-yl)-1-(tetrahydropyran-2-yloxy)-2,6-dimethyl-non-6-ene The solution of 2.3 g (3.3 mmol) of the compound, produced according to Example 21h, in 15 ml of anhydrous tetrahydrofuran is mixed under an atmosphere of dry argon at 0° C. with 5 ml of a 1.0 molar solution of sodium hexamethyldisilazane in tetrahydrofuran, the solution of 513 mg (2.25 mmol) of (2S)-2-methyl-6-oxo-heptane-1-(tetrahydropyran-2-yloxy), which was produced analogously to the process described in DE 197 51 200.3, is added in drops in 15 ml of tetrahydrofuran, allowed to heat to 23° C. and reacted for 3 more hours. It is poured onto a saturated ammonium chloride solution, extracted several times with ethyl acetate, the combined organic extracts are washed with saturated sodium chloride solution and dried on sodium sulfate. The residue that is obtained after filtration and removal of the solvent is separated by chromatography on fine silica gel with a gradient system that consists of n-hexane and ethyl acetate. 506 mg (1.0 mmol, 44%) of the title compound is isolated as a colorless oil.

$^1$H-NMR (CDCl$_3$) δ=−0.15 (3H), 0.01 (3H), 0.80–0.92 (12H), 1.02 (1H), 1.19–1.97 (12H), 1.46+1.62 (3H), 2.21–2.48 (2H), 2.60 (3H), 3.10+3.19 (1H), 3.40–3.61 (2H), 3.82 (1H), 4.53 (1H), 4.69 (1H), 5.11 (1H), 7.22 (1H), 7.37 (1H), 7.57 (1H) ppm.

Example 21j (2S,6E/Z,9S)-9-[[Dimethyl(1,1-dimethylethyl)silyl]oxy]-9-(2-methyl-benzoxazol-5-yl)-1-hydroxy-2,6-dimethyl-non-6-ene Analogously to Example 1k, 447 mg (0.87 mmol) of the compound that is produced according to Example 21i is reacted, and after working-up and purification, 298 mg (0.69 mmol, 79%) of the title compound is isolated as a colorless oil.

$^1$H-NMR (CDCl$_3$): δ=−0.12 (3H), 0.01 (3H), 0.82–0.92 (12H), 1.01 (1H), 1.16–1.67 (4H), 1.44+1.63 (3H), 1.83–1.98 (2H), 2.18 (1H), 2.33 (1H), 2.44 (1H), 2.62 (3H), 3.31–3.53 (2H), 4.71 (1H), 5.07+5.13 (1H), 7.24+7.29 (1H), 7.39 (1H), 7.53+7.58 (1H) ppm.

Example 21k (2S,6E/Z,9S)-9-[[Dimethyl(1,1-dimethylethyl)silyl]oxy]-9-(2-methyl-benzoxazol-5-yl)-1-oxo-2,6-dimethyl-non-6-ene Analogously to Example 1n, 272 mg (0.63 mmol) of the compound that is produced according to Example 21j is reacted, and after working-up and purification, 236 mg (0.55 mmol, 87%) of the title compound is isolated as a colorless oil.

$^1$H-NMR (CDCl$_3$): δ=−0.16 (3H), 0.01 (3H), 0.84 (9H) 1.02+1.05 (3H), 1.13–2.50 (9H), 1.44+1.61 (3H), 2.61 (3H), 4.71 (1H), 5.13 (1H), 7.21 (1H), 7.37 (1H), 7.55 (1H), 9.54 (1H) ppm.

Example 21l (4S(4R,5S,6S,10E/Z,13S))-4-(13-[[(1,1-Dimethylethyl)dimethylsilyl]oxy]-4-(prop-2-en-1-yl)-13-(2-methyl-benzoxazol-5-yl)-3-oxo-5-hydroxy-2,6,10-trimethyl-tridec-10-en-2-yl)-2,2-dimethyl-[1,3]dioxane (A) and (4S(4S,5R,6S,10E/Z,13S))-4-(13-[[(1,1-dimethylethyl)dimethylsilyl]oxy]-4-(prop-2-en-1-yl)-13-(2-methyl-benzoxazol-5-yl)-3-oxo-5-hydroxy-2,6,10-trimethyl-tridec-10-en-2-yl)-2,2-dimethyl-[1,3]dioxane (B)

Analogously to Example 1c, 236 mg (0.55 mmol) of the compound that is produced according to Example 21k is reacted with 433 mg (1.80 mmol) of (4S)-4-(2-methyl-3-oxo-hept-6-en-2-yl)-2,2-dimethyl-[1,3]dioxane, which was produced analogously to the process that is described in DE 197 51 200.3, and after working-up and purification, in addition to starting material, 221 mg (0.33 mmol, 60%) of title compound A and 72 mg (0.11 mmol, 20%) of title compound B are isolated in each case as a colorless oil.

$^1$H-NMR (CDCl$_3$) of A: δ=−0.13 (3H), 0.01 (3H), 0.78–0.88 (12H), 0.96 (3H), 1.04 (1H), 1.11–2.52 (12H), 1.23 (3H), 1.31 (3H), 1.39 (3H), 1.47+1.64 (3H), 2.62 (3H), 2.90+2.98 (1H), 3.32 (1H), 3.47 (1H), 3.87 (1H), 3.97 (1H), 4.13 (1H), 4.70 (1H), 4.98 (1H), 5.03 (1H), 5.12 (1H), 5.71 (1H), 7.22 (1H), 7.38 (1H), 7.56 (1H) ppm.

Example 21m (3S,6R,7S,8S,12E/Z,15S)-15-[[(1,1-Dimethylethyl)dimethylsilyl]oxy]-6-(prop-2-en-1-yl)-1,3,7-trihydroxy-4,4,8,12-tetramethyl-15-(2-methyl-benzoxazol-5-yl)-pentadec-12-en-5-one Analogously to Example 1k, 221 mg (0.33 mmol) of compound A that is produced according to Example 21l is reacted, and after working-up and purification, 163 mg (0.26 mmol, 78%) of the title compound is isolated as a colorless oil.

$^1$H-NMR (CDCl$_3$): δ=−0.15 (3H), 0.01 (3H), 0.79–0.90 (12H), 1.05 (3H), 1.17–2.59 (13H), 1.20+1.24 (3H), 1.43+1.62 (3H), 2.62+2.64 (0.3H), 2.81+3.07 (1H), 3.25–3.70 (3H), 3.86 (2H), 4.08 (2H), 4.68 (1H), 4.92–5.19 (3H), 5.69 (1H), 7.25+7.29 (1H), 7.39 (1H), 7.48+7.52 (1H) ppm.

Example 21n (3S,6R,7S,8S,12E/Z,15S)-6-(Prop-2-en-1-yl)-1,3,7,15-tetrakis-[[(1,1-dimethylethyl)dimethylsilyl]oxy]-4,4,8,12-tetramethyl-15-(2-methyl-benzoxazol-5-yl)-pentadec-12-en-5-one Analogously to Example 1l, 163 mg (0.26 mmol) of the compound that is produced according to Example 21m is reacted, and after working-up and purification, 236 mg (0.24 mmol, 93%) of the title compound is isolated as a colorless oil.

¹H-NMR (CDCl₃): δ=−0.06 (3H), −0.04–0.08 (21H), 0.79–0.93 (39H), 0.96–1.66 (7H), 1.01 (3H), 1.17 (3H), 1.47+1.62 (3H), 1.88 (2H), 2.18–2.52 (4H), 2.61 (3H), 3.11 (1H), 3.53 (1H), 3.63 (1H), 3.73 (1H), 3.84 (1H), 4.68 (1H), 4.91 (1H), 4.97 (1H), 5.12 (1H), 5.72 (1H), 7.21 (1H), 7.36 (1H), 7.56 (1H) ppm.

Example 21o (3S,6R,7S,8S,12E/Z,15S)-1-Hydroxy-6-(prop-2-en-1-yl)-3,7,15-tris-[[(1,1-dimethylethyl)dimethylsilyl]oxy]-4,4,8,12-tetramethyl-15-(2-methyl-benzoxazol-5-yl)-pentadec-12-en-5-one Analogously to Example 1m, 236 mg (0.24 mmol) of the compound that is produced according to Example 21n is reacted, and after working-up and purification, 146 mg (0.17 mmol, 71%) of the title compound is isolated as a colorless oil.

Example 21p (3S,6R,7S,8S,12E/Z,15S)-5-Oxo-6-(prop-2-en-1-yl)-3,7,15-tris-[[(1,1-dimethylethyl)dimethylsilyl]oxy]-4,4,8,12-tetramethyl-15-(2-methyl-benzoxazol-5-yl)-pentadec-12-enal Analogously to Example 1n, 146 mg (0.17 mmol) of the compound that is produced according to Example 21o is reacted, and after working-up and purification, 143 mg (0.17 mmol, 98%) of the title compound is isolated as a colorless oil.

Example 21q (3S,6R,7S,8S,12Z, 15S)-5-Oxo-6-(prop-2-en-1-yl)-3,7,15-tris-[[(1,1-dimethylethyl)dimethylsilyl]oxy]-4,4,8,12-tetramethyl-5-(2-methyl-benzoxazol-5-yl)-pentadec-12-enoic acid (A) and (3S,6R,7S,8S,12E, 15S)-5-oxo-6-(prop-2-en-1-yl)-3,7,15-tris-[[(1,1-dimethylethyl)dimethylsilyl]oxy]-4,4,8,12-tetramethyl)-15-(2-methyl-benzoxazol-5-yl)-pentadec-12-enoic acid (B)

The solution of 143 mg (0.17 mmol) of the compound, produced according to Example 21p, in 5 ml of tert-butanol is mixed at 0° C. with the solution of 1.1 ml of 2-methyl-2-butene in 3.6 ml of tetrahydrofuran, 1.3 ml of water, 67 mg of sodium dihydrogen phosphate, 117 mg of sodium chlorite, and it is stirred for 2 hours. It is poured onto a saturated sodium thiosulfate solution, extracted several times with ethyl acetate, the combined organic extracts are washed with saturated sodium chloride solution and dried on sodium sulfate. The residue that is obtained after filtration and removal of the solvent is separated by chromatography on fine silica gel with a gradient system that consists of n-hexane and ethyl acetate. 58 mg (66 mmol, 39%) of title compound A and 52 mg (60 μmol, 35%) of title compound B are isolated in each case as a colorless oil.

¹H-NMR (CDCl₃) of A: δ=−0.13 (3H), −0.02 (6H), 0.04 (6H), 0.12 (3H), 0.80–0.92 (27H), 0.96 (3H), 1.06 (3H), 1.09–1.96 (7H), 1.15 (3H), 1.70 (3H), 2.13–2.60 (7H), 2.62 (3H), 3.20 (1H), 3.66 (1H), 4.43 (1H), 4.72 (1H), 4.92 (1H), 4.99 (1H), 5.26 (1H), 5.70 (1H), 7.34 (1H), 7.40 (1H), 7.89 (1H) ppm.

¹H-NMR (CDCl₃) of B: δ=−0.11 (3H), 0.02 (6H), 0.07 (3H), 0.10 (3H), 0.16 (3H), 0.86–0.94 (30H), 0.90–2.05 (8H), 1.12 (3H), 1.19 (3H), 1.39 (3H), 2.23–2.60 (6H), 2.63 (3H), 3.21 (1H), 3.79 (1H), 4.36 (1H), 4.68 (1H), 4.98 (1H), 5.01 (1H), 5.10 (1H), 5.77 (1H), 7.36 (1H), 7.41 (1H), 7.54 (1H) ppm.

Example 21r (3S,6R,7S,8S,12Z,15S)-15-Hydroxy-5-oxo-6-(prop-2-en-1-yl)-3,7-bis-[[(1,1-dimethylethyl)dimethylsilyl]oxy]-4,4,8,12-tetramethyl-15-(2-methyl-benzoxazol-5-yl)-pentadec-12-enoic acid Analogously to Example 1p, 58 mg (66 μmol) of compound A that is produced according to Example 21q is reacted, and after working-up, 52 mg (max. 66 μmol) of the title compound is isolated, which is further reacted without purification.

Example 21s (4S,7R,8S,9S,13Z 16S)-4,8-Bis-[[dimethyl(1,1-dimethylethyl)silyl]oxy]-16-(2-methyl-benzoxazol-5-yl)-7-(prop-2-en-1-yl)-1-oxa-5,5,9,13-tetramethyl-cyclohexadec-13-ene-2,6-dione Analogously to Example 1q, 52 mg (max. 66 μmol) of the compound that is produced according to Example 21r is reacted, and after working-up and purification, 42 mg (57 μmol, 86%) of the title compound is isolated as a colorless oil.

¹H-NMR (CDCl₃): δ=−0.08 (3H), 0.09 (6H), 0.14 (3H), 0.77–1.88 (7H), 0.85 (9H), 0.93 (9H), 1.01 (3H), 1.09 (3H), 1.15 (3H), 1.71 (3H), 2.10–2.75 (6H), 2.62 (3H), 2.91 (1H), 3.11 (1H), 4.00 (1H), 4.92 (1H), 4.99 (1H), 5.19 (1H), 5.57 (1H), 5.79 (1H), 7.32 (1H), 7.44 (1H), 7.68 (1H) ppm.

Example 21t (4S,7R,8S,9S,13Z,16S)-4,8-Dihydroxy-16-(2-methyl-benzoxazol-5-yl)-7-(prop-2-en-1-yl)-1-oxa-5,5,9,13-tetramethyl-cyclohexadec-13-ene-2,6-dione Analogously to Example 1, 42 mg (57 μmol) of the compound that is produced according to Example 21s is reacted, and after working-up and purification, 19 mg (37 μmol, 65%) of the title compound is isolated as a colorless oil.

¹H-NMR (CDCl₃): δ=1.02 (3H), 1.08 (3H), 1.14–1.97 (6H), 1.22 (3H), 1.70 (3H), 2.22–2.60 (7H), 2.62 (3H), 2.78–2.95 (2H), 3.36 (1H), 3.78 (1H), 4.10 (1H), 5.03 (1H), 5.09 (1H), 5.19 (1H), 5.76 (1H), 5.85 (1H), 7.28 (1H), 7.43 (1H), 7.63 (1H) ppm.

Example 22

(4S,7R,8S,9S,13E,16S)-4,8-Dihydroxy-16-(2-methyl-benzoxazol-5-yl)-7-(prop-2-en-1-yl)-1-oxa-5,5,9,13-tetramethyl-cyclohexadec-13-ene-2,6-dione

Example 22a (3S,6R,7S,8S,12E,15S)-15-Hydroxy-5-oxo-6-(prop-2-en-1-yl)-3,7-bis-[[(1,1-dimethylethyl)dimethylsilyl]oxy]-4,4,8,12-tetramethyl-15-(2-methyl-benzoxazol-5-yl)-pentadec-12-enoic acid Analogously to Example 1p, 52 mg (60 µmol) of compound B that is produced according to Example 21q is reacted, and after working-up, 46 mg (max. 60 µmol) of the title compound is isolated, which is further reacted without purification.

Example 22b (4S,7R,8S,9S,13E,16S)-4,8-Bis-[[dimethyl(1,1-dimethylethyl)silyl]oxy]-16-(2-methyl-benzoxazol-5-yl)-7-(prop-2-en-1-yl)-1-oxa-5,5,9,13-tetramethyl-cyclohexadec-13-ene-2,6-dione Analogously to Example 1q, 46 mg (max. 60 µmol) of the compound that is produced according to Example 22a is reacted, and after working-up and purification, 32 mg (43 µmol, 72%) of the title compound is isolated as a colorless oil.

$^1$H-NMR (CDCl$_3$): δ=0.03–0.11 (12H), 0.89 (9H), 0.91 (9H), 0.94–1.96 (6H), 0.98 (3H), 1.12 (3H), 1.21 (3H), 1.59 (3H), 2.10–2.76 (7H), 2.63 (3H), 3.08 (1H), 3.91 (1H), 4.31 (1H), 5.02 (1H), 5.07 (1H), 5.29 (1H), 5.79 (1H), 5.89 (1H), 7.30 (1H), 7.42 (1H), 7.62 (1H) ppm.

Example 22c (4S,7R,8S,9S,13E,16S)-4,8-Dihydroxy-16-(2-methyl-benzoxazol-5-yl)-7-(prop-2-en-1-yl)-1-oxa-5,5,9,13-tetramethyl-cyclohexadec-13-ene-2,6-dione Analogously to Example 1, 32 mg (43 µmol) of the compound that is produced according to Example 22b is reacted, and after working-up and purification, 15 mg (29 µmol, 68%) of the title compound is isolated as a colorless oil.

$^1$H-NMR (CDCl$_3$): δ=0.99 (3H), 1.02 (3H), 1.27 (3H), 1.38–1.99 (6H), 1.64 (3H), 2.18 (1H), 2.23–2.76 (6H), 2.62 (3H), 3.34 (1H), 3.49 (2H), 3.75 (1H), 4.32 (1H), 4.96–5.08 (3H), 5.73 (1H), 5.98 (1H), 7.23 (1H), 7.42 (1H), 7.67 (1H) ppm.

Example 23

(4S,7R,8S,9S,13Z,16S(Z))-4,8-Dihydroxy-16-(1-fluoro-2-(2-methylthiazol-4-yl)ethenyl)-7-(prop-2-in-1-yl)-1-oxa-5,5,9,13-tetramethyl-cyclohexadec-13-ene-2,6-dione

Example 23a (4S(4R,5S,6S,10E/Z,13S,14Z))-4-(13-[[(1,1-Dimethylethyl)dimethylsilyl]oxy]-4-(prop-2-in-1-yl)-14-fluoro-15-(2-methylthiazol-4-yl)-3-oxo-5-hydroxy-2,6,10-trimethyl-pentadeca-(10,14-dien-2-yl)-2,2-dimethyl-[1,3]dioxane (A) and (4S(4S,5R,6S,10E/Z,13S,14Z))-4-(13-[[(1,1-dimethylethyl)dimethylsilyl]oxy]-4-(prop-2-in-1-yl)-14-fluoro-15-(2-methylthiazol-4-yl)-3-oxo-5-hydroxy-2,6,10-trimethyl-pentadeca-10,14-dien-2-yl)-2,2-dimethyl-[1,3]dioxane (B)

Analogously to Example 1c, 2.89 g (6.57 mmol) of (2S,6E/Z,9S,10Z)-9-[[dimethyl(1,1-dimethylethyl)silyl]oxy]-10-fluoro-11-(2-methyl-4-thiazolyl)-2,6-dimethylundeca-6,10-dienal, which was produced analogously to the process that is described in DE 19907480.1, is reacted with 5.09 g (16.4 mmol) of (4S)-4-(2-methyl-3-oxo-7-trimethylsilyl-hept-6-in-2-yl)-2,2-dimethyl-[1,3]dioxane, which was produced according to the process described in DE 19751200.3, and after working-up and purification, in addition to starting material, 3.26 g (4.35 µmol, 66%) of title compound A as well as 602 mg (0.80 mmol, 12%) of title compound B are isolated in each case as a colorless oil.

$^1$H-NMR (CDCl$_3$) of A: δ=0.03–0.13 (15H), 0.82–0.92 (12H), 0.97–2.08 (12H), 1.06 (3H), 1.30 (6H), 1.38 (3H), 1.58+1.65 (3H), 2.33–2.47 (3H), 2.55 (1H), 2.70 (3H), 3.44 (1H), 3.52 (1H), 3.80–4.28 (2H), 5.13 (1H), 6.03 (1H), 7.32 (1H) ppm.

$^1$H-NMR (CDCl$_3$) of B: δ=0.05–0.65 (15H), 0.88–0.99 (12H), 1.02–1.73 (8H), 1.18 (6H), 1.32 (3H), 1.41 (3H), 1.60+1.69 (3H), 1.90–2.08 (2H), 2.33–2.58 (4H), 2.70 (3H), 3.43 (1H), 3.60 (1H), 3.79–4.26 (4H), 5.18 (1H), 6.05 (1H), 7.33 (1H) ppm.

Example 23b (3S,6R,7S,8S,12E/Z,15S,16Z)-15-[[(1,1-Dimethylethyl)dimethylsilyl]oxy]-6-(3-(trimethylsilyl)-prop-2-in-1-yl)-16-fluoro-1,3,7-trihydroxy-4,4,8,12-tetramethyl-17-(2-methylthiazol-4-yl)-heptadeca-12,16-dien-5-one Analogously to Example 1k, 3.26 g (4.35 mmol) of compound A that is produced according to Example 23a is reacted, and after working-up and purification, in addition to starting material, 2.44 g (3.43 µmol, 79%) of the title compound is isolated as a colorless oil.

$^1$H-NMR (CDCl$_3$): =0.03–0.15 (15H), 0.85–0.95 (12H), 0.98–2.08 (8H), 1.14 (3H), 1.26 (3H), 1.58+1.67 (3H), 2.31–2.49 (3H), 2.59–2.76 (2H), 2.72 (3H), 2.89 (1H), 3.06 (1H), 3.42 (1H), 3.47 3.58 (2H), 3.88 (2H), 4.08–4.22 (2H), 5.11+5.18 (1H), 5.98 (1H), 7.33 (1H) ppm.

Example 23c (3S,6R,7S,8S,12E/Z,15S,16Z)-16-Fluoro-1,3,7,15-tetrakis-[[(1,1-dimethylethyl)dimethylsilyl]oxy]-6-(3-(trimethylsilyl)-prop-2-in-1-yl)-4,4,8,12-tetramethyl-17-(2-methylthiazol-4-yl)-heptadeca-12,16-dien-5-one Analogously to Example 1l, 2.77 g (3.90 mmol) of the compound that is produced according to Example 23b is reacted, and after working-up and purification, 3.48 g (3.31 mmol, 85%) of the title compound is isolated as a colorless oil.

$^1$H-NMR (CDCl$_3$): δ=0.00–0.15 (33H), 0.83–0.97 (39H), 1.00–1.75 (7H), 1.07 (3H), 1.27 (3H), 1.60+1.68 (3H), 1.88–2.03 (2H), 2.31–2.48 (2H), 2.51 (2H), 2.70 (3H), 3.29 (1H), 3.52–3.71 (2H), 3.29 (1H), 3.89 (1H), 4.19 (1H), 5.15 (1H), 6.06 (1H), 7.33 (1H) ppm.

Example 23d (3S,6R,7S,8S,12E/Z,15S,16Z)-16-Fluoro-1-hydroxy-3,7,15-tris-[[(1,1-dimethylethyl)dimethylsilyl]oxy]-6-(3-(trimethylsilyl)-prop-2-in-1-yl)-4,4,8,12-tetramethyl-17-(2-methylthiazol-4-yl)-heptadeca-12,16-dien-5-one Analogously to Example 1m, 3.48 g (3.31 mmol) of the compound that is produced according to Example 23c is reacted, and after working-up and purification, 2.36 g (2.5 mmol, 76%) of the title compound is isolated as a colorless oil.

$^1$H-NMR (CDCl$_3$): δ=0.00–0.18 (27H), 0.83–0.99 (30H), 1.01–1.80 (7H), 1.12 (3H), 1.27 (3H), 1.60+1.68 (3H), 1.86–2.07 (3H), 2.83–2.52 (3H), 2.64 (1H), 2.70 (3H), 3.26 (1H), 3.66 (2H), 3.80 (1H), 4.10 (1H), 4.20 (1H), 5.16 (1H), 6.06 (1H), 7.32 (1H) ppm.

Example 23e (3S,6R,7S,8S,12E/Z,15S,16Z)-16-Fluoro-5-oxo-3,7,15-tris-[[(1,1-dimethylethyl)dimethylsilyl]oxy]-6-(3-(trimethylsilyl)-prop-2-in-1-yl)-4,4,8,12-tetramethyl-17-(2-methylthiazol-4-yl)-heptadeca-12,16-dienal Analogously to Example 1n, 2.36 g (2.51 mmol) of the compound that is produced according to Example 23d is reacted, and after working-up and purification, 2.25 g (2.40 mmol, 96%) of the title compound is isolated as a colorless oil.

Example 23f (3S,6R,7S,8S,12Z,15S,16Z)-16-Fluoro-5-oxo-3,7,15-tris-[[(1,1-dimethylethyl)dimethylsilyl]oxy]-6-(3-(trimethylsilyl)-prop-2-in-1-yl)-4,4,8,12-tetramethyl-17-(2-methylthiazol-4-yl)-heptadeca-12,16-dienoic acid (A) and (3S,6R,7S,8S,12E,15S,16Z)-16-fluoro-5-oxo-3,7,15-tris-[[(1,1-dimethylethyl)dimethylsilyl]oxy]-6-(3-(trimethylsilyl)-prop-2-in-1-yl)-4,4,8,12-tetramethyl-17-(2-methylthiazol-4-yl)-heptadeca-1,2,16-dienoic acid (B)

Analogously to Example 22q, 2.25 g (2.40 mmol) of the compound that is produced according to Example 23e is reacted, and after working-up and purification, 960 mg (1.01 mmol, 42%) of title compound A as well as 937 mg (0.98 mmol, 41%) of title compound are isolated in each case as a colorless oil.

$^1$H-NMR (CDCl$_3$) of A: δ=–0.02–0.17 (27H), 0.89 (27H), 0.94 (3H), 1.08–1.67 (6H), 1.18 (3H), 1.22 (3H), 1.70 (3H), 1.89 (1H), 2.12 (1H), 2.28–2.53 (5H), 2.61 (1H), 2.69 (3H), 3.31 (1H), 3.71 (1H), 4.20 (1H), 4.38 (1H), 5.18 (1H), 6.40 (1H), 7.36 (1H) ppm.

$^1$H-NMR (CDCl$_3$) of B: δ=–0.01–0.18 (27H), 0.84–0.97 (30H), 1.00–1.55 (6H), 1.20 (3H), 1.23 (3H), 1.59 (3H), 1.82–2.05 (2H), 2.25–2.60 (4H), 2.65 (1H), 2.70 (3H), 3.33 (1H), 3.76 (1H), 4.16 (1H), 4.38 (1H), 5.13 (1H), 6.12 (1H), 7.38 (1H) ppm.

Example 23g (3S,6R,7S,8S,12Z,15S,16Z)-16-Fluoro-5-oxo-3,7-bis-[[(1,1-dimethylethyl)dimethylsilyl]oxy]-15-hydroxy-6-(prop-2-in-1-yl)-4,4,8,12-tetramethyl-17-(2-methylthiazol-4-yl)-heptadeca-12,16-dienoic acid Analogously to Example 1e, 960 mg (1.01 mmol) of compound A that is produced according to Example 23f is reacted, and after working-up, 898 mg (max. 1.01 mmol) of the title compound is isolated, which is further reacted without purification.

Example 23h (4S,7R,8S,9S,13Z,16S(Z))-4,8-Bis-[[dimethyl(1,1-dimethylethyl)silyl]oxy]-16-(1-fluoro-2-(2-methylthiazol-4-yl)-ethenyl)-7-(prop-2-in-1-yl)-1-oxa-5,5,9,13-tetramethyl-cyclohexadec-13-ene-2,6-dione Analogously to Example 1q, a total of 896 mg (max. 1.01 mmol) of the compound that is produced according to Example 23b is reacted in several portions, and after working-up and purification, 480 mg (0.64 mmol, 64%) of the title compound is isolated as a colorless oil.

$^1$H-NMR (CDCl$_3$): δ=–0.10 (3H), 0.12 (3H0, 0.15 (3H), 0.19 (3H), 0.80–1.83 96H), 0.85 (9H), 0.94 (9H), 1.01 (3H), 1.18 (3H), 1.23 (3H), 1.68 (3H), 2.08 (1H), 2.22–2.89 (7H), 2.69 (3H), 3.09 (1H), 4.00–4.12 (2H), 5.07–5.21 (2H), 6.13 (1H), 7.36 (1H) ppm.

Example 23i (4S,7R,8S,9S,13Z,16S(Z))-4,8-Dihydroxy-16-(1-fluoro-2-(2-methylthiazol-4-yl)ethenyl)-7-(prop-2-in-1-yl)-1-oxa-5,5,9,13-tetramethyl-cyclohexadec-13-ene-2,6-dione Analogously to Example 1, 60 mg (80 μmol) of the compound that is produced according to Example 23h is reacted, and after working-up and purification, 28 mg (54 μmol, 67%) of the title compound is isolated as a colorless oil.

$^1$H-NMR (CDCl$_3$): δ=1.05 (3H), 1.11 (3H), 1.18–1.42 (3H), 1.38 (3H), 1.56–1.97 (3H), 1.90 (3H), 2.05 (1H), 2.28 (1H), 2.33–2.66 (6H), 2.69 (3H), 2.79 (1H), 3.30 (1H), 3.38 (1H), 3.79 (1H), 4.21 (1H), 5.12 (1H), 5.46 (1H), 6.19 (1H), 7.36 (1H) ppm.

Example 24

(4S,7R,8S,9S,13E,16S(Z))-4,8-Dihydroxy-16-(1-fluoro-2-(2-methylthiazol-4-yl)ethenyl)-7-(prop-2-in-1-yl)-1-oxa-5,5,9,13-tetramethyl-cyclohexadec-13-ene-12,6-dione

Example 24a (3S,6R,7S,8S,12E,15S,16Z)-16-Fluoro-5-oxo-3,7-bis-[[(1,1-dimethylethyl)dimethylsilyl]oxy]-15-hydroxy-6-(prop-2-in-1-yl)-4,4,8,12-tetramethyl-17-(2-methylthiazol-4-yl)-heptadeca-12,16-dienoic acid Analogously to Example 1e, 937 mg (0.98 mmol) of compound B that is produced according to Example 23f is reacted, and after working-up, 914 mg (max. 0.98 mmol) of the title compound is isolated, which is further reacted without purification.

Example 24b (4S,7R,8S,9S,13E,16S(Z))-4,8-Bis-[[dimethyl(1,1-dimethylethyl)silyl]oxy]-16-(1-fluoro-2-(2-methylthiazol-4-yl)-ethenyl)-7-(prop-2-in-1-yl)-1-oxa-5,5,9,13-tetramethyl-cyclohexadec-13-ene-2,6-dione Analogously to Example 1q, 914 mg (max. 0.98 mmol) of the compound that is produced according to Example 24a is reacted, and after working-up and purification, 451 mg (603 µmol, 62%) of the title compound is isolated as a colorless oil.

$^1$H-NMR (CDCl$_3$): δ=0.02–0.12 (12H), 0.79–1.73 (5H), 0.89 (18H), 0.96 (3H), 1.12 (3H), 1.22 (3H), 1.58 (3H), 1.91 (1H), 2.01 (1H), 2.11 (1H), 2.39–2.80 (6H), 2.69 (3H), 3.15 (1H), 3.91 (1H), 4.33 (1H), 5.17 (1H), 5.42 (1H), 6.12 (1H), 7.36 (1H) ppm.

Example 24c (4S,7R,8S,9S,13E,16S(Z))-4,8-Dihydroxy-16-(1-fluoro-2-(2-methylthiazol-4-yl)ethenyl)-7-(prop-2-in-1-yl)-1-oxa-5,5,9,13-tetramethyl-cyclohexadec-13-ene-2,6-dione Analogously to Example 1, 451 mg (603 µmol) of the compound that is produced according to Example 24b is reacted, and after working-up and purification, 170 mg (327 µmol, 54%) of the title compound is isolated as a colorless oil.

$^1$H-NMR (CDCl$_3$): δ=0.86 (1H), 1.00 (3H), 1.03 (3H), 1.26–2.23 (7H), 1.33 (3H), 1.60 (3H), 2.41–2.62 (6H), 2.69 (3H), 3.59 (1H), 3.79 (1H), 4.02–4.19 (2H), 4.39 (1H), 5.11 (1H), 5.54 (1H), 6.17 (1H), 7.37 (1H) ppm.

Example 25

(1S,3S(Z),7S,10R,11S,12S,16R)-7,11-Dihydroxy-3-(1-fluoro-2-(2-methyl-4-thiazolyl)ethenyl)-10-(prop-2-in-1-yl)-8,8,12,16-tetramethyl-4,17-dioxabicyclo[14.1.0]heptadecane-5,9-dione (A) and (1R,3S(Z),7S,10R,11S,12S,16S)-7,11-dihydroxy-3-(1-fluoro-2-(2-methyl-4-thiazolyl)ethenyl)-10-(prop-2-in-1-yl)-8,8,12,16-tetramethyl-4,17-dioxabicyclo[14.1.0]heptadecane-5,9-dione (B)

The solution of 50 mg (96 µmol) of the compound, produced according to Example 23, in 4.5 ml of acetonitrile is mixed at 0° C. with 554 µl of a 0.1 M aqueous solution of ethylenediamine tetraacetate, 638 µl of trifluoroacetone, 260 mg of sodium bicarbonate, 150 mg of oxone, and it is stirred for 1.5 hours at 23° C. It is mixed with sodium thiosulfate solution, extracted several times with ethyl acetate, the combined organic extracts are washed with saturated sodium chloride solution, dried on sodium sulfate, and the residue is purified by chromatography on analytic thin-layer plates. As a mobile solvent, a mixture that consists of dichloromethane and isopropanol is used; as an eluant, a mixture that consists of dichloromethane and methanol is used. 29 mg (54 µmol, 56%) of title compound A as well as 9 mg (17 µmol, 18%) of title compound B are isolated in each case as a colorless oil.

$^1$H-NMR (CDCl$_3$) of A: δ=1.01 (3H), 1.08 (3H), 1.22–1.81 (7H), 1.28 (3H), 1.39 (3H), 2.01 (1H), 2.04 (1H), 2.19 (1H), 2.40–2.76 (5H), 2.69 (3H), 2.91 (1H), 3.60 (1H), 3.80 (1H), 4.19 (1H), 4.31 (1H), 5.70 (1H), 6.23 (1H), 7.38 (1H) ppm.

$^1$H-NMR (CDCl$_3$) of B: δ=0.97 (3H), 1.08 (3H), 1.19–1.96 (8H), 1.25 (3H), 1.42 (3H), 1.99 (1H), 2.28 (1H), 2.42–2.62 (4H), 2.70 (3H), 2.98 (1H), 3.04 (1H), 3.49 (1H), 3.62 (1H), 4.04 (1H), 4.23 (1H), 5.80 (1H), 6.21 (1H), 7.38 (1H) ppm.

Example 26

(1S,3S(Z),7S,10R,11S,12S,16S)-7,11-Dihydroxy-3-(1-fluoro-2-(2-methyl-4-thiazolyl)ethenyl)-10-(prop-2-in-1-yl)-8,8,12,16-tetramethyl-4,17-dioxabicyclo[14.1.0]heptadecane-5,9-dione (A) and (1R,3S(Z),7S,10R,1S,12S,16R)-7,11-dihydroxy-3-(1-fluoro-2-(2-methyl-4-thiazolyl)ethenyl)-10-(prop-2-in-1-yl)-8,8,12,16-tetramethyl-4,17-dioxabicyclo[14.1.0]heptadecane-5,9-dione (B) and (1SR,3S(Z),7S,10R,11S,12S,16SR)-7,11-dihydroxy-3-(1-fluoro-2-(2-methyl-4-(N-oxido)-thiazolyl)ethenyl)-10-(prop-2-in-1-yl)-8,8,12,16-tetramethyl-4,17-dioxabicyclo[14.1.0]heptadecane-5,9-dione (C)

Analogously to Example 25, 80 mg (154 µmol) of the compound that is produced according to Example 24 is reacted, and after working-up and purification, 21 mg (39 µmol, 25%) of title compound A, 31 mg (58 µmol, 38%) of title compound B as well as 3 mg (6 µmol, 4%) of title compounds C are isolated in each case as a colorless oil.

$^1$H-NMR (CDCl$_3$) of A or B: δ=0.96 (3H), 1.08 (3H), 1.18–1.85 (7H), 1.22 (3H), 1.38 (3H), 1.99 (1H), 2.09 (1H), 2.20 (1H), 2.40 (1H), 2.51–2.72 (3H), 2.68 (3H), 2.99 (1H), 3.13 (1H), 3.53 (1H), 3.75 (1H), 3.82 (1H), 4.30 (1H), 5.66 (1H), 6.21 (1H), 7.37 (1H) ppm.

$^1$H-NMR (CDCl$_3$) of B or A: δ=0.93 (3H), 1.04 (3H), 1.11–1.81 (7H), 1.28 (3H), 1.41 (3H), 1.99 (1H), 2.06–2.23 (2H), 2.43 (1H), 2.51–2.72 (4H), 2.69 (3H), 2.87 (1H), 3.55 (1H), 3.85 (1H), 4.19 (1H), 4.31 (1H), 5.66 (1H), 6.24 (1H), 7.39 (1H) ppm.

$^1$H-NMR of C (CDCl$_3$): δ=0.95+0.99 (3H), 1.08+1.10 (3H), 1.13–2.77 (14H), 1.22+1.26 (3H), 1.45+1.51 (3H), 2.59 (3H), 2.95 (1H), 3.52–3.86 (2H), 4.13+5.41 (1H), 4.43–4.70 (2H), 5.63+5.72 (1H), 6.56+6.59 (1H), 7.41+7.46 (1H) ppm.

Example 27

(4S,7R,8S,9S,13Z,16S(Z))-4,8-Dihydroxy-16-(1-fluoro-2-(2-methyloxazol-4-yl)ethenyl)-7-(prop-2-in-1-yl)-1-oxa-5,9,13-tetramethyl-cyclohexadec-13-ene-2,6-dione

Example 27a 4-(2-Methyloxazolyl)-carbaldehyde

The solution of 36.6 g (236 mmol) of 4-(2-methyloxazolyl)-carboxylic acid ethyl ester in 795 ml of anhydrous dichloromethane is cooled under an atmosphere of dry argon to −78° C., mixed with 378 ml of a 1.0 molar solution of diisobutylaluminum hydride in n-hexane, and it is stirred for 1 more hour. It is mixed with 96 ml of isopropanol, 160 ml of water, allowed to heat to 23° C. and stirred until a fine-grained precipitate has formed. After filtration and removal of the solvent, 24.7 g (222 mmol, 94%) of the title compound is isolated as a pale yellow oil.

$^1$H-NMR (CDCl$_3$): δ=2.53 (3H), 8.17 (1H), 9.90 (1H) ppm.

Example 27b (2Z)-3-(2-Methyloxazol-4-yl)-2-fluoro-2-propenoic acid ethyl ester (A) and (2E)-3-(2-methyloxazol-4-yl)-2-fluoro-2-propenoic acid ethyl ester (B)

The solution of 106 g of 2-fluoro-2-phosphonoacetic acid triethyl ester in 224 ml of ethylene glycol dimethyl ether is added in drops under an atmosphere of dry argon at 0° C. to 19.1 g of a 55% sodium hydride dispersion in 224 ml of anhydrous ethylene glycol dimethyl ether, and it is stirred for one more hour. Then, it is mixed with the solution of 26.4 g (238 mmol) of the compound, produced according to Example 27a, in 224 ml of ethylene glycol dimethyl ether, and it is allowed to heat within 1 hour to 23° C. It is poured onto a saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 24.8 g (125 mmol, 52%) of title compound A is isolated as a crystalline solid, and 12.5 g (63 mmol, 26%) of title compound B is isolated as a colorless oil.

$^1$H-NMR (CDCl$_3$) of A: δ=1.37 (3H), 2.49 (3H), 4.32 (2H), 6.91 (1H), 7.94 (1H) ppm.
$^1$H-NMR (CDCl$_3$) of B: δ=1.39 (3H), 2.47 (3H), 4.36 (2H), 6.75 (1H), 8.53 (1H) ppm.

Example 27c (2Z)-3-(2-Methyloxazol-4-yl)-2-fluoro-2-propenoic acid ethyl ester The solution of 24.4 g (123 mmol) of compound B, produced according to Example 27b, in 130 ml of anhydrous toluene is mixed with 5.3 ml of thiophenol, and it is stirred for 2 days under an atmosphere of dry argon at 23° C. It is poured into a 5% sodium hydroxide solution, extracted several times with ethyl acetate, the combined organic extracts are washed with water, saturated sodium chloride solution and dried on magnesium sulfate. The residue that is obtained after filtration and removal of the solvent is purified by chromatography on fine silica gel with a gradient system that consists of n-hexane and ethyl acetate. 19.5 g (98 mmol, 80%) of the title compound is isolated as a crystalline solid.

Example 27d (2Z)-3-(2-Methyloxazol-4-yl)-2-fluoro-2-propenal

The solution of 26.2 g (131 mmol) of compound A, produced according to Example 27b or 3c, in 380 ml of anhydrous toluene is cooled under an atmosphere of dry argon to −78° C., mixed with 180 ml of a 1.2 M solution of diisobutylaluminum hydride in toluene, and it is stirred for 8 hours. It is mixed with water, extracted several times with ethyl acetate, the combined organic extracts are washed with saturated sodium chloride solution and dried on sodium sulfate. After filtration and removal of the solvent, 20.1 g (128 mmol, 98%) of the title compound is isolated as a colorless oil, which is further reacted without purification.

$^1$H-NMR (CDCl$_3$): δ=2.51 (3H), 6.69 (1H), 8.07 (1H), 9.32 (1H) ppm.

Example 27e (3S,4Z)-5-(2-Methyloxazol-4-yl)-1-[(4S,5R)-4-methyl-5-phenyl-oxazolidin-2-on-3-yl]-3-hydroxy-4-fluoro-4-penten-1-one (A) and (3R,4Z)-5-(2-methyloxazol-4-yl)-1-[(4S,5R)-4-methyl-5-phenyl-oxazolidin-2-on-3-yl]-3-hydroxy-4-fluoro-4-penten-1-one (B)

136 ml of a 2.4 molar solution of n-butyllithium in n-hexane is added in drops at −30° C. under an atmosphere of dry argon to the solution of 45.8 ml of diisopropylamine in 2 l of anhydrous tetrahydrofuran, and it is stirred for 20 minutes, cooled to −70° C. and mixed within 4 hours with the solution of 64.2 g of (4S,5R)-3-acetyl-4-methyl-5-phenyloxazolidin-2-one in 1 l of tetrahydrofuran. After 1 hour, the solution of 15.1 g (97.6 mmol) of the compound, produced according to Example 27d, in 650 ml of tetrahydrofuran is added in drops within 2 hours, and it is stirred for 16 hours at −70° C. It is poured onto a saturated ammonium chloride solution, extracted several times with ethyl acetate, the combined organic extracts are washed with saturated sodium chloride solution and dried on sodium sulfate. The residue that is obtained after filtration and removal of the solvent is separated by repeated chromatography on fine silica gel with a gradient system that consists of n-hexane, ethyl acetate and ethanol. 19.9 g (53 mmol, 54%) of title compound A is isolated as a crystalline solid, and 8.2 g (22 mmol, 22%) of title compound B is isolated as a colorless foam.

$^1$H-NMR (CDCl$_3$) of A: δ=0.92 (3H), 2.47 (3H), 3.33 (1H), 3.50 (1H), 3.70 (1H), 4.73–4.88 (2H), 5.71 (1H), 5.97 (1H), 7.26–7.48 (5H), 7.75 (1H) ppm.
$^1$H-NMR (CDCl$_3$) of B: =0.93 (3H), 2.48 (3H), 3.40 (2H), 4.73–4.90 (2H), 5.70 (1H), 5.98 (1H), 7.24–7.49 (5H), 7.76 (1H) ppm.

Example 27f (3S,4Z)-5-(2-Methyloxazol-4-yl)-1-[(4S,5R)-4-methyl-5-phenyl-oxazolidin-2-on-3-yl]-3-[[dimethyl(1,1-dimethylethyl)silyl]oxy]-4-fluoro-4-penten-1-one Analogously to Example 1l, 16.2 g (43.5 mmol) of compound A that is produced according to Example 27e is reacted, and after working-up and purification, 15.9 g (32.5 mmol, 75%) of the title compound is isolated as a colorless oil.
$^1$H-NMR (CDCl$_3$): δ=0.11 (6H), 0.88 (9H), 0.90 (3H), 2.46 (3H), 3.24 (1H), 3.52 (1H), 4.77 (1H), 4.89 (1H), 5.66 (1H), 5.83 (1H), 7.23–7.48 (5H), 7.74 (1H) ppm.

Example 27g (3S,4Z)-5-(2-Methyloxazol-4-yl)-3-[[dimethyl(1,1-dimethylethyl)silyl]oxy]-4-fluoro-4-pentenoic acid ethyl ester Analogously to Example 22e, 15.6 g (32.6 mmol) of the compound that is produced according to Example 27f is reacted, and after working-up and purification, 11.4 g (32 mmol, 98%) of the title compound is isolated as a colorless oil.
$^1$H-NMR (CDCl$_3$): δ=0.08 (6H), 0.88 (9H), 1.26 (3H), 2.43 (3H), 2.67 (2H), 4.13 (2H), 4.71 (1H), 5.80 (1H), 7.72 (1H) ppm.

Example 27h (3S,4Z)-5-(2-Methyloxazol-4-yl)-3-[[dimethyl(1,1-dimethylethyl)silyl]oxy]-4-fluoro-4-penten-1-ol Analogously to Example 22f, 11.4 g (31.9 mmol) of the compound that is produced according to Example 27g is reacted, and after working-up and purification, 9.16 g (29 mmol, 91%) of the title compound is isolated as a colorless oil.
$^1$H-NMR (CDCl$_3$): δ=0.07 (3H), 0.10 (3H), 0.90 (9H), 1.94 (2H), 2.08 (1H), 2.43 (3H), 3.73 (1H), 3.80 (1H), 4.49 (1H), 5.80 (1H), 7.71 (1H) ppm.

Example 27i (3S,4Z)-5-(2-Methyloxazol-4-yl)-3-[[dimethyl(1,1-dimethylethyl)silyl]oxy]-1-iodo-4-fluoro-4-pentene Analogously to Example 22g, 7.16 g (22.7 mmol) of the compound that is produced according to Example 27h is reacted, and after working-up and purification, 8.06 g (18.9 mmol, 83%) of the title compound is isolated as a colorless oil.
$^1$H-NMR (CDCl$_3$): δ=0.09 (3H), 0.15 (3H), 0.91 (9H), 2.20 (2H), 2.46 (3H), 3.23 (2H), 4.33 (1H), 5.80 (1H), 7.73 (1H) ppm.

Example 27j (3S,4Z)-5-(2-Methyloxazol-4-yl)-3-[[dimethyl(1,1-dimethylethyl)silyl]oxy]-4-fluoro-4-pentene-1-triphenylphosphonium iodide Analogously to Example 22h, 8.06 g (18.9 mmol) of the compound that is produced according to Example 27i is reacted, and after working-up and purification, 10.7 g (15.6 mmol, 82%) of the title compound is isolated as a colorless oil.
$^1$H-NMR (CDCl$_3$): δ=0.10 (3H), 0.18 (3H), 0.87 (9H), 1.97 (1H), 2.10 (1H), 2.42 (3H), 3.48 (1H), 3.97 (1H), 4.86 (1H), 5.93 (1H), 7.63–7.88 (16H) ppm.

Example 27k (2S,6E/Z,9S,10Z)-9-[[(Dimethyl(1,1-dimethylethyl)silyl]oxy]-10-fluoro-11-(2-methyloxazol-4-yl)-1-(tetrahydropyran-2-yloxy)-2,6-dimethyl-undeca-6,10-diene Analogously to Example 22i, 3.20 g (14.0 mmol) of the compound that is produced according to Example 27j is reacted, and after working-up and purification, 3.53 g (6.9 mmol, 49%) of the title compound is isolated as a colorless oil.
$^1$H-NMR (CDCl$_3$): δ=0.08 (6H), 0.84–0.97 (12H), 1.09 (1H), 1.22–2.04 (12H), 1.59+1.68 (3H), 2.30–2.49 (2H), 2.44 (3H), 3.06–3.27 (1H), 3.42–3.62 (2H), 3.86 (1H), 4.19 (1H), 4.55 (1H), 5.12 (1H), 5.73 (1H), 7.71 (1H) ppm.

Example 27l (2S,6E/Z,9S,10Z)-9-[[Dimethyl(1,1-dimethylethyl)silyl]oxy]-10-fluoro-1-(2-methyloxazol-4-yl)-1-hydroxy-2,6-dimethyl-undeca-6,10-diene Analogously to Example 1k, 3.48 g (6.83 mmol) of the compound that is produced according to Example 27k is reacted, and after working-up and purification, 2.28 g (5.36 mmol, 78%) of the title compound is isolated as a colorless oil.
$^1$H-NMR (CDCl$_3$): δ=0.08 (6H), 0.83–0.94 (12H), 1.03 (1H), 1.21–1.70 (5H), 1.58+1.68 (3H), 1.91–2.05 (2H), 2.27–2.50 (2H), 2.44 (3H), 3.37–3.52 (2H), 4.19 (1H), 5.12 (1H), 5.72 (1H), 7.72 (1H) ppm.

Example 27m (2S,6E/Z,9S,10Z)-9-[[Dimethyl(1,1-dimethylethyl)silyl]oxy]-10-fluoro-11-(2-methyloxazol-4-yl)-2,6-dimethyl-undeca-6,10-dienal Analogously to Example 1n, 2.28 g (5.36 mmol) of the compound that is produced according to Example 27l is reacted, and after working-up and purification, 2.27 g (5.36 mmol, 100%) of the title compound is isolated as a colorless oil.
$^1$H-NMR (CDCl$_3$): δ 0.06 (6H), 0.90 (9H), 1.03+1.08 (3H), 1.21–1.46 (4H), 1.57+1.66 (3H), 2.00 (2H), 2.21–2.42 (3H), 2.45 (3H), 4.19 (1H), 5.14 (1H), 5.73 (1H), 7.71 (1H), 9.59 (1H) ppm.

Example 27n (4S(4R,5S,6S,10E/Z,13S,14Z))-4-(13-[[(1,1-Dimethylethyl)dimethylsilyl]oxy]-4-(prop-2-in-1-yl)-14-fluoro-15-(2-methyloxazol-4-yl)-3-oxo-5-hydroxy-2,6,10-trimethyl-pentadeca-10,14-dien-2-yl)-2,2-dimethyl-[1,3]dioxane (A) and (4S(4S,5R,6S,10E/Z,13S,14Z))-4-(13-[[(1,1-dimethylethyl)dimethylsilyl]oxy]-4-(prop-2-in-1-yl)-14-fluoro-15-(2-methyloxazol-4-yl)-3-oxo-5-hydroxy-2,6,10-trimethyl-pentadeca-10,14-dien-2-yl)-2,2-dimethyl-[1,3]dioxane (B)

Analogously to Example 1c, 1.87 g (4.41 mmol) of the compound, produced according to Example 27m, with (4S)-

4-(2-methyl-3-oxo-7-trimethylsilyl-hept-6-in-2-yl)-
2,2-dimethyl-[1,3]dioxane, which was produced
according to the process described in DE
19751200.3, is reacted, and after working-up and
purification, in addition to starting material, 1.37 g
(1.87 mmol, 42%) of title compound A as well as
190 mg (0.26 mmol, 6%) of title compound B are
isolated in each case as a colorless oil.

$^1$H-NMR (CDCl$_3$) of A: δ=0.02–0.16 (15H), 0.81–0.93 (12H), 0.97–1.78 (13H), 1.06 (3H), 1.39 (3H), 1.58+1.67 (3H), 1.91–2.08 (2H), 2.30–2.48 (3H), 2.44 (3H), 2.55 (1H), 3.03 (1H), 3.45 (1H), 3.52 (1H), 3.88 (1H), 3.99 (1H), 4.08–4.23 (2H), 5.12 (1H), 5.72 (1H), 7.72 (1H) ppm.

$^1$H-NMR (CDCl$_3$) of B: δ=0.01–0.12 (15H), 0.82–1.73 (18H), 0.89 (9H), 1.17 (3H), 1.40 (3H), 1.58+1.67 (3H), 1.88–2.05 (2H), 2.28–2.57 (3H), 2.42 (3H), 3.41 (1H), 3.59 (1H), 3.79–4.05 (3H), 4.18 (1H), 5.11 (1H), 5.72 (1H), 7.70 (1H) ppm.

Example 27o (3S,6R,7S,8S,12E/Z,15S,16Z)-15-[[(1,1-Dimethyl-
ethyl)dimethylsilyl]oxy]-6-(3-(trimethylsilyl)-prop-
2-in-1-yl)-16-fluoro-1,3,7-trihydroxy-4,4,8,12-tet-
ramethyl-17-(2-methyloxazol-4-yl)-heptadeca-12,
16-dien-5-one Analogously to Example 1k, 2.16 g (2.94 mmol) of compound A that is produced according to Example 27n is reacted, and after working-up and purification, 1.47 g (2.12 mmol, 72%) of the title compound is isolated as a colorless oil.

$^1$H-NMR (CDCl$_3$): δ=0.03 (6H), 0.15 (9H), 0.85–0.95 (12H), 0.98–1.80 (7H), 1.15 (3H), 1.27 (3H), 1.57+1.66 (3H), 1.90–1.08 (2H), 2.30–2.45 (3H), 2.49+2.51 (3H), 2.58–2.72 (2H), 2.90+3.03 (1H), 3.37–3.72 (3H), 3.88 (2H), 4.07–4.22 (2H), 5.11 (1H), 5.63+5.70 (1H), 7.71 (1H) ppm.

Example 27p (3S,6R,7S,8S,12E/Z,15S,16Z)-16-
Fluoro-1,3,7,15-tetrakis-[[(1,1-dimethylethyl)dim-
ethylsilyl]oxy]-6-(3-(trimethylsilyl)-prop-2-in-1-yl)-
4,4,8,12-tetramethyl-17-(2-methyloxazol-4-yl)-
heptadeca-12,16-dien-5-one Analogously to Example 1l, 1.47 g (2.12 mmol) of the compound that is produced according to Example 27o is reacted, and after working-up and purification, 2.13 g (2.05 mmol, 97%) of the title compound is isolated as a colorless oil.

$^1$H-NMR (CDCl$_3$): =0.00–0.15 (33H), 0.83–0.98 (39H), 1.00–1.72 (7H), 1.07 (3H), 1.26 (3H), 1.59+1.67 (3H), 1.94 (2H), 2.27–2.43 (2H), 2.43 (3H), 2.51 (2H), 3.28 (1H), 3.52–3.71 (2H), 3.78 (1H), 3.88 (1H), 4.18 (1H), 5.12 (1H), 5.73 (1H), 7.71 (1H) ppm.

Example 27q (3S,6R,7S,8S,12E/Z,15S,16Z)-16-Fluoro-1-hydroxy-
3,7,15-tris-[[(1,1-dimethylethyl)dimethylsilyl]oxy]-
6-(3-(trimethylsilyl)-prop-2-in-1-yl)-4,4,8,12-tetram-
ethyl-17-(2-methyloxazol-4-yl)-heptadeca-12,16-
dien-5-one Analogously to Example 1m, 2.13 g (2.05 mmol) of the compound that is produced according to Example 27p is reacted, and after working-up and purification, 1.47 g (1.60 mmol, 78%) of the title compound is isolated as a colorless oil.

$^1$H-NMR (CDCl$_3$): δ=0.00–0.15 (27H), 0.83–0.98 (30H), 1.02–1.77 (7H), 1.10 (3H), 1.27 (3H), 1.59+1.68 (3H), 1.89–2.07 (3H), 2.30–2.52 (3H), 2.45 (3H), 1.68 (1H), 3.27 (1H), 3.60–3.71 (2H), 3.79 (1H), 4.05–4.23 (2H), 5.13 (1H), 5.73 (1H), 7.70 (1H) ppm.

Example 27r (3S,6R,7S,8S,12E/Z,15S,16Z)-16-Fluoro-5-oxo-3,7,
15-tris-[[(1,1-dimethylethyl)dimethylsilyl]oxy]-6-(3-
(trimethylsilyl)-prop-2-in-1-yl)-4,4,8,12-tetramethyl-
17-(2-methyloxazol-4-yl)-heptadeca-12,16-dienal Analogously to Example 1n, 1.47 g (1.60 mmol) of the compound that is produced according to Example 27q is reacted, and after working-up, 1.62 g (max. 1.60 mmol) of the title compound is isolated as a colorless oil.

$^1$H-NMR (CDCl$_3$) of a purified sample: δ=−0.01–0.11 (27H), 0.83–0.98 (30H), 1.00–1.56 (5H), 1.11 (3H), 1.28 (3H), 1.59+1.68 (3H), 1.88–2.02 (2H), 2.29–2.50 (4H), 2.43 (3H), 2.58–2.71 (2H), 3.26 (1H), 3.78 (1H), 4.18 (1H), 4.50 (1H), 5.12 (1H), 5.73 (1H), 7.71 (1H), 9.77 (1H) ppm.

Example 27s (3S,6R,7S,8S,12Z,15S,16Z)-16-Fluoro-5-oxo-3,7,
15-tris-[[(1,1-dimethylethyl)dimethylsilyl]oxy]-6-(3-
(trimethylsilyl)-prop-2-in- 1-yl)-4,4,8,12-tetram-
ethyl-17-(2-methyloxazol-4-yl)-heptadeca-12,16-
dienoic acid (A) and (3S,6R,7S,8S,12E,15S,16Z)-
16-fluoro-5-oxo-3,7,15-tris-[[(1,1-dimethylethyl)
dimethylsilyl]oxy]-6-(3-(trimethylsilyl)-prop-2-in-1-
yl)-4,4,8,12-tetramethyl-17-(2-methyloxazol-4-yl)-
heptadeca-12,16-dienoic acid (B)

Analogously to Example 22q, 1.60 g (max. 1.60 mmol) of the compound that is produced according to Example 27r is reacted, and after working-up and purification, 601 mg (642 μmol, 40%) of title compound A as well as 500 mg (534 μmol, 33%) of title compound B are isolated in each case as a colorless oil.

$^1$H-NMR (CDCl$_3$) of A: δ=−0.04–0.19 (27H), 0.89 (27H), 0.96 (3H), 1.05–2.53 (13H), 1.19 (3H), 1.26 (3H), 1.69 (3H), 2.46 (3H), 2.63 (1H), 3.32 (1H), 3.71 (1H), 4.61 (1H), 4.39 (1H), 5.18 (1H), 6.08 (1H), 7.73 (1H) ppm.

$^1$H-NMR (CDCl$_3$) of B: δ–0.02–0.18 (27H), 0.90 (30H), 0.99–2.67 (14H), 1.21 (6H), 1.58 (3H), 2.46 (3H), 3.32 (1H), 3.74 (1H), 4.13 (1H), 4.36 (1H), 5.10 (1H), 5.79 (1H), 7.72 (1H) ppm.

Example 27t (3S,6R,7S,8S,12Z,15S,16Z)-16-Fluoro-5-oxo-3,7-
bis-[[(1,1-dimethylethyl)dimethylsilyl]oxy]-15-hy-
droxy-6-(prop-2-in-1-yl)- 4,4,8,12-tetramethyl-17-
(2-methyloxazol-4-yl)-heptadeca-12,16-dienoic acid Analogously to Example 1e, 601 mg (642 μmol) of compound A that is produced according to Example. 27s is reacted, and after working-up, 657 mg (max. 642 μmol) of the title compound is isolated as a crude product, which is further reacted without purification.

Example 27u (4S,7R,8S,9S,13Z,16S(Z))-4,8-Bis-[[dimethyl(1,1-dimethylethyl)silyl]oxy]-16-(1-fluoro-2-(2-methyloxazol-4-yl)ethenyl)-7-(prop-2-in-1-yl)-1-oxa-5,5,9,13-tetramethyl-cyclohexadec-13-ene-2,6-dione Analogously to Example 1q, 657 mg (max. 642 μmol) of the compound that is produced according to Example 27u is reacted, and after working-up and purification, 91 mg (124 μmol, 19%) of the title compound is isolated as a colorless oil.

Example 27v (4S,7R,8S,9S,13Z,16S(Z))-4,8-Dihydroxy-16-(1-fluoro-2-(2-methyloxazol-4-yl)ethenyl)-7-(prop-2-in-1-yl)-1-oxa-5,5,9,13-tetramethyl-cyclohexadec-13-ene-2,6-dione Analogously to Example 1, 91 mg (124 μmol) of the compound that is produced according to Example 27u is reacted, and after working-up and purification, 45 mg (89 μmol, 73%) of the title compound is isolated as a colorless oil.

$^1$H-NMR (CDCl$_3$): =1.05 (3H), 1.10 (3H), 1.20–1.42 (4H), 1.37 (3H), 1.58–1.94 (2H), 1.69 (3H), 2.04 (1H), 2.20–2.84 (8H), 2.45 (3H), 3.20 (1H), 3.38 (1H), 3.78 (1H), 4.20 (1H), 5.11 (1H), 5.43 (1H), 5.90 (1H), 7.73 (1H) ppm.

Example 28

(4S,7R,8S,9S,13E,16S(Z))-4,8-Dihydroxy-16-(1-fluoro-2-(2-methyloxazol-4-yl)ethenyl)-7-(prop-2-in-1-yl)-1-oxa-5,5,9,13-tetramethyl-cyclohexadec-13-ene-2,6-dione

Example 28a (3S,6R,7S,8S,12E,15S,16Z)-16-Fluoro-5-oxo-3,7-bis-[[(1,1-dimethylethyl)dimethylsilyl]oxy]-15-hydroxy-6-(prop-2-in-1-yl)-4,4,8,12-tetramethyl-17-(2-methyloxazol-4-yl)-heptadeca-12,16-dienoic acid Analogously to Example 1e, 500 mg (534 μmol) of compound B that is produced according to Example 27f is reacted, and after working-up, 517 mg (max. 534 μmol) of the title compound is isolated as crude product, which is further reacted without purification.

Example 28b (4S,7R,8S,9S,13E,16S(Z))-4,8-Bis-[[dimethyl(1,1-dimethylethyl)silyl]oxy]-16-(1-fluoro-2-(2-methyloxazol-4-yl)ethenyl)-7-(prop-2-in-1-yl)-1-oxa-5,5,9,13-tetramethyl-cyclohexadec-13-ene-2,6-dione Analogously to Example 1q, 517 mg (534 μmol) of the compound that is produced according to Example 28a is reacted, and after working-up and purification, 128 mg (175 μmol, 33%) of the title compound is isolated as a colorless oil.

Example 28c (4S,7R,8S,9S,13E,16S(Z))-4,8-Dihydroxy-16-(1-fluoro-2-(2-methyloxazol-4-yl)ethenyl)-7-(prop-2-in-1-yl)-1-oxa-5,5,9,13-tetramethyl-cyclohexadec-13-ene-2,6-dione Analogously to Example 1, 128 mg (175 μmol) of the compound that is produced according to Example 28b is reacted, and after working-up and purification, 54 mg (107 mmol, 61%) of the title compound is isolated as a colorless oil.

$^1$H-NMR (CDCl$_3$): δ=0.89 (1H), 0.98 (3H), 1.02 (3H), 1.20–2.23 (7H), 1.33 (3H), 1.59 (3H), 2.40–2.61 (6H), 2.42 (3H), 3.57 (1H), 3.77 (1H), 3.82 (1H), 3.87 (1H), 4.33 (1H), 5.08 (1H), 5.53 (1H), 5.87 (1H), 7.72 (1H) ppm.

Example 29

(4S,7R,8S,9S,13Z,16S)-4,8-Dihydroxy-16-(2-methyl-benzothiazol-5-yl)-1-oxa-5,5,9,13-tetramethyl-7-(prop-2-en-1-yl)-cyclohexadec-13-ene-2,6-dione Analogously to Example 21, 41.4 mg of the title compound is obtained from 5-chloro-2-methylbenzothiazole as a colorless oil.

$^1$H-NMR (CDCl$_3$): δ=1.04 (3H), 1.07 (3H), 1.24 (3H), 1.72 (3H), 1.3–1.8 (3H), 1.89 (1H), 2.26–2.63 (7H), 2.84 (3H), 2.90 (2H), 3.36 (1H), 3.78 (1H), 4.12 (1H), 5.05 (1H), 5.07 (1H), 5.19 (1H), 5.76 (1H), 5.88 (1H), 7.34 (1H), 7.80 (1H), 7.95 (1H) ppm.

Example 30

(4S,7R,8S,9S,13E,16S)-4,8-Dihydroxy-16-(2-methyl-benzothiazol-5-yl)-1-oxa-5,5,9,13-tetramethyl-7-(prop-2-en-1-yl)-cyclohexadec-13-ene-2,6-dione Analogously to Example 22, 108.2 mg of the title compound is obtained from 5-chloro-2-methylbenzothiazole as a colorless oil.

$^1$H-NMR (CDCl$_3$): δ=1.00 (3H), 1.05 (3H), 1.24 (3H), 1.66 (3H), 1.5–1.97 (3H), 1.75–1.99 (2H), 2.09–2.58 (7H), 2.79 (1H), 2.83 (3H), 3.56 (1H), 3.80 (1H), 3.86 (1H), 4.08 (1H), 4.49 (1H), 4.93 (1H), 5.00 (1H), 5.01 (1H), 5.73 (1H), 6.03 (1H), 7.28 (1H), 7.77 (1H), 8.00 (1H) ppm.

Example 31

(1S,3S,7S,10R,11S,12S,16R)-7,11-Dihydroxy-3-(2-methyl-benzothiazol-5-yl)-10-(prop-2-en-1-yl)-8,8,12,16-tetramethyl-4,17-dioxabicyclo[14.1.0]heptadecane-5,9-dione (A) and (1R,3S(Z),7S,10R,11S,12S,16S)-7,11-dihydroxy-3-(2-methyl-benzothiazol-5-yl)-10-(prop-2-en-1-yl)-8,8,12,16-tetramethyl-4,17-dioxabicyclo[14.1.0]heptadecane-5,9-dione (B)

Analogously to Example 10, 13.6 mg of title compound A and 4.5 mg of title compound B are obtained from 25.0 mg of the title compound that is produced in Example 29.

$^1$H-NMR (CDCl$_3$) of title compound A: δ=0.98 (3H), 1.02 (3H), 1.23 (3H), 1.32 (3H), 1.2–1.8 (7H), 2.18 (2H), 2.27 (1H), 2.43–2.69 (4H), 2.84 (3H), 2.93 (1H), 3.60 (1H), 3.69 (1H), 4.21 (1H), 4.44 (1H), 5.02 (1H), 5.06 (1H), 5.72 (1H), 6.19 (1H), 7.36 (1H), 7.82 (1H), 7.94 (1H) ppm.

$^1$H-NMR (CDCl$_3$) of title compound B: δ=0.98 (3H), 1.00 (3H), 1.31 (3H), 1.34 (3H), 1.1–1.75 (6H), 1.83 (1H), 2.0–2.65 (6H), 2.84 (3H), 3.03 (1H), 3.06 (1H), 3.28–3.43 (2H), 4.03 (1H), 4.31 (1H), 4.98 (1H), 5.03 (1H), 5.75 (1H), 6.27 (1H), 7.36 (1H), 7.81 (1H), 7.97 (1H) ppm.

Example 32

(1S,3S,7S,10R,11S,12S,16S)-7,11-Dihydroxy-3-(2-methyl-benzothiazol-5-yl)-10-(prop-2-en-1-yl)-8,8,12,16-tetramethyl-4,17-dioxabicyclo[14.1.0]heptadecane-5,9-dione (A) and (1R,3S,7S,10R,11S,12S,16R)-7,11-dihydroxy-3-(2-methyl-benzothiazol-5-yl)-10-(prop-2-en-1-yl)-8,8,12,16-tetramethyl-4,17-dioxabicyclo[14.1.0]heptadecane-5,9-dione (B)

Analogously to Example 10, 17.7 mg of title compound A and 14.6 mg of title compound B are obtained from 60.0 mg of the title compound that is produced in Example 30 by plate cleaning with a mixture that consists of methylene chloride/ethyl acetate at a 6:4 ratio.

$^1$H-NMR (CDCl$_3$) of title compound A: δ=0.96 (3H), 1.01 (3H), 1.31 (3H), 1.38 (3H), 1.2–1.9 (7H), 2.01–2.15 (1H), 2.21–2.35 (3H), 2.46–2.65 (3H), 2.83 (3H), 2.93 (1H), 3.47 (1H), 3.83 (1H), 4.20–4.34 (2H), 5.02 (1H), 5.07 (1H), 5.79 (1H), 6.13 (1H), 7.36 (1H), 7.81 (1H), 7.96 (1H) ppm.

$^1$H-NMR (CDCl$_3$) of title compound B: δ=1.01 (3H), 1.04 (3H), 1.14 (3H), 1.33 (3H), 1.1–1.75 (6H—), 2.05–2.37 (4H), 2.42–2.65 (3H), 2.84 (3H), 2.88 (1H), 3.03 (1H), 3.42 (1H), 3.49 (1H), 3.79 (1H), 4.26 (1H), 5.02 (1H), 5.06 (1H), 5.74 (1H), 6.12 (1H), 7.32 (1H), 7.80 (1H), 7.94 (1H) ppm.

Example 33

(1S,3S,7S,10R,11R,12S,16S)-7,11-Dihydroxy-3-(2-methyl-benzoxazol-5-yl)-10-(prop-2-en-1-yl)-8,8,12,16-tetramethyl-4,17-dioxabicyclo[14.1.0]heptadecane-5,9-dione (A) and (1R,3S,7S,10R,11S,12S,16R)-7,11-dihydroxy-3-(2-methyl-benzoxazol-5-yl)-10-(prop-2-en-1-yl)-8,8,12,16-tetramethyl-4,17-dioxabicyclo[14.1.0]heptadecane-5,9-dione (B)

Analogously to Example 10, 20 mg (39 μmol) of the compound that is produced according to Example 21 is reacted, and after working-up and purification, 11.2 mg (21 μmol, 54%) of title compound A and 2.9 mg (5.5 μmol, 14%) of title compound B are isolated in each case as a colorless oil.

$^1$H-NMR (CDCl$_3$) of A: δ=0.98 (3H), 1.02 (3H), 1.19–1.78 (7H), 1.22 (3H), 1.30 (3H), 2.15 (2H), 2.28 (1H), 2.33–2.60 (4H), 2.64 (3H), 2.92 (1H), 3.58 (1H), 3.69 (1H), 4.18 (1H), 4.29 (1H), 5.01 (1H), 5.08 (1H), 5.72 (1H), 6.14 (1H), 7.31 (1H), 7.47 (1H), 7.64 (1H) ppm.

Example 34

In Vitro Activity of Epothilone Derivatives on Human Tumor Cell Lines a) IC$_{50}$ values [nM] for the growth inhibition of human MCF-7-breast- and multi-drug-resistant NCI/ADR-carcinoma cell lines of epothilone derivatives with 13Z-unsaturated in the crystal-violet assay in comparison to Taxol.

TABLE 1

| Compound | MCF-7 | NCI/ADR | Selectivity* |
|---|---|---|---|
| Taxol | 3.5 | >100 | >28.6 |
| Example 1 | 30 | 75 | 2.5 |
| Example 2 | 25 | 70 | 2.8 |
| Example 9 | 17 | 41 | 2.4 |
| Example 13 | 34 | n.d. | |
| Example 15 | 25 | n.d. | |
| Example 21 | 32 | n.d. | |
| Example 23 | 11 | 62 | 5.6 |
| Example 27 | 25 | 41 | 1.6 |

*Selectivity = IC$_{50}$ – (NCl/ADR): IC$_{50}$ (MCF-7);
n.d.: not yet determined The compounds of applicants' invention have a significantly higher active strength in comparison to Taxol. All the compounds according to the invention which were tested show an action on the multi-drug-resistant cell line NCl/ADR not exhibited by Taxol.

b) IC$_{50}$ values [nM] for the growth inhibition of human MCF-7-breast- and multi-drug-resistant NCl/ADR carcinoma cell lines of epothilone derivative with 13,14-α-epoxide, which was formed from the 13-Z-configured double bond in the crystal-violet assay in comparison to Taxol.

TABLE 2

| Compound | MCF-7 | NCl/ADR | Selectivity* |
|---|---|---|---|
| Taxol | 3.5 | >100 | >29 |
| Example 4A | 1.3 | 9.1 | 7.0 |
| Example 5A | 3.1 | 3.8 | 1.2 |
| Example 10A | 1.2 | 3.6 | 3.0 |
| Example 25 | 2.3 | 11 | 4.8 |

*Selectivity = IC$_{50}$ – (NCl/ADR): IC$_{50}$ – (MCF-7)

In contrast to Taxol, all compounds of the invention show an action on the multi-drug-resistant cell line NCl/ADR.

c) IC$_{50}$ values [nM] for the growth inhibition of human MCF-7-breast- and multi-drug-resistant NCl/ADR-carcinoma cell lines of epothilone derivatives with 13,14-epoxide, which was formed from the 13-E-configured double bond, in a crystal-violet assay in comparison to Taxol.

Table 3

| Compound | MCF-7 | NCl/ADR | Selectivity* |
|---|---|---|---|
| Taxol | 3.5 | >100 | >29 |
| Example 6A or B | 4.3 | 68 | 15.8 |
| Example 12A or B | 40 | 61 | 1.5 |
| Example 12B or A | 4.8 | 53 | 11.0 |
| Example 26A or B | 18 | 60 | 3.3 |

*Selectivity = IC$_{50}$ – (NCl/ADR): IC$_{50}$ – (MCF-7)

In contrast to Taxol, all compounds show an action on the multi-drug-resistant cell line NCl/ADR.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An epothilone compound of formula I,

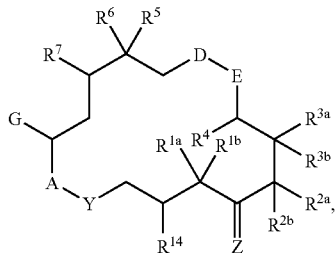

in which
R$^{1a}$, R$^{1b}$ are the same or different and mean hydrogen; C$_1$–C$_{10}$ alkyl, C$_6$–C$_{12}$ aryl, or C$_7$–C$_{20}$ aralkyl, each, except hydrogen, is optionally substituted;
R$^{2a}$ means hydrogen, C$_1$–C$_{10}$ alkyl, C$_6$–C$_{12}$ aryl or C$_7$–C$_{20}$ aralkyl, each, except hydrogen, is optionally substituted;
—(CH$_2$)$_{ra}$—C≡C—(CH$_2$)$_{pa}$—R$^{26a}$;
or —(CH$_2$)$_{ra}$—CH=CH—(CH$_2$)$_{pa}$—R$^{26a}$,
R$^{2b}$ means —(CH$_2$)$_{rb}$—C≡C—(CH$_2$)$_{pb}$—R$^{26b}$, or —(CH$_2$)$_{rb}$—CH=CH—(CH$_2$)$_{pb}$—R$^{26b}$,
ra, rb are the same or different and mean 0 to 4,
pa, pb are the same or different and mean 0 to 3,
R$^{3a}$ means hydrogen or a C$_1$–C$_{10}$ alkyl, C$_6$–C$_{12}$ aryl or C$_7$–C$_{20}$ aralkyl, each, except hydrogen, is optionally substituted,
R$^{3b}$ means OH or OPG$^{14}$ where PG$^{14}$ is a protective group,
R$^{14}$ means hydrogen, OR$^{14a}$ or Hal, where R$^{14a}$ is hydrogen, SO$_2$-alkyl, SO$_2$-aryl or SO$_2$-aralkyl,
R$^4$ means hydrogen, C$_1$–C$_{10}$ alkyl, C$_6$–C$_{12}$ aryl or C$_7$–C$_{20}$ aralkyl, each, except hydrogen, is optionally substituted Hal; OR$^{25}$; or CN;
R$^{25}$ means hydrogen or a protective group PG$^5$,
R$^{26}$, R$^{26b}$ are the same or different and mean hydrogen; C$_1$–C$_{10}$ alkyl, C$_6$–C$_{12}$ aryl or C$_7$–C$_{20}$ aralkyl, each, except hydrogen, is optionally substituted C$_1$–C$_{10}$ acyl, or, if pa or pb>0, additionally a group OR$^{27}$,
R$^{27}$ means hydrogen or a protective group PG$^6$,
R$^5$ means hydrogen, C$_1$–C$_{10}$ alkyl, C$_6$–C$_{12}$ aryl, C$_7$–C$_{20}$ aralkyl, each optionally substituted; or (CH$_2$)$_s$-T,
whereby
s stands for 1, 2, 3 or 4,
T stands for OR$^{22}$ or Hal,
R$^{22}$ stands for hydrogen or a protective group PG$^4$,
R$^6$, R$^7$ each mean a hydrogen atom, or taken together an additional bond or an oxygen atom,
G means a benzothiazolyl, benzoxazolyl or quinolinyl radical which is optionally substituted by halogen, OH, O-alkyl, CO$_2$H, CO$_2$-alkyl, —NH$_2$, —NO$_2$, —N$_3$, —CN, C$_1$–C$_{20}$ alkyl, C$_1$–C$_{20}$ acyl, or C$_1$–C$_{20}$ acyloxy groups,
D-E means a group —CH$_2$—CH$_2$—,
A-Y means a group O—C(=O), or NR$^{29}$—C(=O),
R$^{29}$ means hydrogen or C$_1$–C$_{10}$ alkyl,
Z means an oxygen atom,
Hal means halogen,
wherein, in each occurrence "PG" together means a hydroxy protecting group.

2. A compound of formula I according to claim 1, wherein R$^{2a}$ stands for a hydrogen atom.

3. A compound of formula I according to claim 1, wherein R$^{1a}$ and R$^{1b}$ in each case stand for a methyl group.

4. A compound of the formula I of claim 1, wherein R$^{2a}$ is hydrogen.

5. A compound of the formula I of claim 1, wherein R$^{2a}$ is hydrogen and R$^{2b}$ is allyl, prop-2-inyl, but-3-inyl or but-3-enyl.

6. A compound of the formula I of claim 1, wherein R$^{3a}$ and R$^{3b}$ taken together are H/OH.

7. A compound of the formula I of claim 1, wherein R$^4$ is methyl, ethyl, propyl, n-butyl, i-butyl, t-butyl or benzyl.

8. A compound of the formula I of claim 1, wherein R$^5$ is H, C$_{1-5}$ alkyl or —(CH$_2$)$_s$-T where T is OH, F or Cl and s is 1 or 2.

9. A compound of the formula I of claim 1, wherein G is a 2-methyl-benzothiazol-5-yl 2-methyl-benzoxazol-5-yl or quinolin-7-yl radical.

10. A compound of claim 9, wherein G is a 2-methylbenzoxazol-5-yl or 2-methylbenzothiazol-5-yl radical.

11. A compound of the formula I of claim 1, wherein -A—Y— is —O—C(=O) or —NR$^{29}$—C(=O)— wherein R$^{29}$ is hydrogen or C$_1$–C$_3$ alkyl.

12. A pharmaceutical composition comprising a compound of the formula I of claim 1 and at least one pharmaceutically acceptable adjuvant or vehicle.

13. A composition according to claim 12 in the form of a dosage unit containing 0.1–100 mg of the compound of the formula I of claim 1.

14. A method for treating ovarian, stomach, colon, adeno-, breast, lung, head or neck carcinomas, malignant melanoma or acute lymphocytic or myelocytic leukemia which comprises administering to a patient in need thereof a compound of the formula I of claim 1.

15. A method of claim 14, wherein the compound of formula I is administered to a human in a dosage of 0.1–100 mg/day.

16. A method for preparing a compound of the formula I, of claim 1, which comprises:
cyclizing a compound of the formula ABC-1 or ABC-2

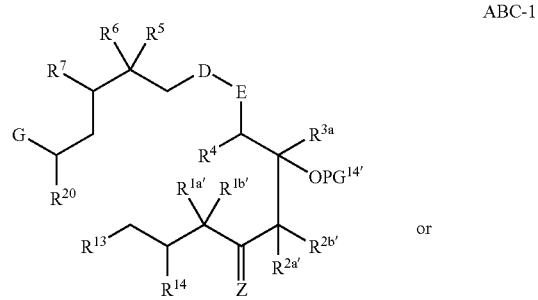

ABC-1 or

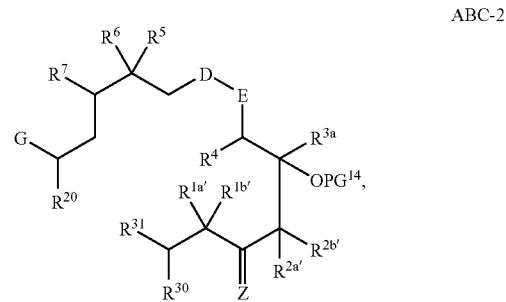

ABC-2 wherein R$^{14}$, Z, R$^3$, R$^4$, D, E, R$^5$, R$^6$, R$^7$ and G have the meaning given in claim 1, $R^{1a'}$, $R^{1b'}$, $R^{2a'}$ and $R^{2b'}$ have the meanings given for $R^{1a}$, $R^{1b}$, $R^{2a}$ and $R^{2b}$ in claim 1

$R^{13}$ means $CH_2OR^{13a}$, $CH_2$-Hal, CHO, $CO_2R^{13b}$ or COHal $R^{13a}$ means hydrogen, $SO_2$-alkyl, $SO_2$-aryl, $SO_2$-aralkyl or together with $R^{14a}$ can be —$(CH_2)_o$— where o=2 to 4 group or together with $R^{14a}$ can be a $C^{15a}R^{15b}$ group, $R^{13b}$ means hydrogen, $C_1$–$C_{20}$ alkyl, $C_6$–$C_{12}$ aryl, $C_7$–$C_{20}$ aralkyl, each, except hydrogen, is optionally substituted, $R^{15a}$, $R^{15b}$ are the same or different and mean hydrogen, $C_1$–$C_{10}$ alkyl, aryl, $C_7$–$C_{20}$ aralkyl or together, $R^{15a}$ and $R^{15b}$ can be a —$(CH_2)_q$— group where $q$ is 3 to 6, $PG^{14'}$ is hydrogen or a protecting group, $R^{20}$ means halogen, $N_3$, $NHR^{29}$, a hydroxy group, a protected hydroxy group O—$PG^2$, a protected amino group $NR^{29}PG^2$, a $C_1$–$C_{10}$ alkylsulfonyloxy group, which optionally can be perfluorinated, a benzoyloxy group that is optionally substituted by $C_1$–$C_4$ alkyl, nitro, chlorine or bromine, an $NR^{29}SO_2CH_3$ group, an $NR^{29}C(=O)CH_3$ group, a $CH_2$—$C(=O)$—$CH_3$ group, $R^{30}$ means hydrogen, $R^{31}$ means hydroxyl, or $R^{30}$, $R^{31}$ together mean an oxygen atom or a $C_2$–$C_{10}$ alkylene-α,ω-dioxy group, which can be straight-chain or branched, or $R^{30}$, $R^{31}$ independently mean a $C_1$–$C_{10}$ alkoxy group.

17. The method of claim 16, wherein the compound of formula ABC-1 or ABC-2 is prepared by reacting an intermediate AB-1 or AB-2:

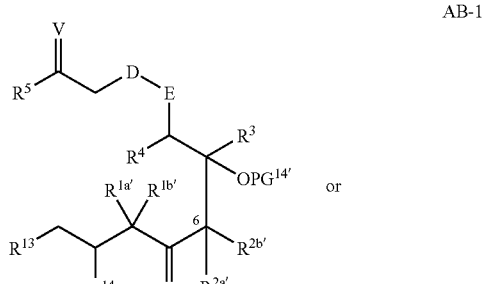

AB-1

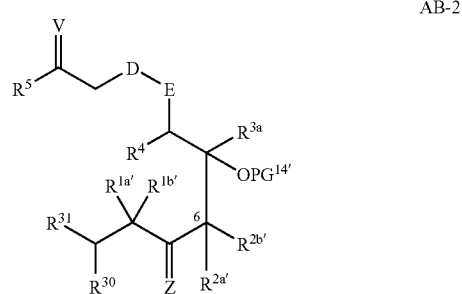

AB-2 with a fragment $C_f$,

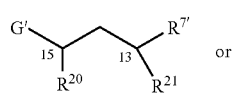

Cf or reacting intermediate BC

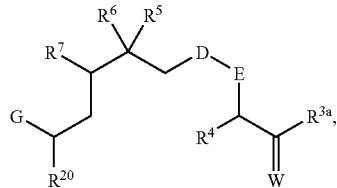

BC with a fragment A-1 or A-2:

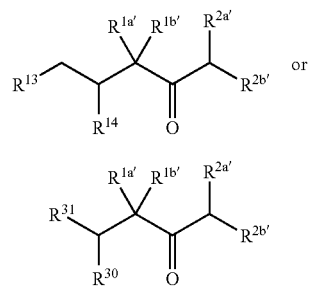

A-1

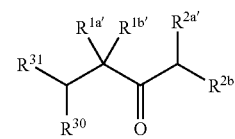

A-2 wherein

V means an oxygen atom, two alkoxy groups $OR^{17}$, a $C_2$–$C_{10}$ alkylene-α,ω-dioxy group, which can be straight-chain or branched or $H/OR^{16}$, W means an oxygen atom, two alkoxy groups $OR^{19}$, a $C_2$–$C_{10}$-alkylene-α,ω-dioxy group, which can be straight-chain or branched or $H/OR^{18}$, $R^{16}$, $R^{18}$, independently of one another, mean hydrogen or a protective group $PG^1$, $R^{17}$, $R^{19}$, independently of one another, mean $C_1$–$C_{20}$ alkyl optionally substituted, G' means a benzothiazolyl, benzoxazolyl or quinolinyl radical which is optionally substituted by halogen, OH, O-alkyl, $CO_2H$, $CO_2$-alkyl, —$NH_2$, —$NO_2$, —$N_3$, —CN, $C_1$–$C_{20}$ alkyl, $C_1$–$C_{20}$ acyl, or $C_1$–$C_{20}$ acyloxy groups, $R^{7'}$ means a hydrogen atom, $R^{13a}$ means hydrogen, $SO_2$-alkyl, $SO_2$-aryl, $SO_2$-aralkyl or together a —$(CH_2)_o$—group or together a $CR^{15a}R^{15b}$ group, $R^{13b}$ means hydrogen, $C_1$–$C_{20}$ alkyl, $C_6$–$C_{12}$ aryl, $C_7$–$C_{20}$ aralkyl, each, except hydrogen, is optionally substituted, $R^{15a}$, $R^{15b}$ are the same different and mean hydrogen, $C_1$–$C_{10}$ alkyl, aryl, $C_7$–$C_{20}$ aralkyl or together a —$(CH_2)_q$— group, $R^{21}$ means a hydroxy group, halogen, a protected hydroxy group $OPG^3$, a phosphonium halide radical $PPH_3^+Hal^-$ (Ph=phenyl; Hal—F, Cl, Br, I), a phosphonate radical $P(O)(OQ)_2$ (Q=$C_1$–$C_{10}$ alkyl or phenyl) or a phosphine oxide radical $P(O)Ph_2$ (Ph=phenyl)

$R^{14'}$ means hydrogen, $OR^{14a}$, Hal, $OSO_2R^{14b}$, $R^{14a}$ means hydrogen, $SO_2$-alkyl, $SO_2$-aryl, or $SO_2$-aralkyl, $R^{14b}$ means hydrogen, $C_1$–$C_{20}$ alkyl, $C_6$–$C_{12}$ aryl, $C_7$–$C_{20}$ aralkyl, each, except hydrogen, is optionally substituted, o means 2 to 4, q means 3 to 6, and the other variables are as defined above.

18. The method of claim 17, wherein the intermediates AB-1 and AB-2 are prepared by reacting fragments A-1, A-2 or C$_f$ with fragment B$_f$

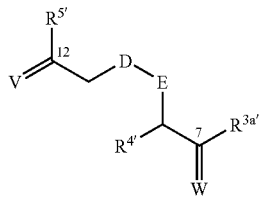

wherein R$^{3a'}$, R$^{4'}$ and R$^{5'}$ have the meanings given for R$^{3a}$, R$^4$, R$^5$, respectively.

19. A compound of the formula I of claim 1, which is:
(1S,3S,7S,10R,11S,12S,16R)-7,11-dihydroxy-3-(2-methyl-benzothiazol-5-yl)-10-(prop-2-en-1-yl)-8,8,12,16-tetramethyl-4,17-dioxabicyclo[14.1.0]heptadecane-5,9-dione; of the following formula:

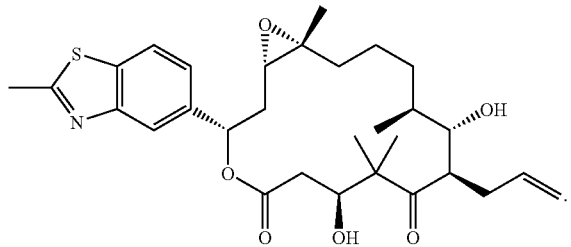

20. A compound of formula I according to claim 1, selected from the group consisting of:
(4S,7R,8S,9S,13E/Z,16S)-4,8-dihydroxy-16-(2-methyl-benzoxazol-5-yl)-1-oxa-5,5,9,13-tetramethyl-7-(prop-2-en-1-yl)-cyclohexadec-13-ene-2,6-dione;
(1S/R,3S,7S,10R,11R,12S,16R/S)-7,11-dihydroxy-10-(prop-2-en-1-yl)-3-(2-methyl-benzoxazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzoxazol-5-yl)-1-oxa-5,5,9,13-tetramethyl-7-(prop-2-in-1-yl)-cyclohexadec-13-ene-2,6-dione;
(1S/R,3S,7S,10R,11R,12S,16R/S)-7,11-dihydroxy-10-(prop-2-in-1-yl)-3-(2-methyl-benzoxazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzoxazol-5-yl)-1-oxa-5,5,9,13-tetramethyl-7-(but-3-en-1-yl)-cyclohexadec-13-ene-2,6-dione;
(1S/R,3S,7S,10R,11R,12S,16R/S)-7,11-dihydroxy-10-(but-3-en-1-yl)-3-(2-methyl-benzoxazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzoxazol-5-yl)-1-oxa-5,5,9,13-tetramethyl-7-(but-3-in-1-yl)-cyclohexadec-13-ene-2,6-dione;
(1S/R,3S,7S,10R,11R,12S,16R/S)-7,11-dihydroxy-10-(but-3-in-1-yl)-3-(2-methyl-benzoxazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzoxazol-5-yl)-1-oxa-5,5,9,13-tetramethyl-7-(3-methyl-but-2-en-1-yl)-cyclohexadec-13-ene-2,6-dione;
(1S/R,3S,7S,10R,11R,12S,16R/S)-7,11-dihydroxy-10-(3-methyl-but-2-en-1-yl)-3-(2-methyl-benzoxazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzothiazol-5-yl)-1-oxa-5,5,9,13-tetramethyl-7-(prop-2-en-1-yl)-cyclohexadec-13-ene-2,6-dione;
(1S/R,3S,7S,10R,11R,12S,16R/S)-7,11-dihydroxy-10-(prop-2-en-1-yl)-3-(2-methyl-benzothiazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzothiazol-5-yl)-1-oxa-5,5,9,13-tetramethyl-7-(prop-2-in-1-yl)-cyclohexadec-13-ene-2,6-dione;
(1S/R,3S,7S,10R,11R,12S,16R/S)-7,11-dihydroxy-10-(prop-2-in-1-yl)-3-(2-methyl-benzothiazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzothiazol-5-yl)-1-oxa-5,5,9,13-tetramethyl-7-(but-3-en-1-yl)-cyclohexadec-13-ene-2,6-dione;
(1S/R,3S,7S,10R,11R,12S,16R/S)-7,11-dihydroxy-10-(but-3-en-1-yl)-3-(2-methyl-benzothiazol-5-yl)-8,8,12,16-tetramethyl-4,17-dioxabicyclo[14.1.0]heptadecane-5,9-dione;
(4S,7R,8S,9S,13E/Z, 16S)-4,8-dihydroxy-16-(2-methyl-benzothiazol-5-yl)-1-oxa-5,5,9,13-tetramethyl-7-(but-3-in-1-yl)-cyclohexadec-13-ene-2,6-dione;
(1S/R,3 S,7S,10R,11R,12S,16R/S)-7,11-dihydroxy-10-(but-3-in-1-yl)-3-(2-methyl-benzothiazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzothiazol-5-yl)-1-oxa-5,5,9,13-tetramethyl-7-(3-methyl-but-2-en-1-yl)-cyclohexadec-13-ene-2,6-dione;
(1S/R,3S,7S,10R,11R,12S,16R/S)-7,11-dihydroxy-10-(3-methyl-but-2-en-1-yl)-3-(2-methyl-benzothiazol-5-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(quinolin-7-yl)-1-oxa-5,5,9,13-tetramethyl-7-(prop-2-en-1-yl)-cyclohexadec-13-ene-2,6-dione;
(1S/R,3S,7S,10R,11R,12S,16R/S)-7,11-dihydroxy-10-(prop-2-en-1-yl)-3-(quinolin-7-yl)-8,8,12,16-tetramethyl-4,17-dioxabicyclo[14.1.0]heptadecane-5,9-dione;
(4S,7R,8S,9S,13E/Z,16S)-4,8-dihydroxy-16-(2-methyl-benzoxazol-5-yl)-1-aza-5,5,9,13-tetramethyl-7-(prop-2-in-1-yl)-cyclohexadec-13-ene-2,6-dione;
(1S/R,3S,7S,10R,11R,12S,16R/S)-7,11-dihydroxy-10-(prop-2-in-1-yl)-3-(2-methyl-benzoxazol-5-yl)-8,8,12,16-tetramethyl-4-aza-17-oxabicyclo[14.1.0]heptadecane-5,9-dione;
(4S,7R,8S,9S,13E/Z,16S)-4,8-dihydroxy-16-(2-methyl-benzoxazol-5-yl)-1-aza-5,5,9,13-tetramethyl-7-(but-3-en-1-yl)-cyclohexadec-13-ene-2,6-dione;
(1S/R,3S,7S,10R,11R,12S,16R/S)-7,11-dihydroxy-10-(but-3-en-1-yl)-3-(2-methyl-benzoxazol-5-yl)-8,8,12,16-tetramethyl-4-aza-17-oxabicyclo[14.1.0]heptadecane-5,9-dione;
(4S,7R,8S,9S,13E/Z,16S)-4,8-dihydroxy-16-(2-methyl-benzoxazol-5-yl)-1-aza-5,5,9,13-tetramethyl-7-(but-3-in-1-yl)-cyclohexadec-13-ene-2,6-dione;

(1S/R,3S,7S,10R,11R,12S,16R/S)-7,11-dihydroxy-10-(but-3-in-1-yl)-3-(2-methyl-benzoxazol-5-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(2-methyl-benzoxazol-5-yl)-1-aza-5,5,9,13-tetramethyl-7-(3-methyl-but-2-en-1-yl)-cyclohexadec-13-ene-2,6-dione;

(1S/R,3S,7S,10R,11R,12S,16R/S)-7,11-dihydroxy-10-(3-methyl-but-2-en-1-yl)-3-(2-methyl-benzoxazol-5-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(2-methyl-benzothiazol-5-yl)-1-aza-5,5,9,13-tetramethyl-7-(prop-2-en-1-yl)-cyclohexadec-13-ene-2,6-dione;

(1S/R,3S,7S,10R,11R,12S,16R/S)-7,11-dihydroxy-10-(prop-2-en-1-yl)-3-(2-methyl-benzothiazol-5-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(2-methyl-benzothiazol-5-yl)-1-aza-5,5,9,13-tetramethyl-7-(prop-2-in-1-yl)-cyclohexadec-13-ene-2,6-dione;

(1S/R,3S,7S,10R,11R,12S,16R/S)-7,11-dihydroxy-10-(prop-2-in-1-yl)-3-(2-methyl-benzothiazol-5-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(2-methyl-benzothiazol-5-yl)-1-aza-5,5,9,13-tetramethyl-7-(but-3-en-1-yl)-cyclohexadec-13-ene-2,6-dione;

(1S/R,3S,7S,10R,11R,12S,16R/S)-7,11-dihydroxy-10-(but-3-en-1-yl)-3-(2-methyl-benzothiazol-5-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(2-methyl-benzothiazol-5-yl)-1-aza-5,5,9,13-tetramethyl-7-(but-3-in-1-yl)-cyclohexadec-13-ene-2,6-dione;

(1S/R,3S,7S,10R,11R,12S,16R/S)-7,11-dihydroxy-10-(but-3-in-1-yl)-3-(2-methyl-benzothiazol-5-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(2-methyl-benzothiazol-5-yl)-1-aza-5,5,9,13-tetramethyl-7-(3-methyl-but-2-en-1-yl)-cyclohexadec-13-ene-2,6-dione;

(1S/R,3S,7S,10R,11R,12S,16R/S)-7,11-dihydroxy-10-(3-methyl-but-2-en-1-yl)-3-(2-methyl-benzothiazol-5-yl)-8,8,12,16-tetramethyl-4-aza-17-oxabicyclo[14.1.0]heptadecane-5,9-dione.

21. A compound of formula I of claim 1, wherein each protective group, defined as PG groups, is selected from alkyl- and/or aryl-substituted silyl, $C_1$–$C_{20}$ alkyl, $C_4$–$C_7$ cycloalkyl which optionally contains an oxygen atom in the ring, aryl, $C_7$–$C_{20}$ aralkyl, $C_1$–$C_{20}$ acyl, aroyl and $C_1$–$C_{20}$ alkoxycarbonyl.

22. A method of claim 16, wherein each hydroxy protective group is selected from alkyl- and/or aryl-substituted silyl, $C_1$–$C_{20}$ alkyl, $C_4$–$C_7$ cycloalkyl which optionally contains an oxygen atom in the ring, aryl, $C_7$–$C_{20}$ aralkyl, $C_1$–$C_{20}$ acyl, aroyl and $C_1$–$C_{20}$ alkoxycarbonyl; and each amino protecting group is selected from Alloc-, Boc-, Z-, benzyl, f-Moc, Troc, Stabase or Benzostabase protecting groups.

23. A method of claim 17, wherein each hydroxy protective group is selected from alkyl- and/or aryl-substituted silyl, $C_1$–$C_{20}$ alkyl, $C_4$–$C_7$ cycloalkyl which optionally contains an oxygen atom in the ring, aryl, $C_7$–$C_{20}$ aralkyl, $C_1$–$C_{20}$ acyl, aroyl and $C_1$–$C_{20}$ alkoxycarbonyl; and each amino protecting group is selected from Alloc-, Boc-, Z-, benzyl, f-Moc, Troc, Stabase or Benzostabase protecting groups.

24. A compound of formula I according to claim 1, selected from the group consisting of:

(4S, 7R, 8S, 9S, 13E/Z, 16S)-4,8-dihydroxy-16-(quinolin-7-yl)-1-oxa-5,5,9,13-tetramethyl-7-(prop-2-en1-yl)-cyclohexadec-13-ene-2,6-dione;

(1S/R,3S,7S,10R,11R,12S,16R/S)-7,11-dihydroxy-10-(prop-2-en-1-yl)-3-(quinolin-7-yl)-8,8,12,16-tetramethyl-4,17-dioxabicyclo[14.1.0]heptadecane-5,9-dione;

(4S,7R,8S,9S, 13E/Z, 16S)-4,8-dihydroxy-16-(quinolin-7-yl)-1-oxa- 5,5,9,13-tetramethyl-7-(prop-2-in-1-yl)-cyclohexadec-13-ene-2,6-dione;

(1S/R,3S,7S,10R,11R,12S,16R/S)-7,11-dihydroxy-10-(prop-2-in-1-yl)-3- (quinolin-7-yl)-8,8,12,16-tetramethyl-4,17-dioxabicyclo[14.1.0]heptadecane-5,9-dione;

(4S,7R,8S,9S,13E/Z,16S)-4,8-dihydroxy-16-(quinolin-7-yl)-1-oxa-5,5,9,13- tetramethyl-7-(but-3-en-1-yl)-cyclohexadec-13-ene-2,6-dione;

(1S/R,3S,7S,10R,11R,12S,16R/S)-7,11-dihydroxy-10-(but-3-en-1-yl)-3- (quinolin-7-yl)-8,8,12,16-tetramethyl-4,17-dioxabicyclo[14.1.0]heptadecane-5,9-dione;

(4S,7R,8S,9S,13E/Z,16S)-4,8-dihydroxy-16-(quinolin-7-yl)-1-oxa- 5,5,9,13-tetramethyl-7-(but-3-in-1-yl)-cyclohexadec-13-ene-2,6-dione;

(IS/R,3S,7S,10R,11R,12S,16R/S)-7,11-dihydroxy-10-(but-3-in-1-yl)-3-(quinolin- 7-yl)-8,8,12,16-tetramethyl-4,17-dioxabicyclo[14.1.0]heptadecane-5,9-dione;

(4S,7R,8S,9S,13E/Z,16S)-4,8-dihydroxy-16-(quinolin-7-yl)-1-oxa-5,5,9,13- tetramethyl-7-(3-methyl-but-2-en-1-yl)-cyclohexadec-13-ene-2,6-dione;

(1S/R,3S,7S,10R,11R,12S,16R/S)-7,11-dihydroxy-10-(3-methyl-but-2-en-1-yl)- 3-(quinolin-7-yl)-8,8,12,16-tetramethyl-4,17-dioxabicyclo[14.1.0]heptadecane-5,9-dione;

(4S,7R,8S,9S,13E/Z,16S)-4,8-dihydroxy-16-(quinolin-7-yl)-1-aza-5,5,9,13- tetramethyl-7-(prop-2-en-1-yl)-cyclohexadec-13-ene-2,6-dione;

(1S/R,3S,7S,10R,11R,12S,16R/S)-7,11-dihydroxy-10-(prop-2en-1-yl)-3-(quinolin- 7-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(quinolin-7-yl)-1- aza-5,5,9,13-tetramethyl-7-(prop-2-in-1-yl)-cyclohexadec-13-ene-2,6-dione;

(1S/R,3S,7S,10R,11,12S,16R/S)-7,11-dihydroxy-10-(prop-2-in-1-yl)-3-(quinolin- 7-yl)-8,8,12,16-tetramethyl-4-aza-17-oxabicyclo[14.1.0]heptadecane-5,9-dione;

(4S,7R,8S,9S,13E/Z,16S)-4,8-dihydroxy-16-(quinolin-7-yl)-1-aza-5,5,9,13- tetramethyl-7-(but-3-en-1-yl)-cyclohexadec-13-ene-2,6-dione;

(1S/R,3S,7S,10R,11R,12S,16R/S)-7,11-dihydroxy-10 (but-3-en-1-yl)-3-(quinolin-7-yl) -8,8,12,16-tetramethyl-4-aza-17-oxabicyclo[14.1.0]heptadecane-5,9-dione;

(4S,7R,8S,9S,13E/Z,16S)-4,8-dihydroxy-16-(quinolin-7-yl)-1-aza-5,5,9,13- tetramethyl-7-(but-3-in-1-yl)-cyclohexadec-13-ene-2,6-dione;

(1S/R,3S,7S,10R,11R,12S,16R/S)7,11-dihydroxy-10-(but-3-in-1-yl)-3-(quinolin-7-yl) -8,8,12,16-tetramethyl-4-aza-17-oxabicyclo[14.1.0]heptadecane-5,9-dione;

(4S,7R,8S,9S,13E/Z,16S)-4,8-dihydroxy-16-(quinolin-7-yl)-1-aza-5,5,9,13- etramethyl-7-(3-methyl-but-2-en-1-yl)-cyclohexadec-13-ene-2,6-dione; and (1S/R,3S,7S,10R,11R,12S,16R/S)-7,11-dihydroxy-10-(3-methyl-but-2-en-1-yl)-3- (quinolin-7-yl)-8,8,12,16-tetramethyl-4-aza-17-oxabicyclo[14.1.0]heptadecane-5,9-dione.

* * * * *

UNITED STATES PATENT AND TRADEMARK OFFICE
CERTIFICATE OF CORRECTION

| | | |
|---|---|---|
| PATENT NO. | : 7,125,893 B1 | Page 1 of 2 |
| APPLICATION NO. | : 09/979939 | |
| DATED | : October 24, 2006 | |
| INVENTOR(S) | : Ulrich Klar | |

It is certified that error appears in the above-identified patent and that said Letters Patent is hereby corrected as shown below:

On the Title Page, Item (75) Inventors: line 5, reads "Muhlenbeck" should read -- Muehlenbeck --

Column 91, line 38, reads "optionally substituted" should read -- optionally substituted; --

Column 91, line 41, reads "$R^{26}$," should read -- $R^{26a}$, --

Column 91, line 43, reads "substituted $C_1$-$C_{10}$" should read -- substituted; $C_1$-$C_{10}$ --

Column 92, line 16, reads "...5-yl 2-methyl..." should read -- ... 5-yl, 2-methyl... --

Column 93, line 24, reads "group," should read -- group where $R^{29}$ is hydrogen or $C_{1-10}$alkyl, --

Column 93, line 60, reads "fragment $C_r$," should read -- fragment Cf, --

Column 93, line 63, in fragment Cf, delete "15", "13", and "or"

Column 94, line 43, reads "$R^{13a}$" should read -- $R^{13}$ --

Column 94, line 44, reads "-$(CH_2)_o$-group" should read -- -$(CH_2)_o$- group --

Column 94, line 44, reads "together a" should read -- together with $R^{14}$ is a --

Column 94, line 49, reads "same different" should read -- same or different --

Column 94, line 50, reads "or together a" should read -- or and $R^{15a}$ and $R^{15b}$ together are a --

Column 94, line 51, "-$(CH_2)_q$-group," should read -- -$(CH_2)_q$- group, --

Column 94, line 54, reads "$PPH_3^+Hal^-$" should read -- $PPh_3^+Hal^-$ --

Column 94, line 57, reads "$R^{14}$'" should read -- $R^{14}$ --

Column 96, line 33, reads "3  S," should read -- 3S, --

Column 96, lines 44-49, replace with
-- (4S,7R,8S,13E/Z,16S)-4,8-dihydroxy-16-(2-methyl-benzoxazol5-yl)-1-aza-5,5,9,13-
tetramethyl-7-(prop-2-en-1-yl)-cyclohexadec-13-ene-2,6-dione;
(1S/R,3S,7S,10R,11R,12S,16R/S)-7,11-dihydroxy-10-(prop-2-en-1-yl)-3-(2-
methyl-benzoxazol-5-yl)-88,12,16-tetramethyl-4-aza-17-oxabicyclo[14.1.0]
heptadecane-5,9-dione; --

Column 98, line 7, reads "prop-2-en1-yl" should read -- prop-2-en-1-yl --

Column 98, line 27, reads "IS/R" should read -- 1S/R --

Column 98, line 40, reads "prop-2en-1-yl" should read -- prop-2-en-1-yl --

UNITED STATES PATENT AND TRADEMARK OFFICE
CERTIFICATE OF CORRECTION

PATENT NO. : 7,125,893 B1
APPLICATION NO. : 09/979939
DATED : October 24, 2006
INVENTOR(S) : Ulrich Klar It is certified that error appears in the above-identified patent and that said Letters Patent is hereby corrected as shown below:

Column 98, line 61, reads "etramethyl" should read --tetramethyl --

Signed and Sealed this

Twenty-ninth Day of May, 2007

JON W. DUDAS
*Director of the United States Patent and Trademark Office*